United States Patent
Gorelik et al.

(10) Patent No.: US 7,433,035 B2
(45) Date of Patent: Oct. 7, 2008

(54) DETECTION OF CARBON HALOGEN BONDS

(75) Inventors: Vladimir Semenovich Gorelik, Moscow (RU); Clay Marcus Sharts, deceased, late of La Mesa CA (US); by Olga N. Sharts, legal representative, La Mesa, CA (US); Robert P. Metzger, La Jolla, CA (US); Dale F. Shellhamer, San Diego, CA (US); Georg R. Wischnath, Guetersloh (DE)

(73) Assignee: San Diego State University Research Foundation, San Diego, CA (US)

( * ) Notice: Subject to any disclaimer, the term of this patent is extended or adjusted under 35 U.S.C. 154(b) by 353 days.

(21) Appl. No.: 10/234,580

(22) Filed: Aug. 30, 2002

(65) Prior Publication Data
US 2003/0133105 A1    Jul. 17, 2003

Related U.S. Application Data

(63) Continuation-in-part of application No. 09/947,312, filed on Sep. 5, 2001, now Pat. No. 6,445,449, which is a continuation of application No. 09/343,148, filed on Jun. 29, 1999, now Pat. No. 6,307,625.

(60) Provisional application No. 60/138,643, filed on Jun. 10, 1999, provisional application No. 60/091,090, filed on Jun. 29, 1998.

(51) Int. Cl.
G01J 3/44 (2006.01)
G01N 21/65 (2006.01)

(52) U.S. Cl. ........................................ 356/301

(58) Field of Classification Search ................ 356/301, 356/317, 318, 417; 250/458.1, 461.1, 461.2, 250/459.1
See application file for complete search history.

(56) References Cited

U.S. PATENT DOCUMENTS

| | | | |
|---|---|---|---|
| 5,084,617 A * | 1/1992 | Gergely | 250/461.1 |
| 5,088,820 A | 2/1992 | Winefordner et al. | |
| 5,115,137 A * | 5/1992 | Andersson-Engels et al. | 250/461.2 |
| 5,216,483 A * | 6/1993 | Berthold et al. | 356/318 |
| 5,304,492 A * | 4/1994 | Klinkhammer | 250/458.1 |
| 5,780,232 A | 7/1998 | Alinghaus et al. | |
| 6,040,191 A | 3/2000 | Grow | |
| 6,274,385 B1 | 8/2001 | Hochlowski et al. | |
| 6,287,869 B1 | 9/2001 | Hug et al. | |
| 6,307,625 B1 | 10/2001 | Sharts et al. | |
| 6,569,630 B1 | 5/2003 | Vivekananda et al. | |
| 6,645,455 B2 | 11/2003 | Margrave et al. | |
| 6,697,665 B1 * | 2/2004 | Rava et al. | 600/475 |
| 2001/0007751 A1 | 7/2001 | Yanagawa et al. | |
| 2001/0039011 A1 | 11/2001 | Yanagawa et al. | |
| 2003/0157374 A1 | 8/2003 | Kato et al. | |

OTHER PUBLICATIONS

Harkins et al., The Raman Effect and The Carbon-Halogen Bond, Physical Review, vol. 38, Nov. 15, 1931, pp. 1845-1857.*

(Continued)

*Primary Examiner*—F. L Evans
(74) *Attorney, Agent, or Firm*—Shekhar Vyas; Dale L. Rieger; Edward W. Callan

(57) ABSTRACT

Detecting and determination of halooorganic compounds is described, which is applicable in the pharmaceutical industry, in fluorinated drug research and manufacturing; in the medical and clinical studies of the effects of fluoroorganic compounds; in the environmental and agricultural studies and screening, in the analysis of water, soils and air contaminated with fluoroorganic compounds.

11 Claims, 40 Drawing Sheets

OTHER PUBLICATIONS

S. A. Asher, X. G. Chen, N. Cho, S. Krimm, and N. Mirkin, "UV Ran-tan Spectroscopic Studies of Peptides and Proteins", *Proceedings of the XIVth International Conference on Raman Spectroscopy (ICORS)*, Silver Jubilee, Aug. 22-26, 1994, Hong Kong, Edited by N.-T. Yu and X. Y. Li: 43-46.

Gerald T. Babcock and Costas Varotsis, "Time-resolved resonance Raman Resolution of an Enzyme Reaction: Activation and Reduction of $O_2$ by Cytochrome Oxidase," *Proceedings of the XIVth International Conference on Raman Spectroscopy (ICORS)*, Silver Jubilee, Aug. 22-26, 1994, Hong Kong. Edited by N.-T. Yu and X. Y. Li: 82-83.

Satoshi Takahashi and Denis Rousseau. "Resonance Raman Characterization of Biological Reaction Intermediates Generated in Less than 100 μs by Rapid Solution Mixing," *Proceedings of the XIVth International Conference on Raman Spectroscopy (ICORS)*, Silver Jubilee, Hong Kong, Aug. 22-26, 1994, Edited by N.-T. Yu and X.Y. Li: 114-115.

Alain J. P. Alix and Gbassi Pedanou, "Fast Quantitative Determination of Protein Secondary Structure from Raman Amide 1 Band", *Proceedings of the XIVth International Conference on Raman Spectroscopy (ICORS)*, Silver Jubilee, Hong Kong, Aug. 22-26, 1994, Edited by N.-T. Yu and X.Y. Li: 122-123.

Surendra P. Verma, "Effects of Magnetic Fields on the Secondary Structure of Proteins as Determined by Raman Spectroscopy", *Proceedings of the XIVth International Conference on Raman Spectroscopy (ICORS)*, Silver Jubilee, Hong Kong, Aug. 22-26, 1994. Edited by N.-T. Yu and X. Y. Li: 146-147.

A. C. Williams and H. G. M. Edwards, "Identification of Spectroscopic Features in Biological Systems", *Proceedings of the XIVth International Conference on Raman Spectroscopy (ICORS)*, Silver Jubilee, Hong Kong, Aug. 22-26, 1994. Edited by N.-T. Yu and X.Y. Li: 148-149.

Takashi Miura and George J. Thomas, Jr., "Raman Spectroscopy of Telomeric DNA," *Proceedings of the XIVth International Conference on Raman Spectroscopy (ICORS)*, Silver Jubilee, Hong Kong, Aug. 22-26, 1994. Edited by N.-T. Yu and X.Y. Li: 168-169.

P. Piskorz and M. Wojcik, "Low Frequency Raman Spectra of Crystalline Cytosine and Thiocytosine", *Proceedings of the XIVth International Conference on Raman Spectroscopy (ICORS)*, Silver Jubilee, Hong Kong, Aug. 22-26, 1994, Edited by N.-T. Yu and X.Y. Li: 170-171.

Hiedo Takeuchi and Jun Sasamori. "UV Resonance Raman Detection of DNA Structural Changes Induced by Binding of the Peptide SPKK", *Proceedings of the XIVth International Conference on Raman Spectroscopy (ICORS)*, Silver Jubilee, Hong Kong, Aug. 22-26, 1994, Edited by N.-T. Yu and X.Y. Li: 178-179.

Michael S. Field, Ramasamy Manoharan, Yanf Wang, and Ramaachandra R. Dasari, "UV Resonance and NIR Raman Scattering for Tissue Diagnosis and Optical Histochemistry," *Proceedings of the XIVth International Conference on Raman Spectroscopy (ICORS)*, Silver Jubilee, Hong Kong. Aug. 22-26, 1994, Edited by N.-T. Yu and X.Y. Li: 194-195.

Shuming Nie and Nai-Teng Yu, "Raman-based Biomedical Diagnosis at the Molecular Level", *Proceedings of the XIVth International Conference on Raman Spectroscopy (ICORS)*. Silver Jubilee, Hong Kong, Aug. 22-26, 1994, Edited by N.-T. Yu and X.Y. Li: 198-199.

Y. Ozaki, H. Sato, D. Borchman, and A. Mizuno, "Potential of Near-Infrared Raman Spectroscopy in Medical Science", *Proceedings of the XIVth International Conference on Raman Spectroscopy (ICORS)*, Silver Jubilee, Hong Kong, Aug. 22-26, 1994, Edited by N.-T. Yu and X.Y. Li: 202-203.

C. Pang, X.-Y. Li, C. T. Liew, J. C. K. Lee, and N.-T. Yu, "Development of an Optical Fibre-guided Raman Microprobe for the Diagnosis of Cardiovascular Disease: The Study of Atherosclerosis in Human Coronary Artery Tissue", *Proceedings of the XIVth International Conference on Raman Spectroscopy (ICORS)*, Silver Jubilee, Hong Kong, Aug. 22-26, 1994, Edited by N.-T. Yu and X. Y. Li: 204-205.

B. Schrader: S. Keller, T. Lochte, S. Fendel, A. Simon, and J. Sawatzki, "NIR FT Raman Spectroscopy in Medical Diagnostics", *Proceedings of the XIVth International Conference on Raman Spectroscopy (ICORS)*, Silver Jubilee, Hong Kong, Aug. 22-26, 1994. Edited by N.-T. Yu and X.Y. Li: 208-209.

V. V. Tuchin, "Biomedical Applications of Raman Spectroscopy and Its Novel Technologies (Overview)", *Proceedings of the XIVth International Conference on Raman Spectroscopy (ICORS)*, Silver Jubilee, Hong Kong, Aug. 22-26, 1994, Edited by N.-T. Yu and X.Y. Li: 210-211.

M. M. Carrabba, J. W. Hass III, K. M. Spencer, and H. N. Bello,"Applications of Fieldable Fiber Optic Raman Spectroscopy", *Proceedings of the XIVth International Conference on Raman Spectroscopy (ICORS)*, Silver Jubilee, Hong Kong, Aug. 22-26, 1994. Edited by N.-T. Yu and X.Y. Li: 798-799.

Arlene A. Garrison and Madhavi Z. Martin, "Fourier Transform Raman Spectroscopy for Process Analysis", *Proceedings of the XIVth International Conference on Raman Spectroscopy (ICORS)*, Silver Jubilee. Hong Kong, Aug. 22-26, 1994, Edited by N.-T. Yu and X. Y. Li: 804-805.

J. Greve, G. J. Puppels, T. C. Bakker Schut, N. M. Sijjtsema, and C. J. de Grauw, "Raman Microscopy of Cells and Chromosomes", *Proceedings of the XIVth International Conference on Raman Spectroscopy (ICORS)*. Silver Jubilee, Hong Kong, Aug. 22-26, 1994, Edited by N.-T. Yu and X. Y. Li: 858-859.

S.-Y. Yang, T. Ueda, K. Ushizawa, M. Saitoh, M. Tsuboi, "In Situ Raman Microscopy of Photosynthetic Pigments on Thin Layer Chromatography". *Proceedings of the XIVth International Conference on Raman Spectroscopy (ICORS)*, Silver Jubilee. Hong Kong. Aug. 22-26, 1994. Edited by N.-T. Yu and X.Y. Li: 882-883.

N. C. Chaffin, N. W. Daniel, Jr., I. R. Lewis, and P. R. Griffiths, "The Study of Explosives Using Raman Spectroscopy and Feed-forward Neural Networks", *Proceedings of the XIVth International Conference on Raman Spectroscopy (ICORS)*, Silver Jubilee. Hong Kong. Aug. 22-26, 1994. Edited by N.-T. Yu and X.Y. Li: 894-895.

D. T. Durig, S. Qiu, Mengzhang Shen, and J. R. Durig, "Raman Spectra and Conformational Stability of *Trans*-1-Fluoro-2- Butene", *Proceedings of the XIVth International Conference on Raman Spectroscopy (ICORS)*. Silver Jubilee, Hong Kong. Aug. 22-26, 1994, Edited by N.-T. Yu and X.Y. Li: 930-931.

J. Y. Zhou, P. A. Tanner, W. J. Peng, and P. Q. Yang. "Raman Spectroscopy of Fluorescent Samples Using Fluorescent Background Rejection with an Ultrafast Gating Technique", *Proceedings of the XIVth International Conference on Raman Spectroscopy (ICORS)*. Silver Jubilee, Hong Kong, Aug. 22-26, 1994, Edited by N.-T. Yu and X. Y. Li: 1098-1099.

G. J. Thomas, Jr., "Recent Applications of Raman and UVRR Spectroscopy as Probes of Biomolecular Recognition", *Proceedings of The XVII International Conference on Raman Spectroscopy (ICORS 2000)*, Peking University, Beijing, China, Aug. 20-25, 2000, Edited by Shu-Lin Zhang and Bang-fen Zhu: 27-30.

P. Matousek, M. Towrie, W.M. Kwok, C. Ma, D. Phillips, W.T. Toner, and A. W. Parker. "Rejection of Fluorescence from Raman Spectra Using Picosecond Optical Gate", *Proceedings of The XVII International Conference on Raman Spectroscopy (ICORS 2000)*, Peking University, Beijing, China, Aug. 20-25, 2000, Edited by Shu-Lin Zhang and Bang-fen Zhu: 190-191.

M. L. Longmire, Richard C. Wieboldt, and D.E. Pivonka, "In-Situ Monitoring of Combinatorial Reactions by Dispersive Raman Microscopy", *Proceedings of The XVII International Conference on Raman Spectroscopy (ICORS 2000)*, Peking University, Beijing, China, Aug. 20-25, 2000, Edited by Shu-Lin Zhang and Bangfen Zhu: 214.

Yuan Wang, Fenglan Zi, Meili Yang, and Li Liu, "Thin-Layer Chromatography-FT Surface Enhanced Raman Spectroscopic Study on Isomers of Rhynchophyllire in Urcaria Rhynchophylla Jacks Alkaliod", *Proceedings of The XVII International Conference on Raman Spectroscopy (ICORS 2000)*, Peking University, Beijing, China, Aug. 20-25, 2000. Edited by Shu-Lin Zhang and Bang-fen Zhu: 712-713.

E. Koglin and M. J. Schwuger, "Coupling of TLC and SERS Spectroscopy", *Proceedings of The XVII International Conference on Raman Spectroscopy (ICORS 2000)* Peking University, Beijing, China, Aug. 20-25, 2000, Edited by Shu-Lin Zhang and Bang-fen Zhu: 714-715.

X-F Ling, Y-Y Song, W-H Li, Y-Z Xu, L-M Yang, S-F Weng, J. R. Ferraro, X-S Zhou, Z. Xu, R. D. Soloway, and J-G Wu, "FT-Raman Spectroscopic Characterization of Stomach Tissues", *Proceedings of The XVII International Conference on Raman Spectroscopy (ICORS 2000)*, Peking University. Beijing. China, Aug. 20-25, 2000, Edited by Shu-Lin Zhang and Bang-fen Zhu: 786-787.

X-F Ling, W-H Li, Y-Y Song, Z-L Yang, L. Zhang, S-F Weng, Y. Sun, W. G. Fateley. X-S Zhou, and J-G Wu, "FT-Raman Spectra of Normal and Malignant issues ofColon", *Proceedings of The XVII International Conference on Raman Spectroscopy (ICORS 2000)*. Peking University. Beijing, China. Aug. 20-25, 2000, Edited by Shu-Lin Zhang and Bang-fen Zhu: 788-789.

Xiao-Ming Dou and Yukihiro Ozaki, "Biomedical Application of Surface-Enhanced Raman Scattering in Disperse System", *Proceedings of The XVII International Conference on Raman Spectroscopy (ICORS 2000)*. Peking University, Beijing, China. Aug. 20-25, 2000. Edited by Shu-Lin Zhang and Bang-fen Zhu: 1040-1041.

J. Wang, J. K. Snyder, R. Tommasi, H. Marepalli, Q. Tang, and J. Wareing, "Confocal Raman Microsocopy: An Innovative Application in Monitoring Solid Phase Combinatorial Chemistry", *Proceedings of The XVII International Conference on Raman Spectroscopy (ICORS 2000)*. Peking University, Beijing, China, Aug. 20-25, 2000, Edited by Shu-Lin Zhang and Bang-fen Zhu: 1064-1065.

G. D. Sockalingum, P. Lamaze, S. Charanov, M. Pluot, and M. Manfait, "Characterization of Benign and Malignant Human Thyroid Tissue Sections by Raman Microspectroscopy", *Proceedings of The XVII International Conference on Raman Spectroscopy (ICORS 2000)*, Peking University. Beijing. China, Aug. 20-25, 2000, Edited by Shu-Lin Zhang and Bang-fen Zhu: 1070-1071.

M. S. Lee, K. B. Park, D. W. Kim, S. I. Nam, E. S. Min, and J. W. Jang, "Study of Human Skin Tumor and UV-Induced Skin Tumor in Nude Mouse (Balb/cA) by NIR-FT Raman Spectroscopy", *Proceedings of The XVII International Conference on Raman Spectroscopy (ICORS 2000)*, Peking University, Beijing, China, Aug. 20-25, 2000, Edited by Shu-Lin Zhang and Bang-fen Zhu: 1072-1073.

K. Venkata Krishna, K. Raghavendra, Jacob Kurien, Manoj Vengal, Keerthilatha M. Pai, Manna Valiathan, G. Ullas and V. B. Kartha, "Raman Spectroscopy for the Detection of Cancers and Precancers", *Proceedings of The XVII International Conference on Raman Spectroscopy (ICORS 2000)*. Peking University, Beijing, China, Aug. 20-25, 2000, Edited by Shu-Lin Zhang and Bang-fen Zhu: 1086-1087.

Shoji Kaminaka, Hiroya Yamazaki, Toshiaki Ito, Eiichi Kohda, and Hiro-o Hamaguchi, "1064-nm Excited Near-Infrared Raman Spectroscopy for Cancer Diagnosis of Human Tissues", *Proceedings of The XVII International Conference on Raman Spectroscopy (ICORS 2000)*, Peking University, Beijing, China, Aug. 20-25, 2000, Edited by Shu-Lin Zhang and Bang-fen Zhu: 1090-1091.

R. Erckens et al., "Raman Spectroscopy for Non-Invasive Characterization of Ocular Tissue: Potential for Detection of Biological Molecules," *J. Raman Spectroscopy*, vol. 28, pp. 293-299, 1997.

I. R. Paeng et al., "Resonance Raman studies of Mono-and Difluoro-5,10,15,20-tetrakis(pentafluorophenyl)porphyriniron(III)", *J. Raman Spectroscopy*, vol. 28, pp. 229-234, 1997.

N. Kline et al., "Raman Chemical Imaging of Breast Tissue", *J. Raman Spectroscopy*, vol. 28, pp. 119-124, 1997.

M. Shim et al., "Development of an In Vivo Raman Spectroscopic System for Diagnostic Applications", *J. Raman Spectroscopy*, vol. 28, pp. 131-142, 1997.

C. Otto et al., "Applications of Micro-Raman Imaging in Biomedical Research", *J. Raman Spectroscopy*, vol. 28, pp. 143-150, 1997.

A. Torreggiani et al., "Involvement of Lysine and Tryptophan Side-Chains in the Biotin-Avidin Interactions", *J. Raman Spectroscopy*, vol. 28, pp. 23-27, 1997.

K. Tseng et al., "Identification and Structural Elucidation of Lectin-Binding Oligosaccharides by Bioaffinity Matrix-Assisted Laser Desorption/Ionization Fourier Transform Mass Spectrometry (MALDI-FT MS)", *Anal. Chem.*, vol. 73, pp. 3556-3561, 2001.

E. Golet et al., "Trace Determination of Fluoroquinolone Antibacterial Agents in Urban Wastewater by Solid-Phase Extraction and Liquid Chromatography with Fluorescence Detection", *Anal Chem.*, vol. 73, pp. 3632-3638, 2001.

B. Schrader et al., "Non-destructive NIR-FT-Raman Spectroscopy of plant and animal tissues, of food and works of art", *Talanta*, vol. 53, pp. 35-45, 2000.

P. Taddei et al., "Vibrational spectroscopy of polymeric biomaterials", *J. Raman Spectroscopy*, vol. 32, pp. 619-629, 2001.

Y. Mori, "Introductory studies on the growth and characterization of carotenoid solids: an approach to carotenoid solid engineering", *J. Raman Spectroscopy*, vol. 32, p. 543-550, 2001.

D. Murgida et al., "Resonance Raman spectroscopic study of the neutral flavin radical complex of DNA photolyase from *Escherichia coli*," *J. Raman Spectroscopy*, vol. 32, pp. 551-556, 2001.

S. Hashimoto et al., "Structural study on acid-induced unfolding intermediates of myoglobin by using UV Resonance Raman scattering from tryptophan residues", *J. Raman Spectroscopy*, vol. 32, pp. 557-563, 2001.

G. Smulevich et al., "Resonance Raman spectra and transform analysis of anthracyclines and their complexes with DNA", *J. Raman Spectroscopy*, vol. 32, pp. 565-578, 2001.

S. Lee et al, "Temperature-dependent Raman and IR spectra of nucleosides. Part I—adenosine", *J. Raman Spectroscopy*, vol. 31, pp. 891-896, 2000.

G. Sarata et al., "Nanosecond time-resolved Resonance Raman and absorption studies of the photochemistry of chlorpromazine and related phenothiazine derivatives", *J. Raman Spectroscopy*, vol. 31, pp. 785-790, 2000.

W. Wang et al., "Application of femtosecond coherence spectroscopy of the observation of nuclear motions in heme proteins and transparent solutions", *J. Raman Spectroscopy*, vol. 31, pp. 99-105, 2000.

X. Zhao et al, "Kinetics of hemoglobin allostery from time-resolved UV resonance Raman spectroscopy: effect of chemical cross-link", *J. Raman Spectroscopy*, vol. 31, pp. 349-352, 2000.

X. Zhao et al., "Time-resolved Raman spectroscopy with a tunable Ultraviolet Kilhertz Nanosecond Laser", *J. Raman Spectroscopy*, vol. 30, pp. 773-776, 1999.

T. Vo-Dinh et al., "Surface-Enhanced Raman Scattering (SERS) Method and Instrumentation for Genomics and Biomedical Analysis", *J. Raman Spectroscopy*, vol. 30, pp. 785-793, 1999.

R. Clarke et al., "Low-Resolution Raman Spectroscopy: Instrumentation and Application in Chemical Analysis", *J. Raman Spectroscopy*, vol. 30; pp. 827-832, 1999.

L. Quaroni et al., "The Nitro Stretch as a Probe of the Environment of Nitrophenols and Nitrotyrosines", *J. Raman Spectroscopy*, vol. 30, pp. 537-542, 1999.

X. Dou et al., "NIR SERS Detection of Immune Reaction on Gold Colloid Particles Without Bound/Free Antigen Separation", *J. Raman Spectroscopy*, vol. 29, pp. 739-742, 1998.

P. Carey, "Resonance Raman Labels and Raman Labels", *J. Raman Spectroscopy*, vol. 29, pp. 861-868, 1999.

P. Carey, "Raman Spectroscopy in Enzymology: the First 25 years", *J. Raman Spectroscopy*, vol. 29, pp. 7-14, 1998.

S. Overman et al., "Novel Vibrational Assignments for Proteins From Raman Spectra of Viruses", *J. Raman Spectroscopy*, vol. 29, pp. 23-29, 1998.

M. Famulok et al., "Nucleic Acid Aptamers-From selection In Vitro to application In Vivo", *Acc. Chem. Res.*, vol. 33, pp. 591-599, 2000.

S. Gite et al., "Ultrasensitive Fluorescence-Based Detection of Nascent Proteins in Gels", *Analytical Biochemistry*, vol. 279, pp. 218-225, 2000.

Y. Huang et al., "Mechanism of Ribose 2'-Group Discrimination by an RNA Polymerase", *Biochemistry*, vol. 36, pp. 8231-8242, 1997.

L. Brieba et al., "Roles of Histidine 784 and Tyrosine 639 in Ribose Discrimination by T7 RNA Polymerase", *Biochemistry*, vol. 39, pp. 919-923, 2000.

V. Gorelik et al, "Raman scattering in hydrocarbon and fluorocarbon zigzag structures," *Proc. SPIE Photonics East 2000, Boston, MA*.

C. Sharts et al., "Detection of carbon-fluorine bonds in organofluorine compounds by Raman spectroscopy using a copper-vapor laser", *Proc. SPIE Photonics East, Boston, MA* 1998.

M. Tsuboi, "Forward to the Special Issue on Raman Spectroscopy of Proteins", *J. Raman Spectroscopy*, vol. 29, pp. 3-5, 1998.

F. Oehlenschläger et al., "Detection of HIV-1 RNA by nucleic acid sequence-based amplification combined with fluorescence correlation spectroscopy", Proc. Nat. Acad. Sci., USA. Biochemistry, vol. 93, pp. 12811-12816, Nov. 1996.

J. Politz et al., "Intranuclear diffusion and hybridization state of oligonucleotides measured by fluorescence correlation spectroscopy in living cells", Proc. Nat. Sci., USA, Biochemistry, vol. 95, pp. 6043-6048, May 1998.

Celia M. Henry, "Pharmacogenomics," Chemical & Chemical Engineering News, Vo. 79, pp. 37-42, Aug. 13, 2001.

G. Kalinkova, "Infrared spectroscopy in pharmacy," Vibrational Spectroscopy, vol. 19, pp. 307-320, 1999.

M. Haddach, J. Sapienza, and C. M. Sharts, "Synthesis of [2-$^{14}$C]Perfluorohexane", J. Labelled Compounds and Radiopharmaceuticals, vol. 42, pp. 227-231, 1999.

Organofluoorine Chemistry: Principles and Commercial Applications, Edited by R. E. Banks, B. E. Smart, and J. C. Tatlow, Topics in Applied Chemistry Series, Plenum Press, New York, 1994, p. 379 in section 16.2.2.2, "Molecular Weight Control," of Chapt. 16 "Fluoroelastomers." by Anestis L. Logothetis; p. 455 in section 20.6.7, "Mass Spectrometry," of Chapt. 20 "Perfluoropolyethers (PFPEs) from Perfluoroolefin Photooxidation," by Dario Sianesi, Guiseppe Marchionni. and Ralph J. De Pasquale (On the use of fluoropoiymer markers for mass spectorscopy); pp. 50 1-54 1 of Chapt. 24, "Uses of Fluorine in Chemotherapy," by Philip Neil Edwards; pp. 543-554 in Chapt. 25, "Fluorinated inhalation anesthetics," by Donald F. Halpern; p. 565 of section 26.5.4, "Effects on tissue biochemistry," p. 570 of section 26.6.4, "Contrast Media and Diagnostic Imaging," in Chapt. 26, "Properties and Biomedical Applications of Perfluorochemicals and Their Emulsions," by Kenneth C. Lowe.

K. Johns and G. Stead, "Fluoroproducts—the extremophiles", J. Fluorine Chemistry, vol. 104, pp. 5-18, 2000.

S. Bowman, "The contribution of fluorinated compounds to the world of human pharmaceuticals", Proceedings of Conf. on Fluorinated Bio-Active Compounds in Agricultural and Medical Fields, Brussels, Belgium, Sep. 13-15, 1999.

A. Osborne et al., "Biotransformations to Generate Fluorinated Analogues of Shikimate Pathway Intermediates", Paper 13, Proc. Conf. on Fluorinated Bio-Active Compounds in Agricultural and Medical Fields, Brussels, Belgium Sep. 13-15, 1999.

B. Key et al., "Fluorinated Organics in the Biosphere," Environmental Science & Technology, vol. 31, No. 9, pp. 244502454, 1997.

Schwille et al., "Analyzing single protein molecules using optical methods," Curr. Opinion in Biotech., vol. 12, pp. 382-386, 2001.

T. de Groot et al., "Synthesis of 1-[$^{18}$F]fluorodeoxyglucose: an unexpected rearrangement in the reaction of 2-O-methanesulfonyl-β-D-mannopyranose with [$^{18}$F]fluoride." J. Labelled Compounds and Radiopharmaceuticals, vol. 42, pp. 147-157, 1999.

W. Freist et al., "Accuracy of Protein Biosynthesis: Quasi-species Nature of Proteins and Possibility of Error Catastrophes", J. Theor. Biol., Article No. jt980672, vol. 192, pp. 19-38, 1998.

A. Isaksson et al., "Accessing genomic information: alternatives to PCR", Curr. Opinion in Biotech., vol. 10, pp. 11-15, 1999.

H. Iida et al., "Rotational recognition of nucleic acid sequences", Curr. Opinion in Biotech., vol. 10, pp. 29-33, 1999.

J. Banér et al., "More keys to padlock probes: mechanism for high-throughput nucleic acid analysis", Curr. Opinion in Biotech., vol. 12, pp. 11-15, 2001.

J. Hoheisel et al., "Analytical Biotechnology", Curr. Opinion in Biotech., vol. 12, pp. 9-10, 2001.

B. Schweitzer et al., "Combining nucleic acid amplification and detection", Curr. Opinion in Biotech., vol. 12; pp. 21-27, 2001.

F. Scheller et al., "Research and Development of Biosensors", Curr. Opinion in Biotech., vol. 12, pp. 35-40, 2001.

D. Blohm et al., "New developments in microarray technology", Curr. Opinion in Biotech., vol. 12, pp. 41-47, 2001.

N. L. van Berkum et al., "DNA microarrays raising the profile", Curr. Opinion in Biotech., vol. 12, pp. 48-52, 2001.

S. Tillib et al., "Advances in the analysis of DNA sequence variations using oligonucleotide microchip technology," Curr. Opinion in Biotech., vol. 12, pp. 53-58, 2001.

E. Fung et al., "Protein biochips for differential profiling", Curr. Opinion in Biotech., vol. 12, pp. 65-69, 2001.

K. Slater, "Cytotoxicity tests for high-throughput drug discovery", Curr. Opinion in Biotech., vol. 12, pp. 70-74, 2001.

S. D'Auria et al., "Enzyme fluorescence as a sensing tool: new perspectives in biotechnology", Curr. Opinion in Biotech., vol. 12, pp. 99-104, 2001.

J. Kyranos et al., "High-throughput high-performance liquid chromatography/mass spectrometry for modern drug discovery" Curr. Opinion in Biotech., vol. 12, pp. 105-111, 2001.

M. Cockett et al., "Applied genomics: integration of the technology within pharmaceutical research and development", Curr. Opinion in Biotech., vol. 11, pp. 602-609, 2000.

M. Olsen et al., "High-throughput screening of enzyme libraries," Curr. Opinion in Biotech., vol. 11, pp. 331-337, 2000.

M. Chalmers et al., "Advances in mass spectrometry for proteome analysis," Curr. Opinion in Biotech., vol. 11, pp. 384-390, 2000.

K. Nauta et al., "Probing the Structure of Metal Cluster-Adsorbate Systems with High-Resolution Infrared Spectroscopy", Science, vol. 292, p. 481-484, Apr. 20, 2001.

C. B. Epstein et al., "Microarray technology—enhanced versatility, persistent challenge", Curr. Opinion in Biotech., vol. 11, pp. 36-41, 2000.

S. Gygi et al., "Measuring gene expression by quantitative proteome analysis", Curr. Opinion in Biotech., vol. 11, pp. 396-401, 2000.

P. S. Lee et al., "Genomic Analysis" Curr. Opinion in Biotech., vol. 11, pp. 171-175, 2000.

M. Dutt et al., "Proteomic analysis", Curr. Opinion in Biotech., vol. 11, pp. 176-179, 2000.

J. L. West et al., "Applications of nanotechnology to biotechnology", Curr. Opinion in Biotech., vol. 11, pp. 215-217, 2000.

P. Hensley, et al., "Analytical Biotechnology: sorting needles and haystacks", Curr. Opinion Biotech., vol. 11, pp. 9-12, 2000.

Steven A. Sundberg, "High-throughput and ultra-high-throughput screening: solution- and cell-based approaches", Curr. Opinion in Biotech., vol. 11, pp. 47-53, 2000.

A. Svensson et al., "Preparation of Fluorinated Linkers: Use of $^{19}$F NMR Spectroscopy to Establish Conditions for Solid-Phase Synthesis of Pilicide Libraries", J. Comb. Chem., vol. 2, pp. 736-748, 2000.

R. Perez et al., "A comparison of Surface Enhanced Raman Spectroscopic and Fluorimetric Detection of the Phenothiazine Derivative Trifluoperazine and its Photooxidation Products", Analytical Chimica Acta, vol. 269, pp. 197-204, 1998.

B. Olsen et al., "Determination of fluoxetine hydrochloride enantiomeric excess using High-performance liquid chromatography with chiral stationary phases", J. Pharm. and Biomed. Anal., vol. 17, pp. 623-630, 1998.

S. Khateeb et al., "Stability-indicating methods for the spectrophotometric determination of norfloxacin," J. Phar. And Biomed. Anal., vol. 17, pp. 829-840, 1998.

Herida R. N. Marona et al, "Spectrophotometric determination of sparfloxacin in pharmaceutical formulations using bromothymol blue", J. Pharm. And Biomed. Anal., vol. 26, pp. 501-504, 2001.

S. Böttcher et al., "An HPLC assay and a microbiological assay to determine levofloxacin in soft tissue, bone, bile and serum", J. Pharm. And Biomed. Anal., vol. 25, pp. 197-203, 2001.

J. Novakovic et al., "An HPTLC method for the determination and the purity control of ciprofloxacin HC1 in coated tablets", J. Pharm. And Biomed. Anal., vol. 25, pp. 957-964, 2001.

A. El-Gindy et al., "Spectrophotometric determination of trifluoperazine HC1 and isopropamide iodide in binary mixture using second derivative and second derivative of the ration spectra methods", J. Pharm. And Biomed. Anal., vol. 26, pp. 203-210, 2001.

R. D. Meyer et al., "Visualization of data", Curr. Opinion in Biotech, vol. 11, pp. 89-96, 2000.

Silicon & Fluorine News, Issue 17, pp. 28-31, May 2000.

Silicon & Fluorine News, Issue 16, pp. 1-36, Mar. 2000.

G. Withers et al., "Fluorinated carbohydrates as probes of enzyme specificity and mechanism", Fluorinated Carbohydrates: Chemical and Biochemical Aspects, Chapter 5, pp. 59-77, edited by N. F. Taylor, ACS Symposium Series 374. ACS 1988.

C. Glaudemans et al, "Deoxufluoro carbohydrates as probes of binding sites of monoclonal antisaccharide antibodies", Fluorinated Carbohydrates: Chemical and Biochemical Aspects, Chapter 6, pp. 78-1 08, edited by N. F. Taylor, ACS Symposium Series 374. ACS 1988.

W. S. Guy, "Organic fluorocompounds in human plasma: prevalence and characterization", *Biochemistry Involving Carbon-Fluorine Bonds*, Chapter 7, pp. 117-134, edited by R. Filler, ACS Symposium Series 28, ACS 1976.

John Ferraro and Kazuo Nakmoto, *Introductory Raman Spectroscopy*, Academic Press, pp. 53-59, 1994.

T. J. Sendera (Motorola Life Sciences), "Analysis of gene expression in carbon tetrachloride-treated rat livers using Motorola bioarray technology", *Drug Discovery Technology 2002 Conference*, Stuttgart, Germany, Apr. 16-16, 2002.

Kaminaka. et al., "Near Infrared Raman spectroscopy of human lung tissues: possibility of molecular-level cancer diagnosis", *Journal of Raman Spectroscopy*, (vol. 32, pp. 139-141, 2001.

J. Wachter, et al., "Monitoring polymorphic transformations in real-time", *Raman Review*, pp. 1-4, Spring 2000

M. G. Hansen et al., Real-time monitoring of industrial polymers, *Raman Review*, pp. 1-4, Mar. 1998.

P. R. Carey et al., "Urokinase inhibitor screening by Raman spectroscopy", *Raman Review*, Issue 1, pp. 1-4, 2002.

C. Frank (Procter &Gamble Pharmaceuticals), "Raman analysis in pharmaceuticals", *Raman Review*, pp. 1-4, Sep. 1998.

N. P. Weston et al (Pfizer. Inc.), "Tracking Grignard reactions in real time", *Raman Review*, Issue 2, pp. 1-4, 2001.

J. Andrew et al. (Unilever Research), Faster chemical mapping of emulsions, *Raman Review*, pp. 1-4, Winter, 2001.

J. Lambert, et al., "Measurement of Physiologic glucose levels using Raman spectroscopy in a Rabbit Aqueous Humor Model", web publication, http://www.ieee.org/organizations/pubs/newsletters/leos/apr98/aqueoushumor.html; Jul. 21, 2002, 6 pages.

Wheeler, "PET uncovers first signs of Alzheimer 's disease", *Biophotonics International*, pp. 23-24, Jun. 2002.

N. Utley (Enigma Marketing Research), "Fluorine and the agrochemical market", *Proceedings of a Conference on Fluorinated Bio-Active Compounds in the Agricultural and Medical Fields*, Brussels, Belgium, Sep. 13-15, 1999.

U. Utzinger, et al., (University of Texas) "Fiber optic probes in optical spectroscopy, clinical applications", *Electronic Spectroscopy Applications*, pp. 512-528, Academic Press, 1999.

R. Lewis, "Microarrays take on bioterrorism", *Biophotonics International*, pp. 40-41, Jan./Feb. 2002.

D. Ott, "Two-photon microscopy reveals tumor development", *Biophotonics International*, pp. 46-48, Jan./Feb. 2002.

V. Couling et al., Ultraviolet Resonance Raman study of drug binding in dihydrofolate reductase, gyrase and catechol O-methyltransferase, *Biophysical Journal*, vol. 75, pp. 1097-1106, Aug. 1998.

V. Valge-Archer, "Developing monoclonal antibodies like drugs", *Proceedings of Drug Discovery Technology Conference*, Stuttgart, Apr. 16-18, 2002, 15 pages.

R. Kozlowski (at Sense Proteomics, Ltd.), "The use of arrays of functional proteins in the drug discovery process", *Proceedings of Drug Discovery Technology Conference*, Stuttgart, Apr. 16-18, 2002, 14 pages.

Description of photoaptamers at website: http://www.somalogic.com/science/photoselex.html/aptamers.html., Apr. 8, 2002.

U. Heinemann et al., "High -throughput three-dimensional protein structure determination", *Current Opinion in Biotechnology*, vol. 12, pp. 348-354, 2001.

Tuan Vo-Dinh, et al., "Cancer gene detection using surface-enchanced Raman scattering (SERS)", *J. Raman Spectroscopy*, vol. 33, pp. 511-516, 2002.

Takashi Miura, Chiaki Yamamiya, Miho Sasaki. Kiyoko Suzuki, and Hideo Takeuchi, "Binding mode of Congo Red to Alzheimer 's amyloid P-peptide studies by UV Raman spectroscopy", *J. Raman Spectroscopy*, vol. 33, pp. 530-535, 2002.

James L. Lambert, John Michael Morookian, Shannon J. Sirk, and Mark S. Borchert, "Measurement of aqueous glucose in a model anterior chamber using Raman spectroscopy", *J. Raman Spectroscopy*, vol. 33, pp. 524-529, 2002.

Bayden R. Wood and Don McNaughton, Raman excitation wavelength investigation of single red blood cells in vivo, *J. Raman Spectroscopy*, vol. 33, pp. 517-523, 2002.

Christopher J. Barbosa, Frederic H. Vaillancourt, Lindsay D. Eltis, Michael W. Blades, and Robin F. B. Turner, "The power distribution advantage of fiber-optic coupled ultraviolet resonance Raman spectroscopy for bioanalytical and biomedical applications", *J. Raman Spectroscopy*, vol. 33, pp. 503-510, 2002.

C. Clifton Ling, John Humm, Steven Larson, Howard Amols, Zvi Fuks, Steven Leibel, and Jason A. Koutcher, "Towards multidimensional radiotherapy (MD-CRT): Biological imaging and biological conformality", *Int. J. Radiation Oncology Biol. Phys.*, vol. 47, No. 3, pp. 551-560, 2000.

J. Clarkson, et al., "Ultraviolet Resonance Raman Study of the Streptavidin Binding of Biotin and 2-Imminobiotin" *Biopolynzers (Biospectroscopy)*, 2001, , 307-3 14.

W. Wattanatorn. H. L. McLeod, J. Cassidy, and K. E. Kendle, "High-performance liquid chromatographic assay of 5-fluorouracil in human erythrocytes, plasma, and whole blood," *J. Chromatogrpahy B*, 1997, 692: 233-237.

V. Gorelik et al, "Raman and Fluorescence Spectra of Fluoroorganic Compounds", *Proc. SPIE Photonics East*, Boston, MA, 3855: 16-27, 1999.

Gorelik, et al., "Determination of the length of zigzag chain molecules from Raman spectra", *Proceedings of the XVIIth International Conference on Raman Spectroscopy (ICORS)*, Beijing, China, Aug. 20-25, 2000.

* cited by examiner

Fluorouracil
(5-FU)
anticancer drug

Fluoxetine (Prozac)
antidepressant drug

Perflubron     (Oxygent)
Blood Substitute  (Liquivent)

Flurazepam
(Dalmane)
pain killer
tranquilizer

Diflubenzuron     (insecticide)

Fluometuron
(herbicide)

3-Trifluoromethyl-
4-nitrophenol    (lampricide)

Compound 1080
(pesticide) [natural product]

Tefluthrin        PPC 993 (ICI)        Force
(insecticide)

Benzene [$C_6H_6$]

Hexafluorobenzene [$C_6F_6$]

1,3,5-(tris)-Trifluorommethyl-benzene [$C_9F_9H_3$]

Pentafluoropyridine [$C_6F_5N$]

$CF_3CF_2CF_2CF_2CF_2CF_2CF_2CF_2Br$
1-Bromoperflucrooctane [$C_8F_{17}Br$]
Perflubron (blood substitute)

Perfluorotripropylamine [$C_9F_{21}N$]

1-Perfluorodecanoic Acid [$C_{10}F_{21}COOH$]

Perfluorodecalin

Fluoxetine (Prozac) antidepressant drug

DETECTION OF CARBON HALOGEN BONDS

CROSS REFERENCE TO RELATED APPLICATIONS

This application is a continuation-in part of U.S. Patent Application Ser. No. 09/947,312, filed Sept. 5, 2001, now U.S. Patent No. 6,445,449, which is a continuation of U.S. Patent Application Serial No. 09/343,148, filed Jun. 29, 1999, now U.S. Patent No. 6,307,625, which claims benefit of priority to U.S. Provisional Patent Application No. 60/09 1,090, filed Jun. 29, 1998, and U.S. Provisional Patent Application No. 60/138,643, filed Jun. 10, 1999.

BACKGROUND

Quantitative and qualitative analysis of compounds and molecules is an important task. One type of analysis is the detection of chemical and biological compounds using, for example, radioactive labeling. Chemical compounds and biological molecules are radioactive labeled to form tracers. The radioactive compounds, molecules, and their metabolites are then followed through the body and observed for emitted radioactivity. This type of detection, however, has limited sensitivity and requires expensive safety and precautionary measures.

DESCRIPTION OF DRAWINGS

Like reference numbers and designations in the various drawings indicate like elements.

DETAILED DESCRIPTION

Figure 1:
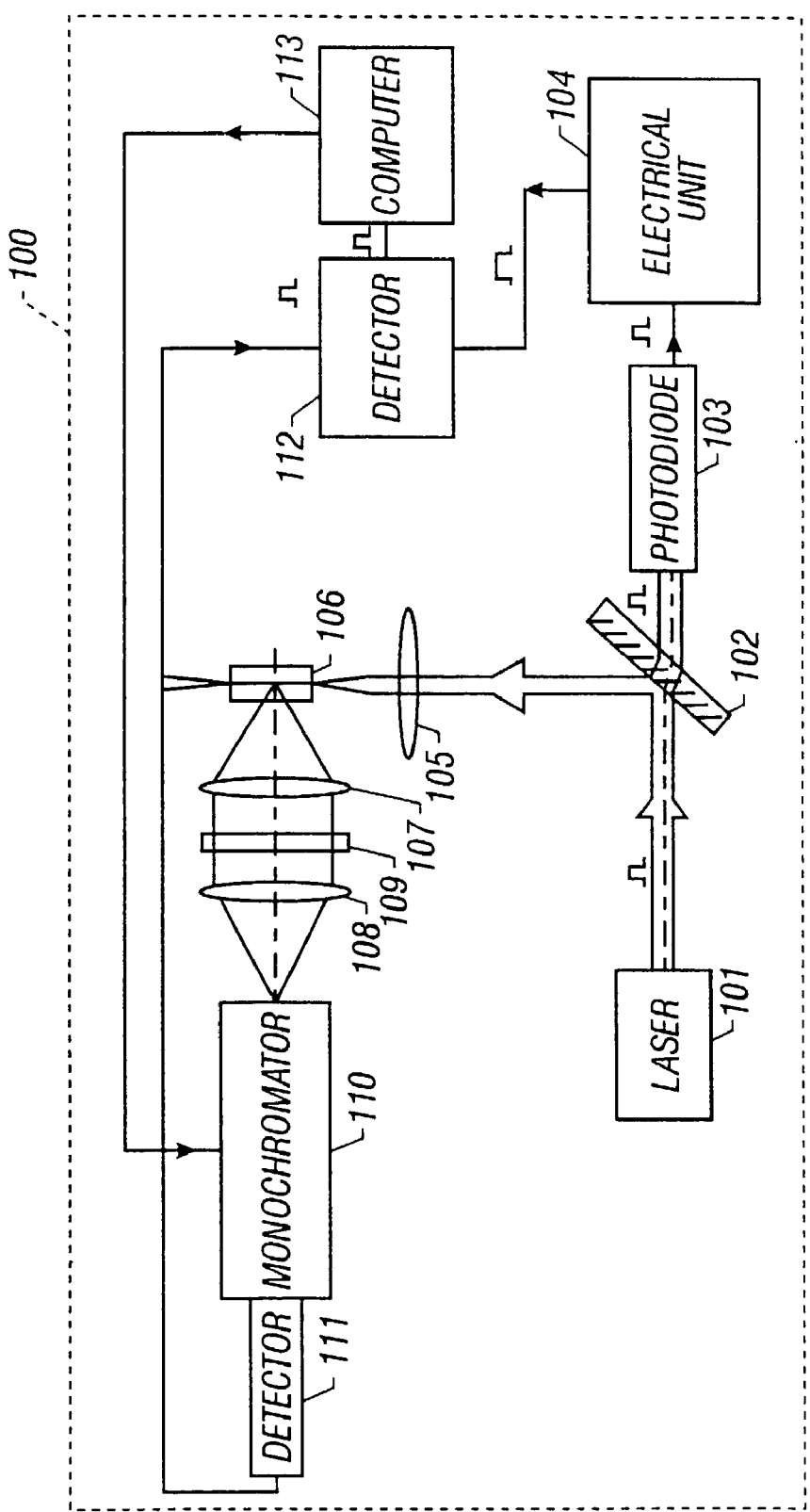
FIG. 1 is a schematic drawing of a Raman spectrometer in accordance with an embodiment.

FIG. 1 illustrates a Raman instrument 100 that includes a metal-vapor laser. Suitable lasers include a copper-vapor or a gold-vapor laser. The Raman instrument 100 also includes a mirror 102 with dielectric and highly reflective coating to efficiently reflect a generated laser radiation, and a photodiode 103 for collecting a laser radiation. The instrument 100 also includes an electronic unit 104 (e.g., a stroboscopic generator) and a condensing lens 105 that focuses a laser beam on the sample 106 to be analyzed (the sample 106 not being a component of the apparatus). Condensing lenses 107 and 108 are used to focus beams on the spectrometer slit after passing through the sample 106 and an absorbance filter 109 is used to pass a Raman emission signal (secondary radiation). The Raman instrument 100 also includes a single or double monochromator spectrometer 110, a detector of secondary radiation 111 (e.g., a photomultiplier), a pulse recording system 112 controlled by the stroboscopic system 104, and, optionally, a computer 113 for data collection and processing and for management of the spectrometer 110. The spectrophotometer 110 may be a single, double, or triple monochomator for the visible and ultraviolet region of the spectra, equipped with a photomultiplier 111 and sensitive photon-counting detector system 112. The high energy laser 101 pulses irradiate the fluoroorganic sample 106 and also activate a device 104, to form a strobe-impulse used to synchronize the pulse recording system 112. Samples may be placed into cylindrical quartz cuvettes having parallel windows (not shown). Raman spectra are observed at 90° with respect to the incident pulse by using a single or double monochromator 110 with a single channel detection. When irradiated, the sample 106 emits pulsed Raman radiation and also scatters part of the incident Raman pulse. The absorbance filter 109 removes scattered radiation and passes the pulsed Raman radiation to the spectrometer 110. Signals are photomultiplied and sent to a synchronized pulse recording system 112. To obtain ultraviolet radiation (255.3 nm; 271.2 nm and 289.1 nm), a doubling crystal, such as $BaB_2O_4$, or a tripling crystal, can be used.

A suitable laser 101 that can be used with the apparatus is designed and manufactured at Lebedev Institute of Physics (Russian Academy of Sciences, Moscow, Russia). One such laser is a 3-watt or 10-watt Russian-designed air-cooled copper-vapor laser manufactured by the Lebedev Physics Institute. A stroboscopic generator 104 that can be used with the instrument 100 is also designed and manufactured at Lebedev Institute of Physics (Russian Academy of Sciences, Moscow, Russia). The spectrophotometer 110 can be any standard monochomator or a commercial product such as a Jobin-Yvon U1000 double monochromator Raman spectrometer. The spectrophotometer may be modified to permit observation of the spectra of fluoroorganic compounds as shown in FIGS. 2-8, below. The optical filter can be a GUI-6 absorption optical filter. The monochromator can be an MSD-2 monochromator. The photomultiplier 111 can be an FEU-106 photomultiplier.

Excitation light emitted by the metal-vapor laser 101 is attenuated by an optical absorption filter 109 placed in front of a sample 106. The filter 106 is used to limit the excitation light going to the sample. In the spectral range 200-400 nm, the filter 109 can be an ultraviolet filter, such as a GUI-6. In the range 360-480 nm, the filter can be a blue wavelength filter, such as a BG-12. GUI-6 and BG-12 filters are commercially available from AGFA. The luminescence spectra normalized to allow for the transmission coefficient of the relevant filter 109.

A pulsed metal-vapor laser 101 has significant advantages over continuous wave argon or helium-neon lasers. The pulsed signal generates significantly less photodecomposition and permits the simple elimination of primary fluorescence. Further, laser 101 is significantly cheaper than Raman spectrometers that use longer wavelength excitation lasers, particularly to the Nd:YAG laser at 1064 nm, to eliminate fluorescence. This is because the longer wavelength lasers require expensive CCD signal detectors that significantly increase cost.

The metal-vapor laser 101 can provide about 16 times the signal of commercial Nd:YAG laser Raman spectrometers. Because the Raman vibrational scattering emissions are detected during a narrow time internal ("gate") approximately equal to the laser pulse duration ($10^{-8}$ sec), fluorescence is eliminated. Pulsed techniques also give enhanced sensitivity.

Thus, the intense characteristic Raman band of the symmetric vibrational normal mode of carbon-fluorine bond or groups in the Raman spectra of organic compounds, excited by the pulse laser source, can be established. For example, to achieve optimal excitation of a C—F band, the exposure of the sample to the excitation source must be 10-8 seconds or more. The Raman spectrum is measured within the above exposure period. Therefore, the Raman spectra is not affected by fluorescence.

Using the Raman instrument 100, an emitting signal of a carbon-fluorine bond normal mode (vibrational) or carbon-fluorine group normal mode (rotational), which occurs within a narrow frequency range, is very strong with recognizable narrow band widths. The term "normal mode" refers to the symmetric vibrational process of excited atoms. The radiation characteristic of carbon-fluorine bonds may be detected in the 500-800 $cm^{-1}$ region. Other radiation in the 950-1400 $cm^{-1}$ region commonly associated with fluoroorganic compounds can also be observed.

The published frequency range for carbon-fluorine bond infrared absorption is 1000 $cm^{-1}$ to 1400 $cm^{-1}$ These other bands are useful and can be used to confirm carbon-fluorine groups detected by the instrument. However, these infrared absorptions are subject to interference by other functional groups in the fluoroorganic compound, as discussed above.

A type of carbon-fluorine bond can also be identified. The vibration of fluorine against carbon (such C—F vibrations occur in the infrared at 1000-1400 $cm^{-1}$) is not measured. Rather, deviations from the totally symmetric Raman active mode of the groups (such as the carbon-fluorine group in the aromatic compound hexafluorobenzene or the trifluoromethyl group in trifluoromethylated compounds, such as 1,3, 5-tris(trisfluoromethyl)benzene), are detected. Changes in the polarization of carbon-fluorine groups as part of the total molecular vibrational normal modes may also be detected.

The laser 101 is adaptable to frequency doubling to give a strong signal in the ultraviolet (UV) at about 255.4 nm. UV signals at 272 nm and 289 nm are also available. Irradiation of samples in the ultraviolet allows the observation of resonance Raman spectra which have signals approximately $10^4$ to $10^5$ stronger (10,000-100,000 times stronger) than normal Raman signals. Resonance Raman signals means detection of compounds containing carbon-fluorine bonds at the parts per billion (ppb) level. Frequency doubling of the wavelengths is observed for both the copper-vapor laser and the gold-vapor laser.

Figure 6:
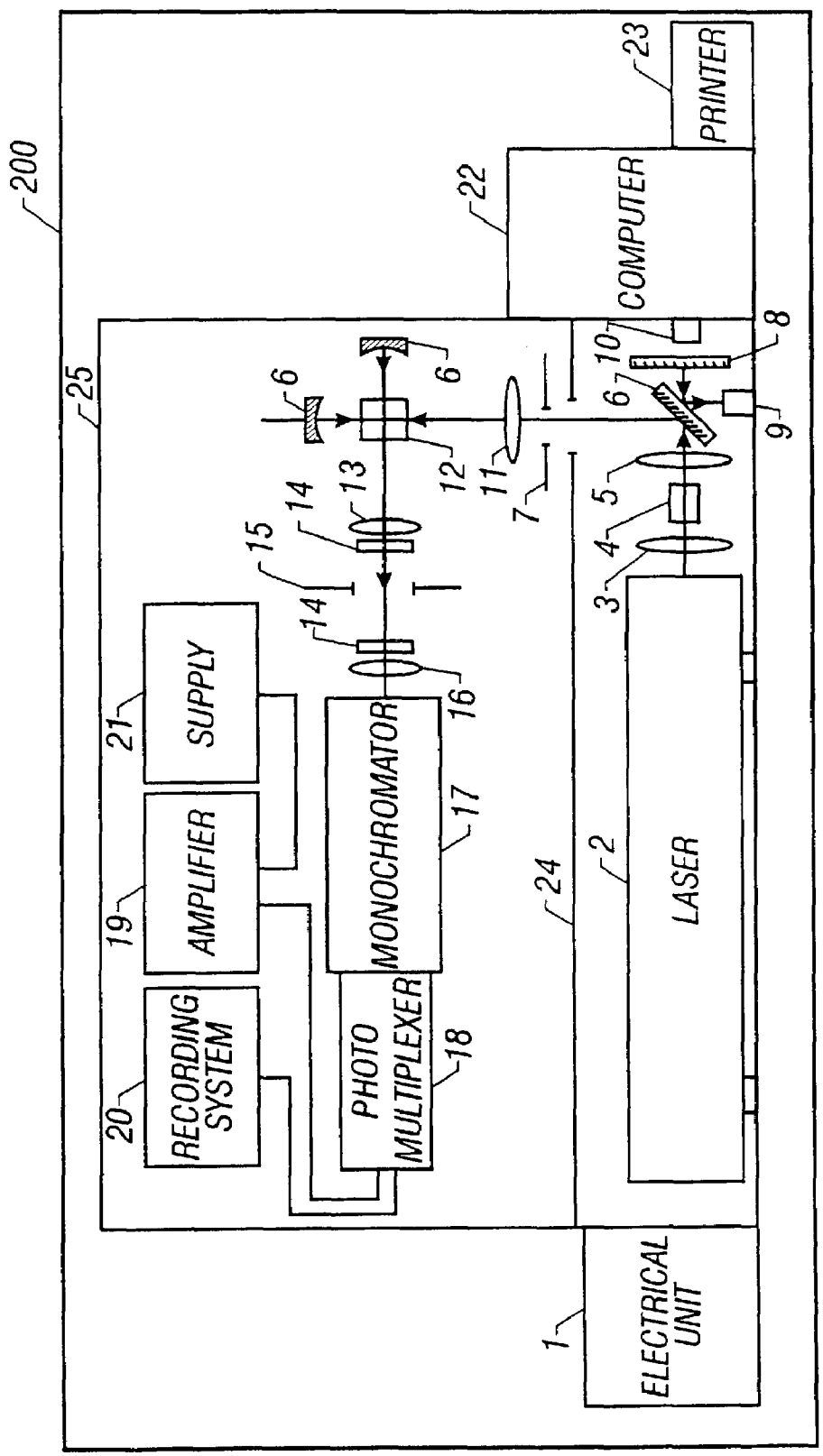
FIG. 6 is a schematic drawing of a resonance Raman spectrometer in accordance with an embodiment.

FIG. 6 is a schematic drawing of a Raman spectrometer 200 as adapted for resonance Raman spectroscopy. The Raman spectrometer 200 is similar to the Raman instrument 100 in FIG. 1. However, the spectrometer 200 includes a non-linear frequency doubling crystal 4. The frequency doubling crystal can be constructed of barium borate. The spectrometer 200 may also include additional filters 14.

The doubled frequencies, expressed as wavelengths, for a copper-vapor laser may be about 255 nm and 289 nm. A combination band at 272 nm may also be useful. For a gold-vapor laser, the doubled frequency wavelength is about 314 nm. Almost all of the compounds of TABLE 1 below have aromatic rings and are almost certain to give significant enhancement of the resonance Raman emission signal due to the high self-absorbance of the aromatic ring structures. Aromatic rings absorb energy at frequencies similar to those emitted (self-absorption). Using a frequency doubling crystal, the frequency may be shifted from 510.6 nm to 255.3 nm where it is absorbed.

The spectrometer 200 permits a significant suppression of dark current and environmental noise, and also increases sensitivity. The background of continuous fluorescence can be suppressed by using a strobe-impulse. The strobe-impulse is synchronized with a laser source pulse and "opens" a detection system for only about $10^{-8}$ sec. This period corresponds to the duration of the laser pulse. As a result, the spectrometer 200 permits a low level detection of fluoroorganic compounds.

A Raman band that is characteristic of carbon-fluorine bonds can be found in the range 540 cm$^{-1}$ to 785 cm$^{-1}$, based on experimental observations. For estimation purposes, a range of 500-800 cm$^{-1}$ is reasonable.

Figure 9:
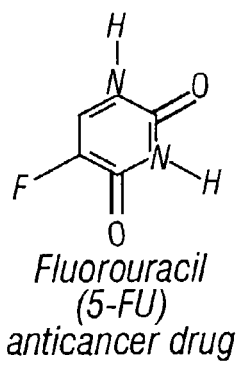
FIG. 9 shows structures of some commercially useful fluoroorganic compounds.
Figure 9:
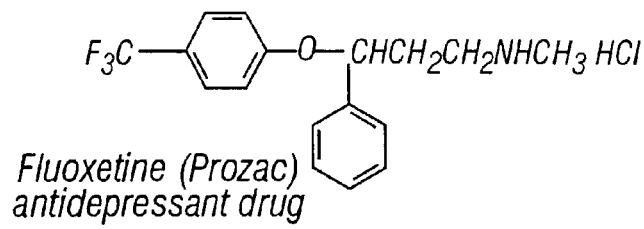
Figure 9:
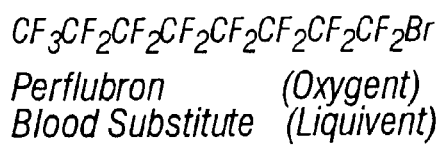
Figure 9:
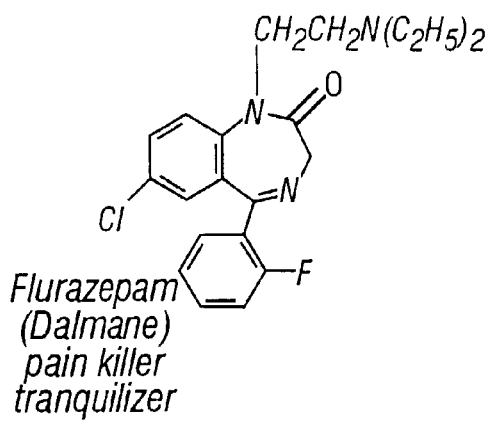
Figure 9:
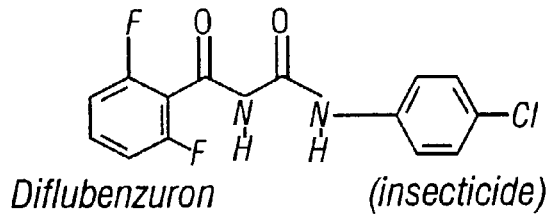
Figure 9:
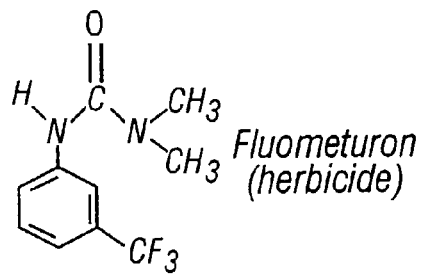
Figure 9:
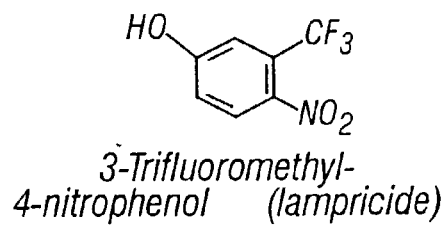
Figure 9:
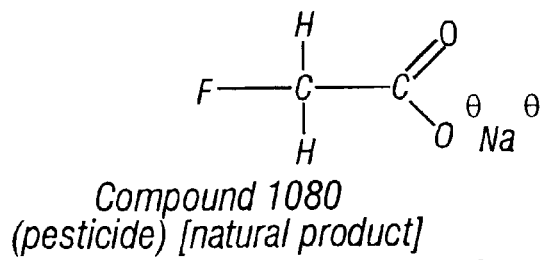
Figure 9:
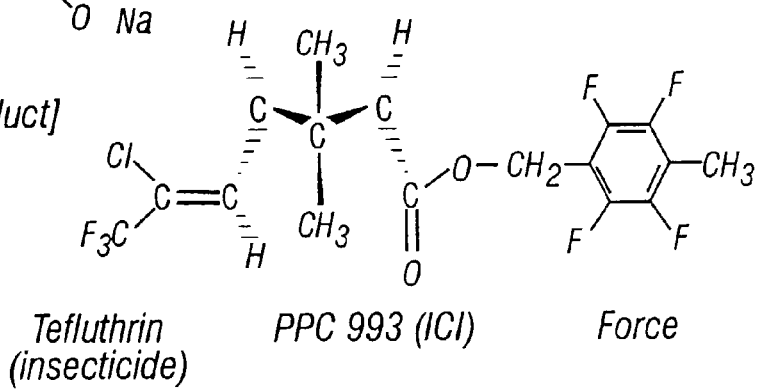
Figure 10:
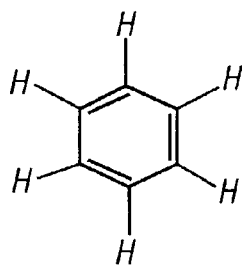
FIG. 10 shows structures of various compounds having Raman spectra.
Figure 10:
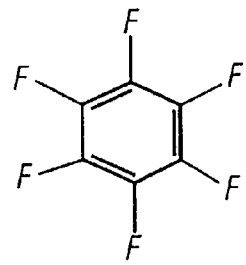
Figure 10:
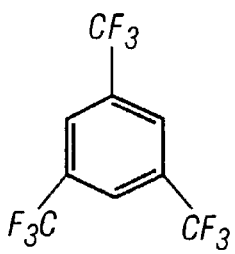
Figure 10:
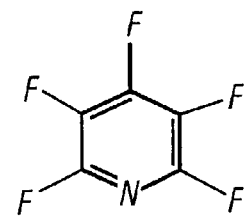
Figure 10:
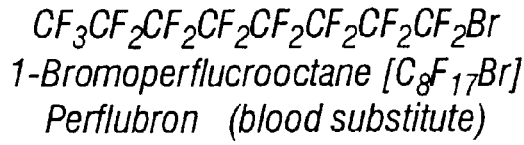
Figure 10:
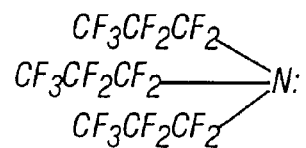
Figure 10:
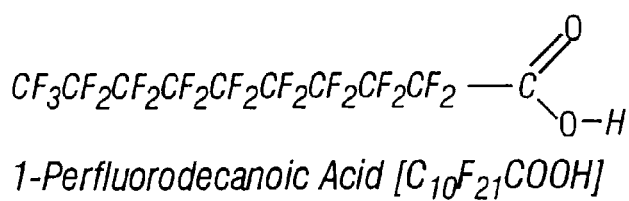
Figure 10:
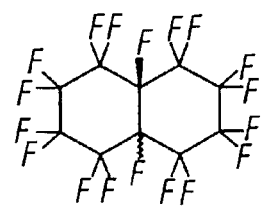
Figure 10:
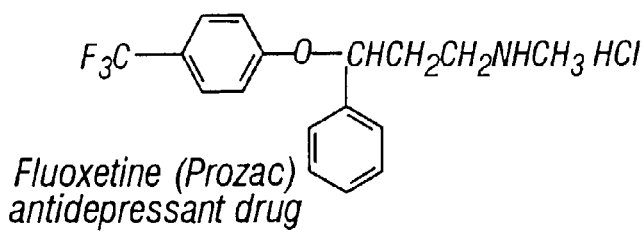

Many fluoroorganic compounds are manufactured commercially. Most of the compounds find use as drugs in medicine or veterinary medicine, anesthetics, herbicides, insecticides, pesticides or as industrial intermediates. FIG. 9 shows the structures of some commercially useful compounds. These compounds include carbon-fluorine bonds of trifluoromethyl groups, aromatic carbon-fluorine bonds, and perfluoroalkyl groups.

Aromatic carbon-fluorine bonds are observed in the range of 540-610 cm$^{-1}$. Examples are hexafluorobenzene, 569 cm$^{-1}$; and pentafluoropyridine, 589 cm$^{-1}$.

Figure 5:
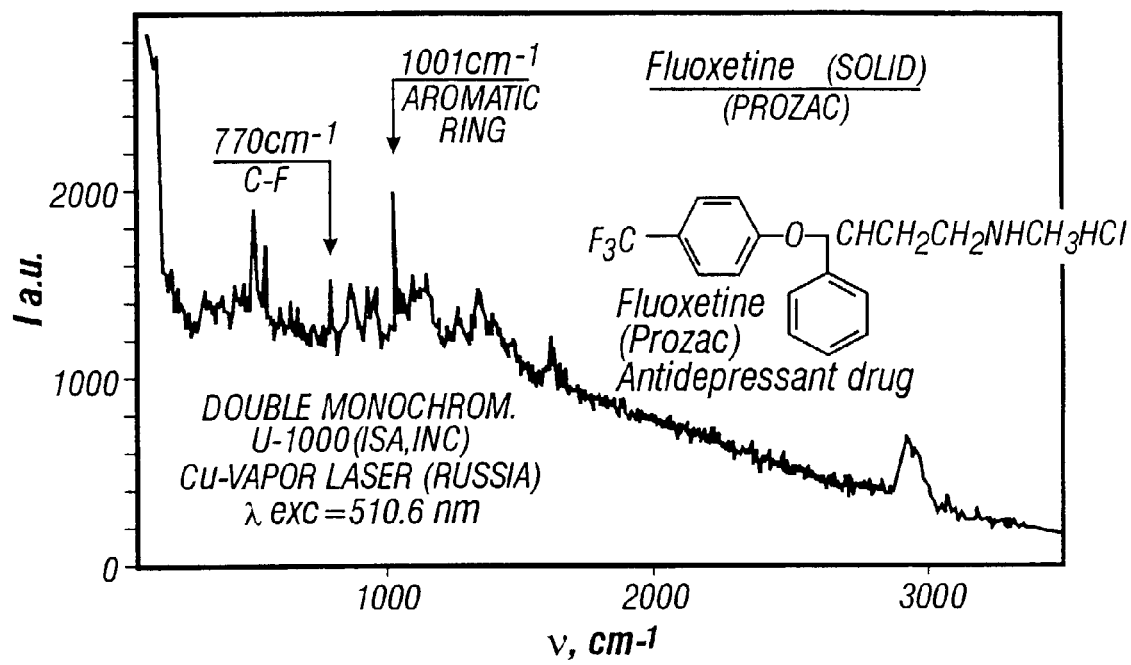
FIG. 5 is a Raman spectrum of a commercial preparation of fluoxetine hydrochloride using the spectrometer of FIG. 1.

Trifluoromethyl groups are observed in the range of 710-785 cm$^{-1}$. Examples are: 1-bromoperfluorooctane, 726 cm$^{-1}$; perfluorodecanoic acid, 730 cm$^{-1}$; triperfluoropropylamine, 750 cm$^{-1}$; 1,3,5-tris —(trifluoromethylbenzene), 730 cm$^{-1}$; fluoxetine (Prozac®) commercial powdered pill at 770 cm$^{-1}$. TABLE 1 (see, Key et al., *Environmental Science and Technology* 31: 2445-2454, 1997) lists commercial fluoroorganic compounds containing trifluoromethyl groups. Most of these compounds have an aromatic ring, so resonance Raman can be observed. For example, Prozac® gives a sharp identifiable signal at 770 cm$^{-1}$, as shown in FIG. 5.

TABLE 1

APPLICATIONS OF TRIFLUOROMETHYL-SUBSTITUTED ORGANIC COMPOUNDS

| Herbicides | Insecticides | Medicinal (Use) |
|---|---|---|
| acifluorifen | acrinathrin | bendroflumethiazide |
| benfluralin | bifenthrin | (antihypertensive) |
| diflufenican | chlorfluazuron | dexfenfluramine |
| dinitramine | cyhalothrin | (obesity) |
| dithiopyr | flucofuron | fenfluramine |
| ethaifluralin | flufenoxuron | (anorectic) |
| flazasulfuron | X-fluvalinate | fluoxetine |
| fluazifop | hydramethylnon | (antidepressant) |
| fluchioralin | tefluthrin | fluphenazine |
| flumetralin | triflumuron | (antipsychotic) |
| fluometuron | Rodenticide | halofantrine and |
| fluoroglycofen | bromethalin | mefloquine•HCl |
| flurazole | flocoumafen | (antimalarials) |
| flurochloridane | flupropadine | nilutamide (cancer) |
| flurprimidol | Fungicide | tolrestat (diabetes) |
| flurtamone | fluazinam | |
| fluxofenim | flusulfamide | |
| fomesafen | flutolanil | |
| furyloxyfen | furconazole | |
| haloxyfop | triflumizole | |
| lactofen | Anaesthetics | |
| mefluidide | fluroxene | |
| nipyraclofen | halothane | |
| norflurazon | methoxyflurane | |
| oxyfluorfen | isoflurane | |
| perfluidone | sevoflurane | |
| prodiamine | desflurane | |
| profluralin | Lampricide | |
| thiazafluron | trifluoromethyl- | |
| trifluralin | nitrophenol | |

When no trifluoromethyl group is present, difluoromethylene groups are observed in a range centered at 690 cm$^{-1}$. An example is perfluorodecalin, a component of blood substitutes developed in Japan and Russia.

In particular embodiments, Raman spectroscopy can be performed on 1-bromoperfluorooctane ($C_8F_{17}Br$; BPFO), polycrystalline perfluorodecanoic acid ($C_9F_{19}COOH$; PFDA), 1,3,5-tris —(trifluoromethyl)—benzene ($C_6H_3(CF_3)_3$; TTFMB); or fluoxetine (Prozac®). The first compound ($C_8F_{17}Br$) is a candidate to carry oxygen in a blood substitute. The second compound ($C_8F_{17}COOH$) is an analog of perfluorooctanoic acid (PFOA), but less volatile. PFOA has been found in tissues of workers exposed to PFOA in the workplace. The third compound ($C_6H_3(CF_3)_3$) contains carbon-fluorine bonds that are in trifluoromethyl groups. $C_6H_3(CF_3)_3$ is an analog of many useful compounds now sold commercially as drugs, herbicides, and pesticides, some of which are presented in TABLE 1. Fluoxetine (Prozac®; $C_{17}H_{18}F_3NO$) is a widely prescribed drug which contains a trifluoromethyl group.

In further embodiments, resonance Raman spectroscopy can be performed on perfluorodecalin ($C_8F_{18}$, PFD) and 1-bromoperfluorooctane ($C_8F_{17}Br$, BPFO). The schematic of the instrument used to observe the resonance Raman spectra is given in FIG. 6. Most of the compounds of TABLE 1 should give enhanced resonance Raman spectra.

Figure 2:
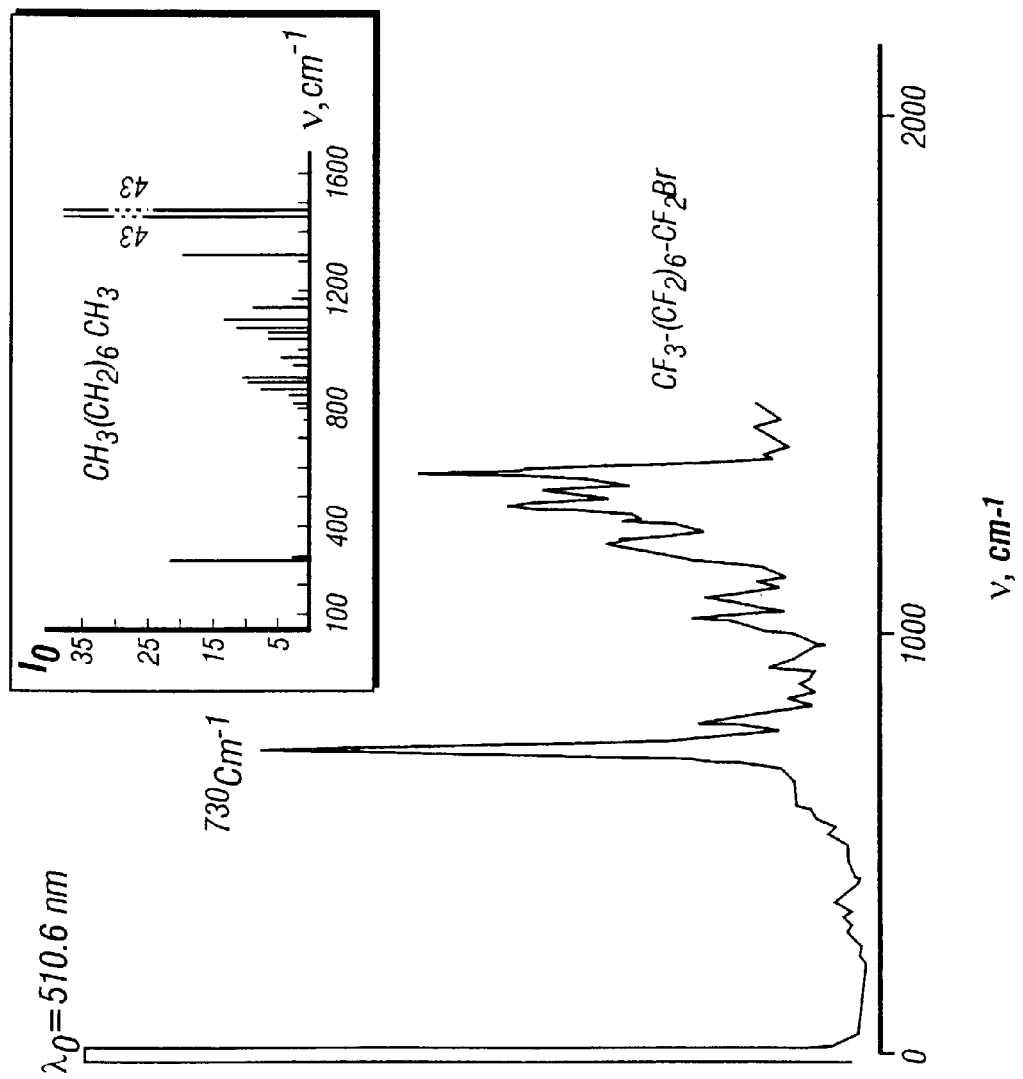
FIG. 2 is a Raman spectrum of $C_8H_{17}Br$ (bromoperfluorooctane) and $C_8H_{18}$ using the spectrometer of FIG. 1.

A Raman spectrum (0-1500 cm$^{-1}$) of liquid $C_8F_{17}Br$ (BPFO) is shown in FIG. 2. A very strong peak at 730 cm$^{-1}$ is present in this spectrum. The compound $C_8F_{17}Br$ is a fluoro-derivative of octane ($C_8H_{18}$) in which the 18 hydrogens are replaced with 17 fluorine atoms and one atom of bromine. FIG. 2 also shows a Raman spectrum of $C_8H_{18}$ in the upper right corner. This spectrum does not have a peak near 730 cm$^{-1}$. As in $C_6H_3(CF_3)_3$ spectrum, the appearance of the 730 cm$^{-1}$ peak in $C_8F_{17}Br$ is due to a carbon-fluorine bond signature. This peak corresponds to a fully symmetric vibrational normal mode of a molecule containing the carbon-fluorine bond, specifically the trifluoromethyl group or perfluoroalkyl group.

Figure 3:
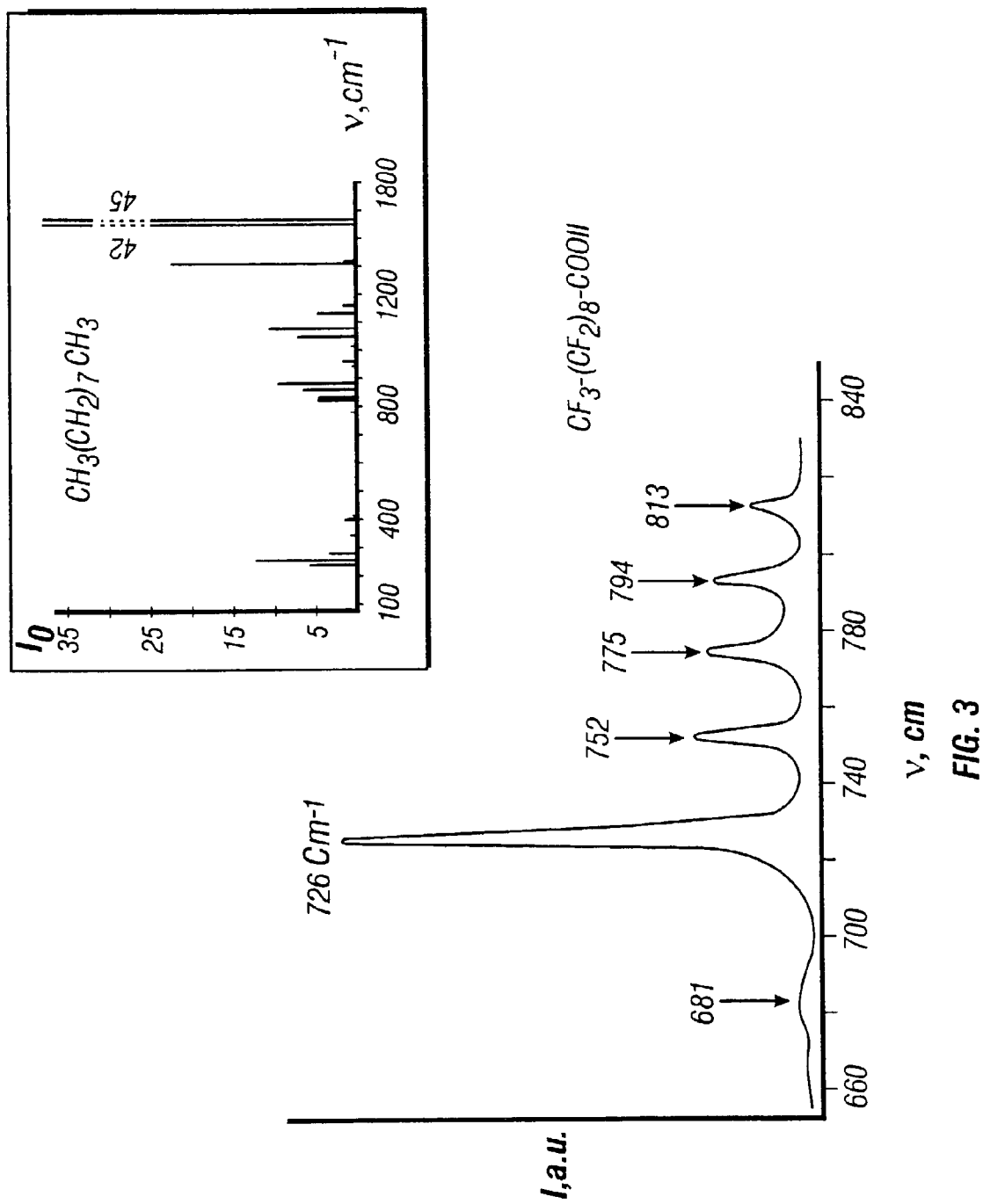
FIG. 3 is a Raman spectrum of $C_9F_{19}COOH$ ($C_{10}HF_{19}O_2$; bromoperfluordecanoic acid). $C_9H_{20}$ (nonane, a hydrocarbon) using the spectrometer of FIG. 1.

A Raman spectrum for polycrystalline $C_9F_{19}COOH$ (PFDA) is given in FIG. 3. As for earlier discussed fluoroorganic compounds, a characteristic peak at 726 cm$^{-1}$ has been observed for $C_8F_{17}COOH$. This peak was assigned as a fully symmetric vibrational normal mode of a molecule containing the C—F bond, specifically the trifluoromethyl group or perfluoroalkyl group. The Raman spectrum of nonane ($C_9H_{20}$) is shown in the upper right corner in FIG. 3. The nonane spectrum does not have any characteristic spectral lines close to 730 cm$^{-1}$.

Figure 4:
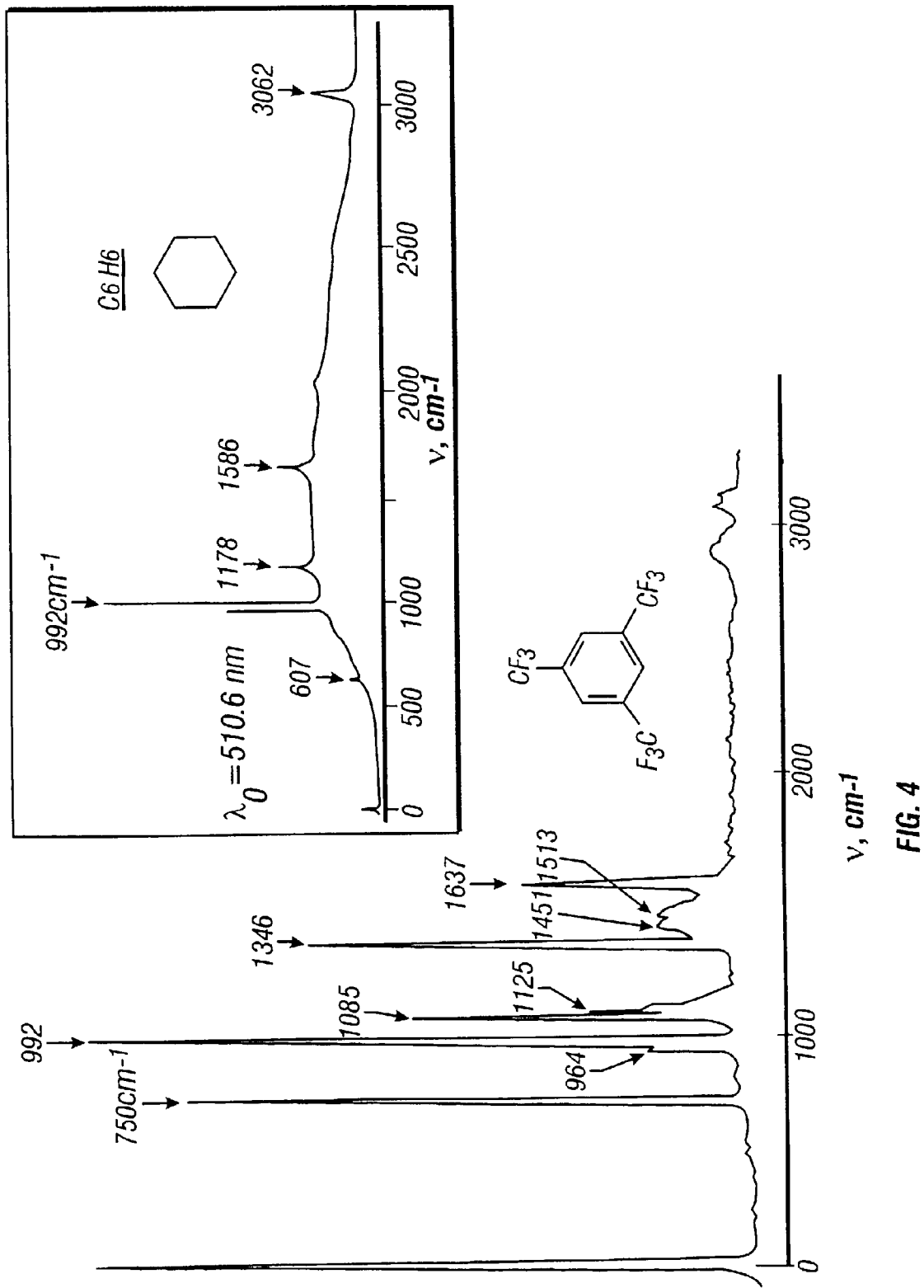
FIG. 4 is a Raman spectrum of $C_6H_3(CF_3)_3$ [1,3,5-tris (trisfluoromethyl)benzene] and $C_6H_6$ (benzene) using the spectrometer of FIG. 1.

A Raman spectrum for $C_6H_3(CF_3)_3$ (TTFMB) and benzene ($C_6H_6$, upper right) are shown in FIG. 4. When these two Raman spectra are compared, each has a well-resolved peak at 992 cm$^{-1}$, which corresponds to the fully symmetric vibrational mode of the benzene ring. At wave numbers greater than 992 cm$^{-1}$ the Raman spectrum of $C_6H_3(CF_3)_3$ shows a doublet at 1085$^{-1}$, 125 cm$^{-1}$, and spectral lines at 1376 cm$^{-1}$, 1513 cm$^{-1}$, and 1637 cm$^{-1}$ instead of the single lines at 1178 cm$^{-1}$ and 1586 cm$^{-1}$ found for carbon in benzene. The difference between $C_6H_3(CF_3)_3$ and unsubstituted benzene becomes apparent below 992 cm$^{-1}$. Benzene shows only two weak peaks which correspond to the deformation modes of the C—C bond. By contrast, $C_6H_3(CF_3)_3$ shows a strong peak at 730 cm$^{-1}$ comparable in intensity to the peaks in $C_6H_3(CF_3)_3$ and $C_6H_6$ at 992 cm$^{-1}$. The 730 cm$^{-1}$ peak is assigned as a fully symmetric vibrational normal mode of the trifluoromethyl group of the molecule.

The Raman spectrum in FIG. 5 is of the contents of a fluoxetine ($C_{17}H_{18}F_3NO$) hydrochloride (Prozac®) capsule in the solid powdered form. The composition of the capsule is unknown other than the presence of fluoroxetine hydrochloride. The very narrow sharp peak at 770 cm$^{-1}$ is assigned to a symmetrical vibration involving the trifluoromethyl group. The symmetric aromatic vibration is found at 1001 cm$^{-1}$.

The Raman spectra of each of the four fluoroorganic compounds ($C_8F_{17}Br$, $C_8F_{17}COOH$, $C_6H_3(CF_3)_3$, and $C_{17}H_{18}F_3NO$) show a characteristic fully symmetric vibrational strong peak at frequencies in the range of 720-770 cm$^{-1}$ which are assigned to molecular vibrations of the trifluoromethyl group or perfluoroalkyl groups. Comparison of the Raman spectra of the fluoroorganic compounds with their hydrocarbon analogs, suggest that the observed spectral emissions in the range of 690-770 cm$^{-1}$ are associated with the carbon-fluorine bonds of the compounds studied.

Figure 7A:
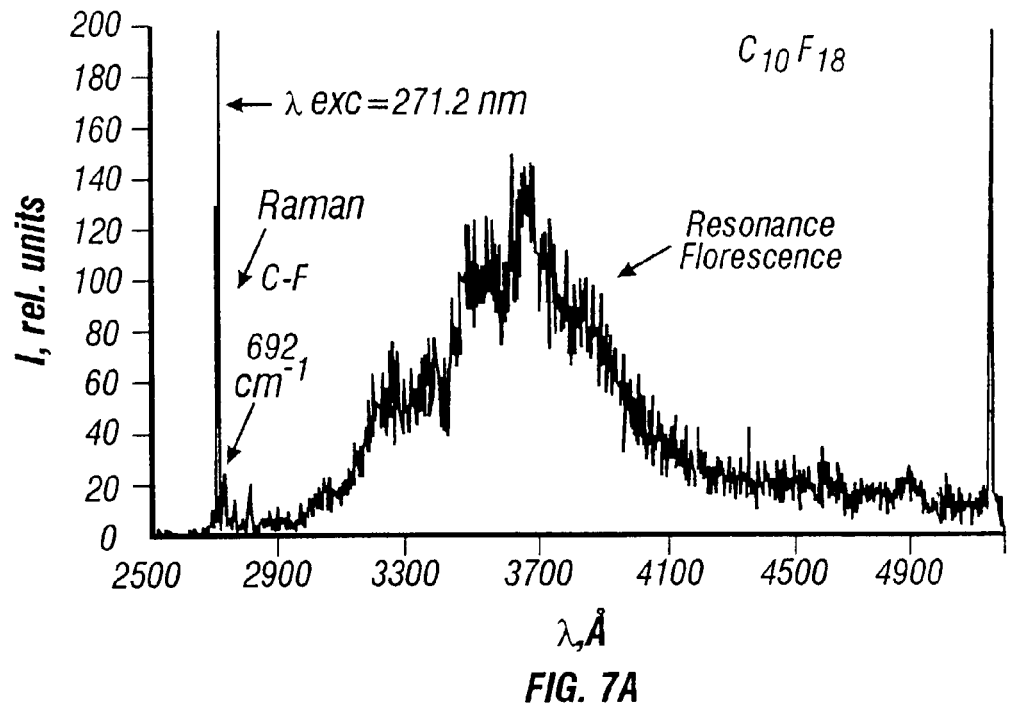
FIG. 7 is a resonance Raman spectrum of irradiate perfluorodecalin showing a difluoromethylene absorption. The top spectrum is an unprocessed resonance Raman spectrum of perfluorodecalin ($C_{10}F_{18}$). The bottom spectrum is a partially processed resonance Raman spectrum of perfluorodecalin.
Figure 7B:
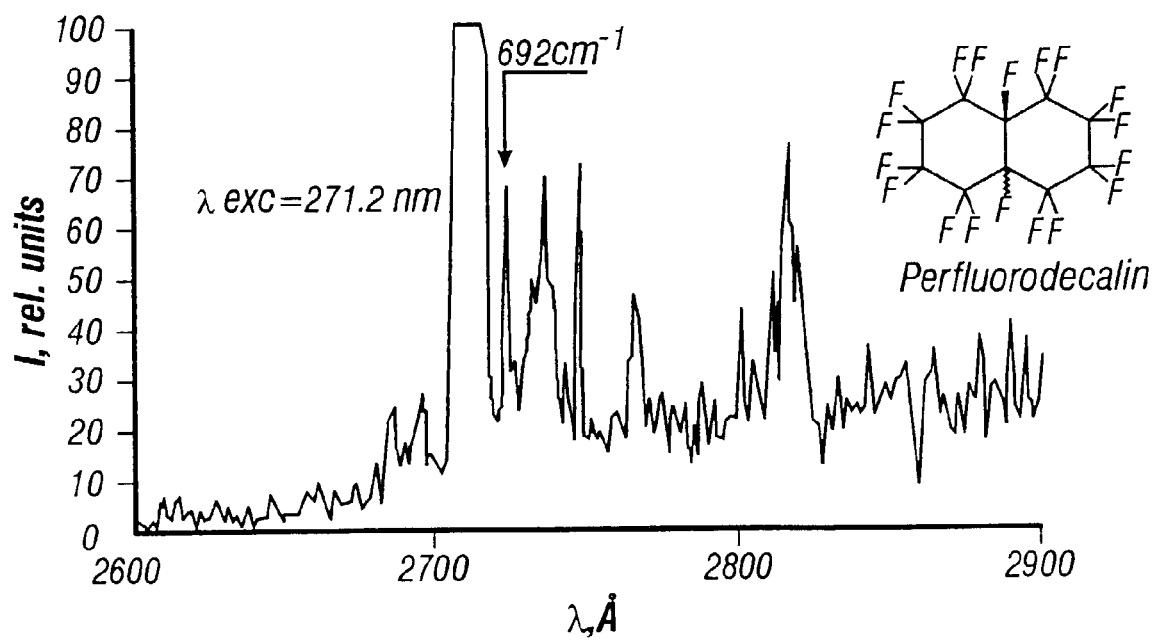
Figure 8:
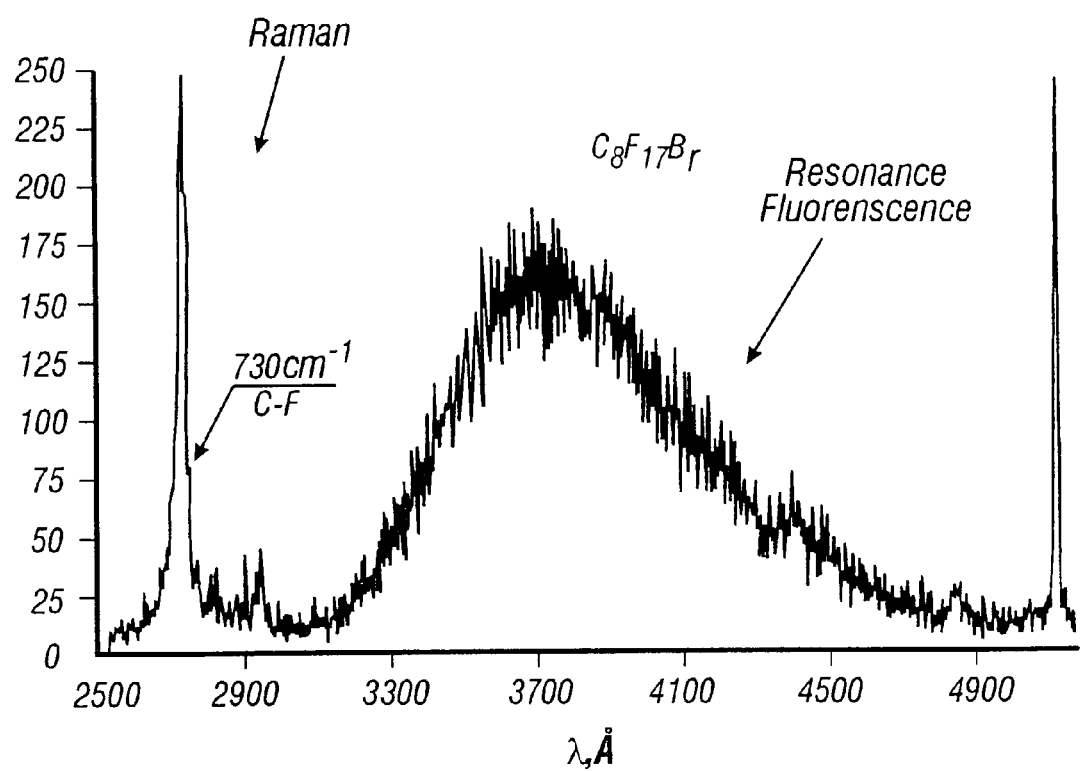
FIG. 8 is a resonance Raman spectrum of 1-bromoperfluorooctane using the spectrometer of FIG. 6.

Resonance Raman spectra of perfluorodecalin ($C_8F_{18}$) and 1-bromofluorooctane ($C_8F_{17}Br$) are shown in FIG. 7 and FIG. 8. These spectra are shown at two different scales, but are not otherwise electronically processed to enhance the signals. The narrow sharp emission at 692 cm$^{-1}$ is believed to be the totally symmetric normal mode of the difluoromethylene groups ($CF_2$). 1-bromoperfluorooctane has a weak ultraviolet absorption maximum about 275 nm ($\epsilon$=50) and gives a resonance Raman spectrum with a 730 cm$^{-1}$ emission signal, which is the same emission shown in the regular Raman spectrum (FIG. 2).

Carbons in the "quasi-linear" or "quasi-one-dimensional" fluororganic molecule chain having a formula $C_nH_{2n+2}$ e.g., $C_nF_{2n+1}$ can also be identified. These molecules are often used in drug formulations, which transport oxygen or carbon dioxide in blood substitutes. These molecules are also used in other pharmaceutical and medicinal applications. Examples of these molecules include $C_{11}H_{11}F_3N_2O_2$ (flutamide) and $C_{10}F_{19}O_2K$ (potassium perfluorodecanoate).

Many linear or quasi-linear fluororganic compounds with different substitution groups can be identified. For example, a substitution group occurs when hydrogens of a molecule are replaced with fluorine to create a fluorocarbon compound. Suitable compounds include anesthetics and those listed in Table 2 below.

The $C_nH_{2n+2}$ molecules may be modeled as a resonator. The length of the molecule is inversely proportional to the number of carbons ("n") in the hydrocarbon chain, if n is relatively large. Fluororganic compounds experience a longitudinal acoustic mode (LAM) and a longitudinal optical mode (LOM) frequency shift. These shifts are dependent on the number of carbons in the molecule chain.

A Raman spectra was obtained using an argon laser at about 488.0 nm or a copper-vapor laser at about 510.5 nm. The laser power was about 100 mW. A computerized DFC-24 recording spectrometer with 1 cm$^{-1}$ slit width was employed which was capable of monitoring the position of the gratings. The samples were clear liquid or white crystalline powders. Quartz cuvettes with parallel windows and close fitting tops were used for liquid samples. Raman observations were made at 90-degrees from the incident radiation.

Figure 11:
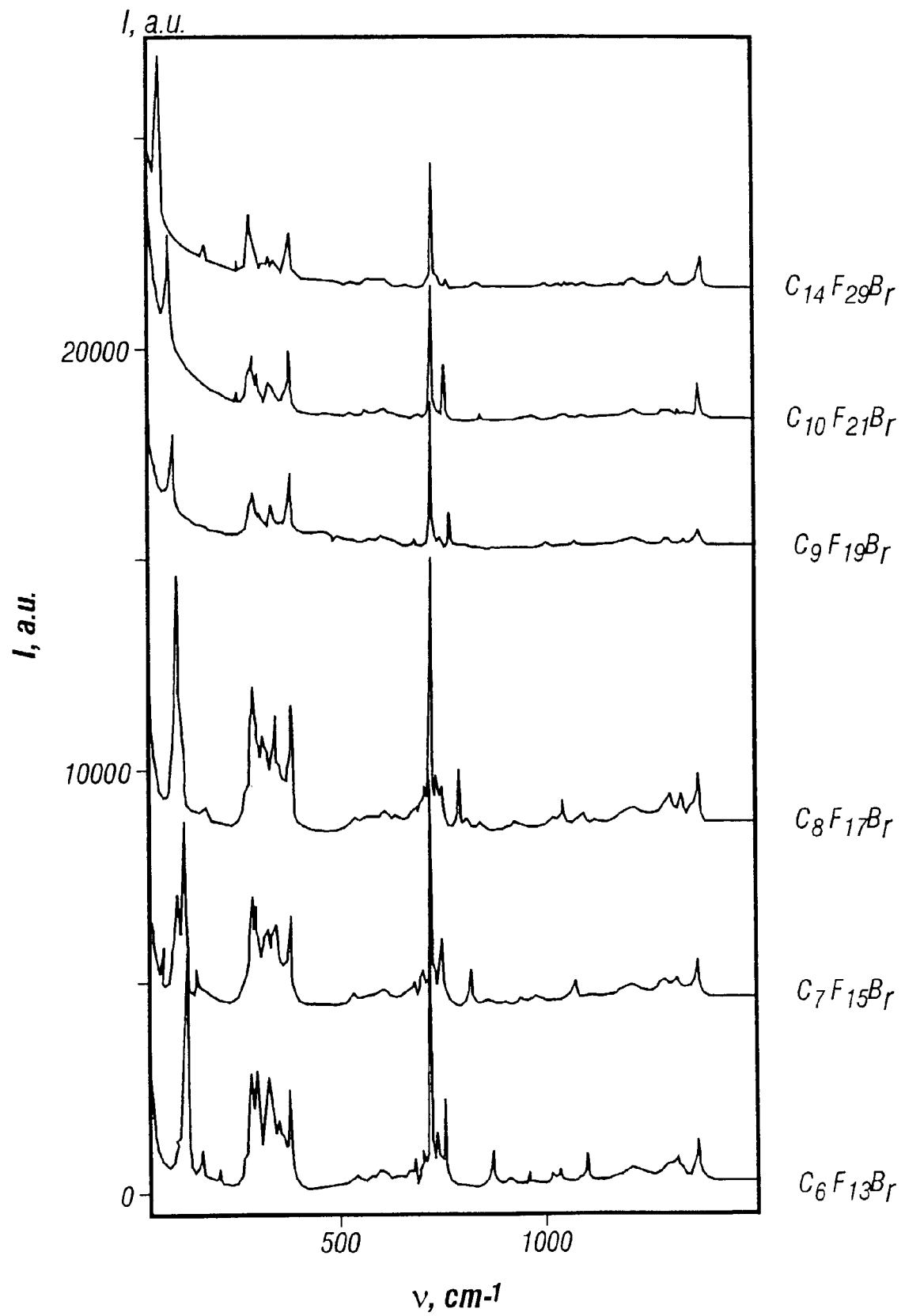
FIG. 11 illustrates Raman spectra of $C_nF_{2n+1}Br$ for n=6, 7, 8, 9, 10, 14 in the region 0-1500 $cm^{-1}$.
Figure 12:
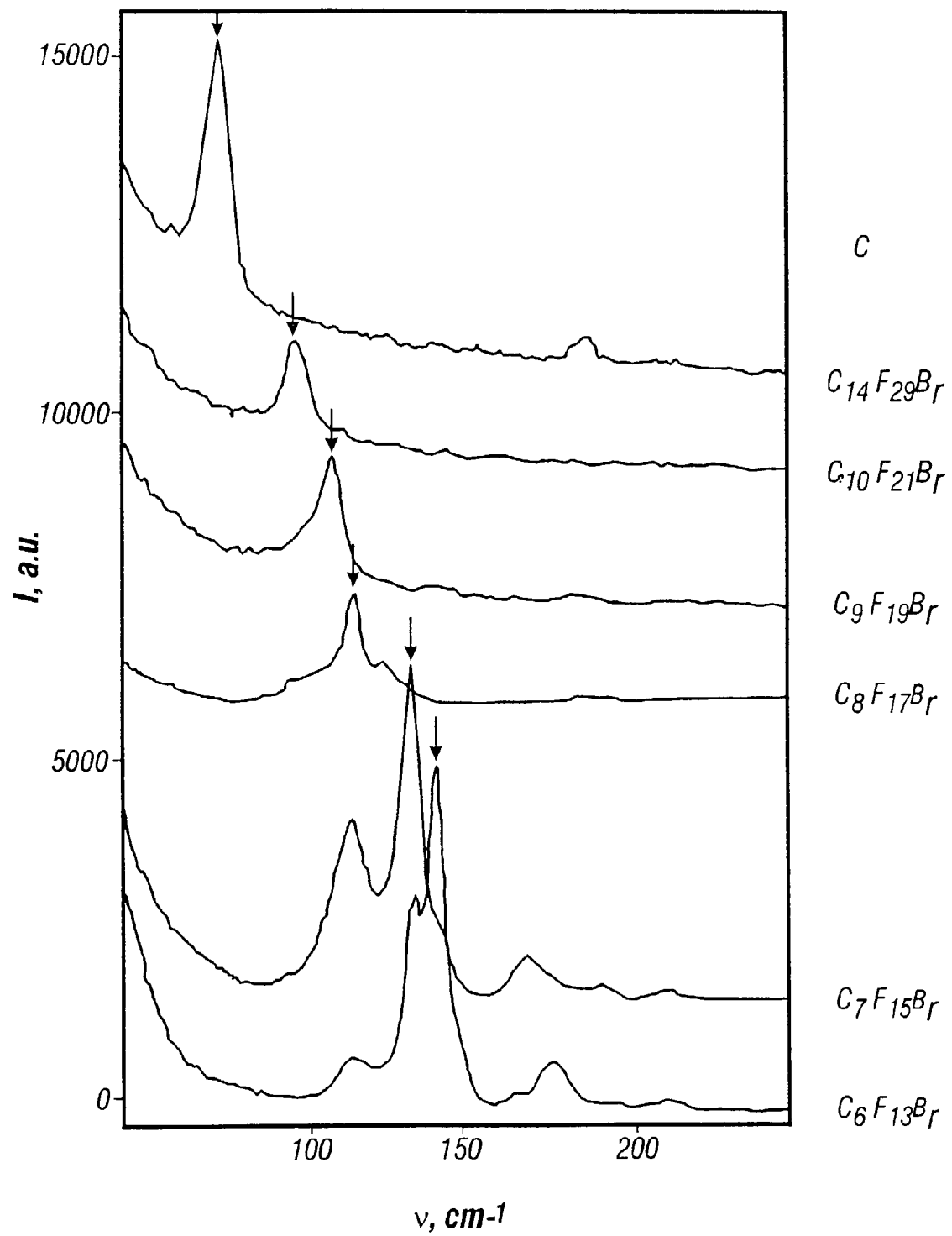
FIG. 12 illustrates the dependency of Raman spectra on the unit length of a molecule in the lower frequency region LAM.

FIG. 11 shows Raman spectra in the region 0-1400 cm$^{-1}$ for $C_nF_{2n+1}Br$. A sharp peak in the region 719-730 cm$^1$ was observed for all Raman spectra. This peak corresponds to the fully symmetrical normal vibration of $CF_2$ bond. FIG. 12 illustrates that with an increase in n, the maximum peak increased linearly. This means that the peak intensity depends on the length of the molecule.

FIG. 12 illustrates an intensive peak in the region 0-500 cm$^{-1}$ and overlapping bands in the region 200-300 cm$^{-1}$. For n=6, 7, and 8, the observed lower frequency band (LAM) included several components. For n=9, 10 and 14 the band did not have splitting. A peak signal that was single was observed from $C_{14}$ to $C_9$. However, from $C_8$ to $C_6$, the peak began to split.

Figure 13:
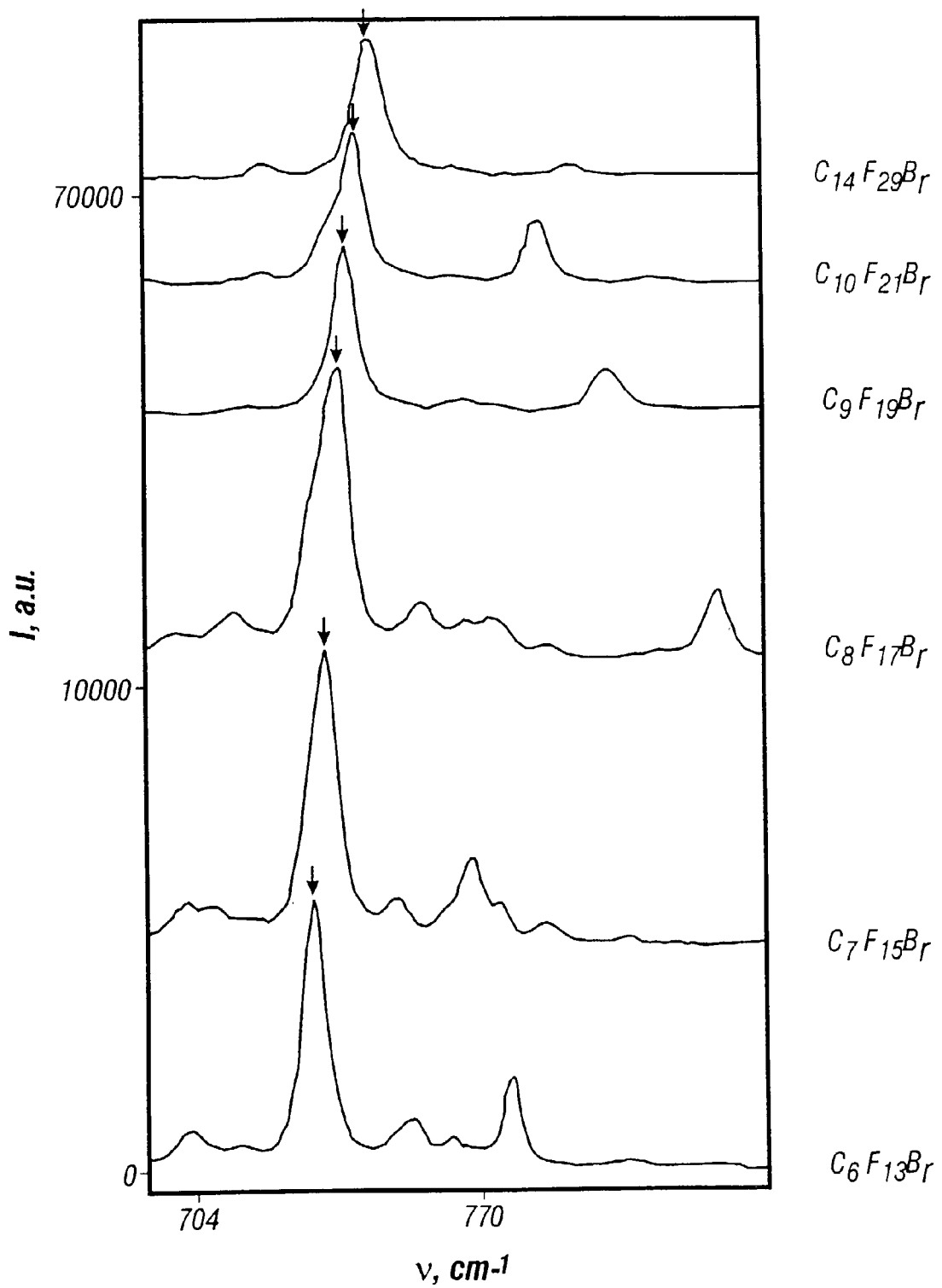
FIG. 13 illustrates the dependency of Raman spectra on the unit length of a molecule in the higher frequency region LOM.

FIGS. 12 and 13 show that lower frequency LAM 80-150 cm$^{-1}$ and higher frequency regions LOM 700-750 cm$^{-1}$ of Raman spectra of $C_nF_{2n+1}Br$ compounds depend on the number of carbons in the molecule chain. The frequency of the LAM decreases as n increases (FIG. 12). However, the frequency of LOM increases when n increases (FIG. 3).

Figure 15:
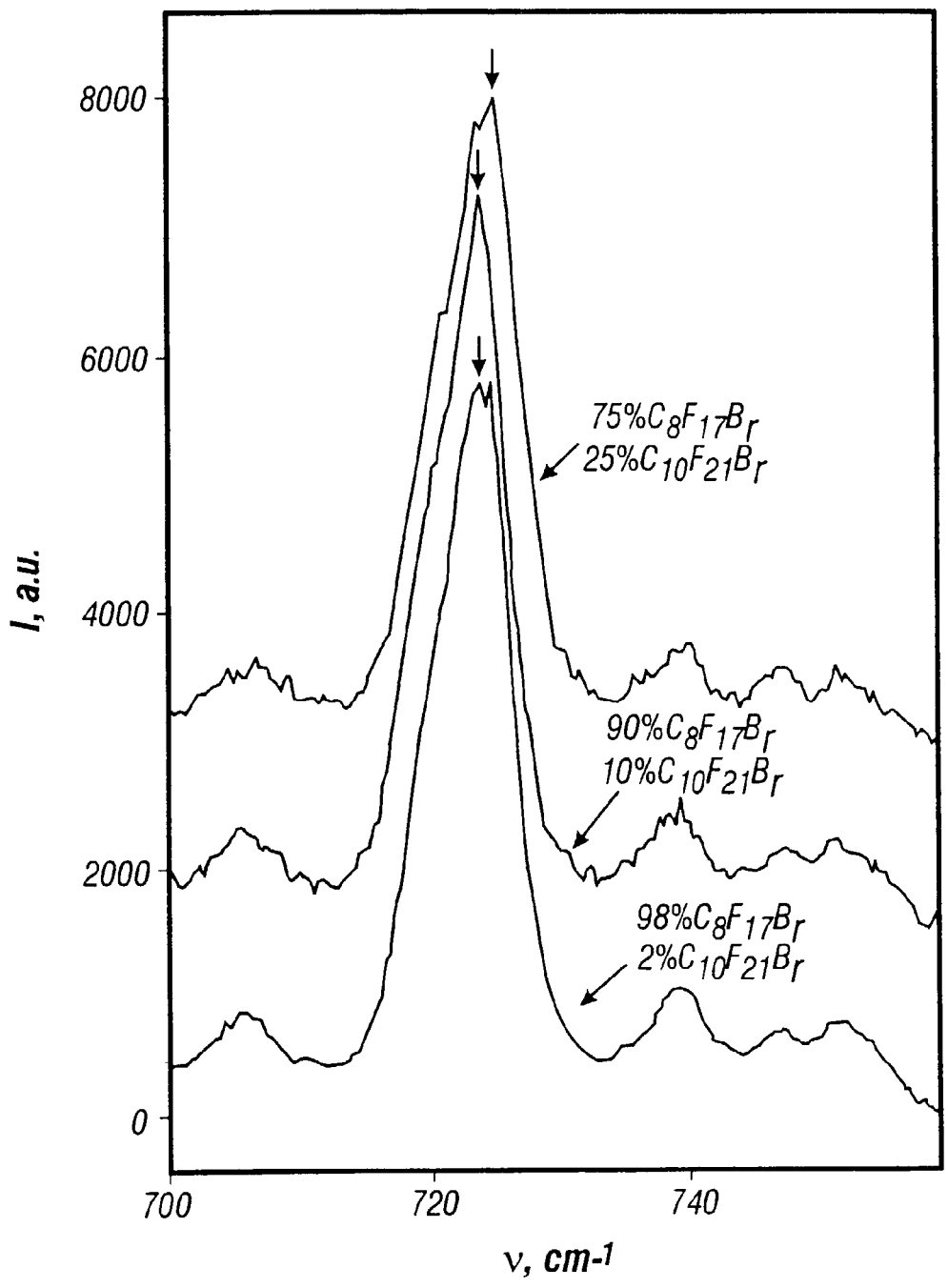
FIG. 15 illustrates the Raman spectra of a two-component mixture of $C_nF_{2n+1}Br$ obtained at three concentrations of components at a Raman signal for a $CF_2$ bond.
Figure 16:
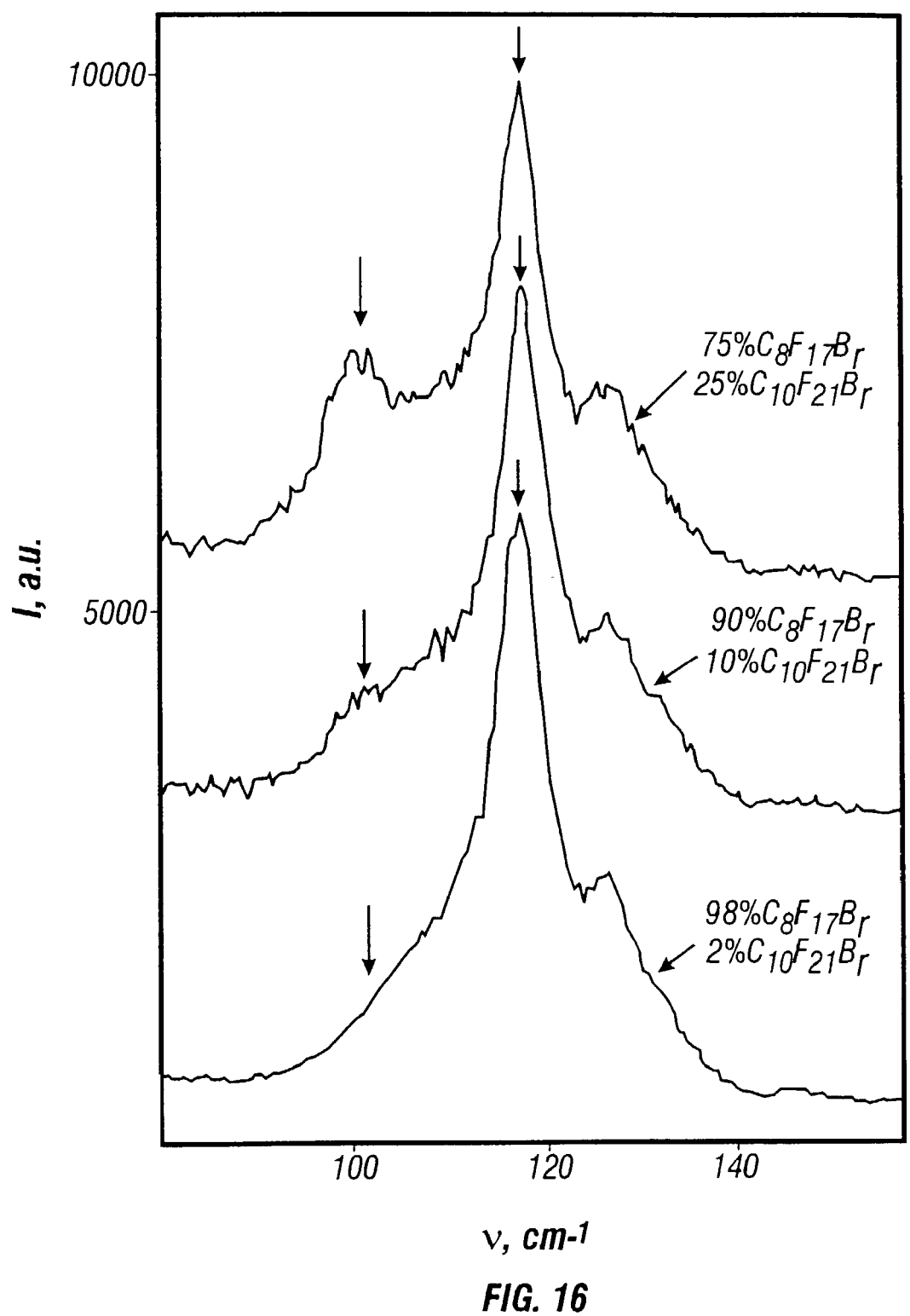
FIG. 16 illustrates the Raman spectra of a two-component mixture of $C_nF_{2n+1}Br$ obtained at three different concentrations of the components at a characteristic Raman signal in the lower frequency region LAM band.

FIGS. 15 and 16 show Raman spectra of mixtures of fluororganic compounds in the spectral area characteristic for a $CF_2$ bond and the Raman spectra of such mixtures in the lower frequency region LAM. At a concentration higher than about 2%, the Raman peaks were identified for the certain type of the fluoroorganic compound.

Table 2 below lists Raman spectral data for $C_{12}F_{2n+1}Br$ in the LAM and LOM frequency ranges.

TABLE 2

| Wave number, cm$^{-1}$ | Relative Intensity | Bandwidth, cm$^{-1}$ | Compound |
|---|---|---|---|
| 77.7 | 3634 | 7.4 | $C_{14}F_{29}Br$ |
| 100.9 | 1236 | 5.4 | $C_{10}F_{21}Br$ |
| 111.4 | 1533 | 7.0 | $C_9F_{19}Br$ |
| 117.5 | 1409 | 6.0 | $C_8F_{17}Br$ |
| 134.6 | 4694 | 7.1 | $C_7F_{15}Br$ |
| 142.1 | 4804 | 6.3 | $C_6F_{13}Br$ |
| 730.3 | 2962 | 5.5 | $C_{14}F_{29}Br$ |
| 727.3 | 2964 | 4.4 | $C_{10}F_{21}Br$ |
| 725.4 | 3398 | 4.7 | $C_9F_{19}Br$ |
| 723.9 | 5310 | 4.7 | $C_8F_{17}Br$ |
| 721.1 | 5048 | 4.1 | $C_7F_{15}Br$ |
| 719.8 | 5567 | 4.2 | $C_6F_{13}Br$ |

Comparison of the different Raman spectra of mixtures of fluororganic compounds indicates that the observed shifts depends on the length of the molecules. The acoustic and optical modes of vibration can be described using the dispersion law as follows:

$$\omega_{acoustic} = 2(S/a) \times \sin^2(ka/2), \quad (1)$$

$$\omega_{optical} = \omega_0^2 - 4(S^2/a^2) \times \sin^2(ka/2), \quad (2)$$

where $\omega_{acoustic}$ is the frequency of the acoustic mode;

$\omega_{optical}$ is the frequency of the optical mode;

k is a vector which has a value of $2\pi/\lambda$, where $\lambda$ is the wavelength;

a is the distance between atoms of a molecule chain;

S is the acoustical propagation speed.

The vector k and the frequencies $\omega_{acoustic}$ and $\omega_{optical}$ can have various discrete values if the length of the molecule chain is finite and has determined limits. Using the shift of the acoustical and optical frequencies and plotting CF molecular length of CF versus the frequency shift, the molecular length ("L") of quasi-linear molecules in mixtures of fluorocarbon molecules can be estimated. Accordingly, the minimum value for the frequencies can be calculated as follows:

For $f = \omega_{acoustic}/2\pi$ at the acoustic mode LAM:
$$f_{acoustic} = 2(S/2\pi a) \times \sin(ka/2) \approx (S/\pi a) \times (\pi a/2L) = (S/2L), \text{ where } L \gg a \text{ and } k_{min} = \pi/L. \quad (3)$$

For $f = \omega_{optical}/2\pi$ at the optical mode LOM:
$$f_{optical}^2 = f_0^2 - 4(S_2/4\pi^2 a^2) \times \sin^2(\pi a/2L) \approx f_0^2 - S^2/4L^2, \text{ where L is the length of the molecule.} \quad (4)$$

Assuming that $v_0 = \omega_0/2\pi c$, $v = \omega/2\pi c$, and $k_{min} = \pi/L$, where $v$ and $v_0$ are wave numbers, and c is the speed of light, the wavenumber dependencies the length (L) of the molecule for the acoustical ($v_{acoustic}$) and optical ($\omega_{optical}$) branches can be calculated as:

$$v_{acoustic} = (S/\pi ac) \times \sin(\pi a/2L). \quad (5)$$

$$v_{optical}^2 = v_0^2 - (S^2/\pi^2 a^2 c^2) \times \sin^2(\pi a/2L). \quad (6)$$

Figure 14:
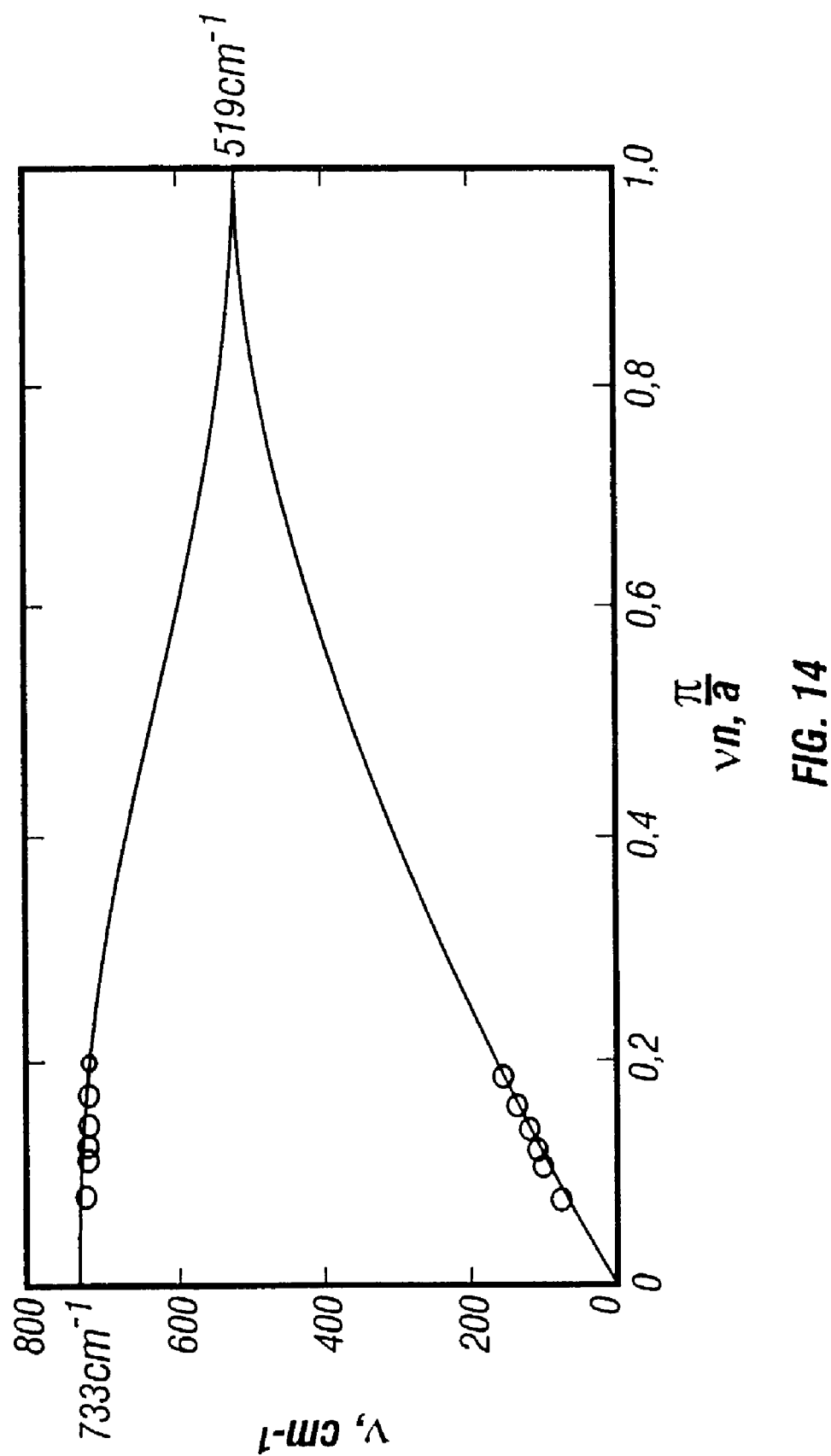
FIG. 14 illustrates experimental Raman frequencies.

FIG. 14 illustrates experimental Raman frequencies indicated by circles for $C_nF_{2n+1}Br$ at n=6, 7, 8, 9, 10, and 14. The experimental frequencies represent the values of the spectra indicated in FIGS. 11-13. FIG. 14 also illustrates calculated frequencies, as indicated by solid lines, that match the above spectra values. These calculations assume that L=na/2, where n is the number of carbons, e.g., 6, 7, 8, 9, 10, and 14. Comparison of the experimental and calculated frequencies indicates that actual Raman frequencies for varying values of n can be accurately calculated using the preferred method.

The dependency of the length of the molecule on the Raman signal has been established in "quasi-one-dimensional" molecules of fluororganic compounds. With an increase in the molecular length, the high frequency (optical) mode LOM of $CF_2$ linearly increases, and the lower frequency (acoustical) mode LOM decreased. Accordingly, the length of the molecular species in a mixture using the changing optical and acoustical frequency modes can be approximated.

Figure 17:
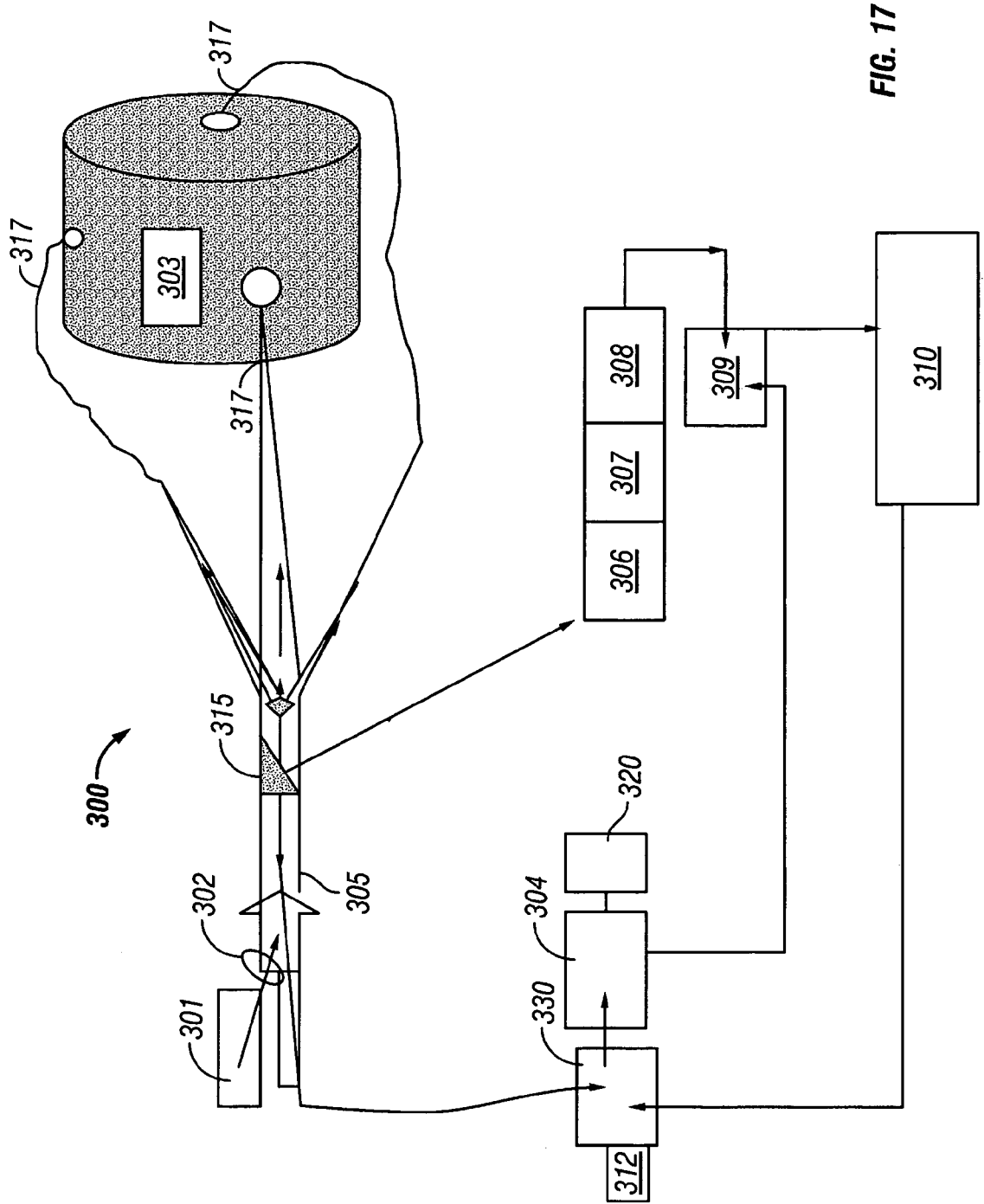
FIG. 17 is a schematic drawing of an instrument in a first embodiment.

FIG. 17 illustrates an instrument 300 in an embodiment. The instrument 300 may be used for Pulsed Laser Isochronic Raman Spectroscopy ("PLIR"), Pulsed Isochronic Surface Enhanced Raman Spectroscopy ("PLISERS") or Pulsed Laser Isochronic Fluorescence ("PLIF") applications. The PLISERS, PLIF and PLIR applications may occur in the ultraviolet ("UV"), infrared ("IR"), or visible ("VIS") region. For PLIF applications, the instrument 300 may be used to analyze a sample, product, or biological molecule using a carbon—halogen bond, such as a carbon-fluorine ("C—F") bond, as a tracer or fluorescence label. For PLIR and/or PLISERS applications, the instrument 300 may be used to analyze a sample, product, or biological molecule using a carbon—halogen bond, such as a C—F bond, as a chemical or Raman (optical) label.

The instrument 300 may include a laser source 301, which may be a pulsed metal vapor source or other pulsed laser source. In one embodiment, the laser source 300 may provide a short duration of pulses, for example, in nanoseconds. The average power of the laser source 301 may be approximately 0.25-3 watts, and the peak power may be about 10-25 kilowatts. In one embodiment, the laser source 301 may be a visible copper vapor laser or an infrared gold metal vapor laser. Copper and gold vapor lasers may be used to reject fluorescence during Raman measurements. A copper vapor laser may increase the Raman cross-section. Such lasers may be used with time-gating and time-delay devices, and each laser may provide a high level of specificity for the detection for carbon—halogen bonds such as C—F bonds. A copper vapor laser may also reduce signal-to-noise ratios and provide a sensitivity of detection at femto molar and/or a femto gram levels. The laser source 301 may also have long hours of operation, for example, 1500 hours without the need of changing an active element, e.g., a tube.

For IR applications, an Nd: YAG pulsed laser or other solid-state pulse laser may be used. The laser source 301 may also have a sealed-off UV or VIS copper vapor laser having an excitation at about 510.6 nanometers to about 578.2 nanometers. In another embodiment, a UV nitrogen pulsed laser may be used to detect carbon—halogen bonds in organo—halogen compounds, products, and biological molecules containing such bonds.

In one embodiment, the excitation wavelength of the laser source 301, after doubling of the laser wavelength, may be about 255.3 nanometers or more. The frequency repetition may be about 10 KHz and the duration of the pulses may be about 10-100 nanoseconds, have a beam diameter of about 14 nm, and a divergence of about 0.5 mrad.

The instrument 300 may also include a crystal 302 that is coupled to the laser source 301. The crystal 302 may provide excitation in the UV region. A suitable crystal may be a $BaB_2O_4$ crystal. A spectrometer 303, such as a single, double, or triple monochromater, may also be included in the instrument 300. The spectrometer 303 may be suitable for use in the UV and VIS regions. An interference filter may be used instead of the spectrometer 303. The spectrometer 303 may have a slit of about 25-50 microns, with grooves of 1200-2400 lines/mm, be equipped with drive controls and other controls 312, including a stepping motor. The instrument 300 may also include one or more fibers 305 and a sample holder 302. The fiber 305 may be an optical fiber. The fiber 305 may be a bundle of fibers. The fiber 305 may be multifurcated (i.e. have one or more branches), and the fiber 305 may include a probe 317 coupled to an end of each branch to sense secondary emissions emitted from the sample. The probe 317 and the fiber 305 may be made of quartz and transmit VIS and UV radiation to a sample. The probes 317 may be optical probes, and may have different lengths. Each probe may also provide different time delays discussed below.

In one embodiment, for UV applications, light from the source 301 with a suitable wavelength may pass through the crystal 302. The output of the crystal 302 may then pass through a device 315, such as a dielectric mirror, to focus a beam on the sample. For applications in the VIS region, the signal from the source 301 may be applied directly to the sample without the need of crystal 302. Exposed to the radiation from the laser source 301, the sample may emit secondary emissions, which are sensed by one or more of the probes, 317. The fiber 305 transports the emissions to an entrance of a spectrometer 303.

Emissions introduced to the spectrometer 303 may then be delivered to a detector 304, such as photomultiplier. The detector 304 may also be a CCD configured to operate in the range of about 200-800 nm. The detector 304 may be used in UV and VIS applications. A power supply 320 may be coupled to and supply a voltage to the detector 304. The supply 320 may be, for example, a thyratron device. The resulting signal from the detector 304 may then be delivered to an amplifier 309, e.g., a stroboscopic amplifier, which translates emissions for processing by a data processing device 310.

The device 315 may also include a splitter to direct a portion of the beam from he laser source 301 to a photodiode 306 for collecting the radiation. The radiation is then passed to a time gating device 307 and a time delay device 308 to generate a pulse, such as a stroboscopic pulse 308a, to synchronize the detector 304 using device 310. The time delay and time gating devices enhance the sensitivity of detection and allow fluorescence and Raleigh emissions to be virtually eliminated.

In one embodiment, the time delay device 308 and the time gating device 308 may be used to provide time delays in the range of about 0-200 ns with time gates of about 1-10 ns. The time delay device 308 may provide between 0-100 ms time delays. The measured spectral range may be about 0-3000 $cm^{-1}$. The instrument 301 may also be timed for a specified carbon—halogen characteristic of about 500-900 $cm^{-1}$.

In an embodiment, the fiber 305 and/or the probe 317 may be used to obtain Raman, resonance Raman, surface enhanced Raman, and surface enhanced resonance Raman signatures, and to perform 1D-, 2D-, 3D-Raman measurements with a high level of sensitivity in the UV and VIS regions. The sensitivity may be about $10^{-15}$ grams or lower. For PLISERS applications, a fiber optic probe (FIG. 20) may be used.

In one embodiment, the device 310 maybe used to cause the instrument 300 to measure Raman emissions from the sample before the emitted fluorescence. In another embodiment, the fluorescence emission may be measured after the Raman emission. The device 310 may also store characteristics of different compounds, molecules, biological products, and other sources of the sample for comparison and identification.

Figure 19:
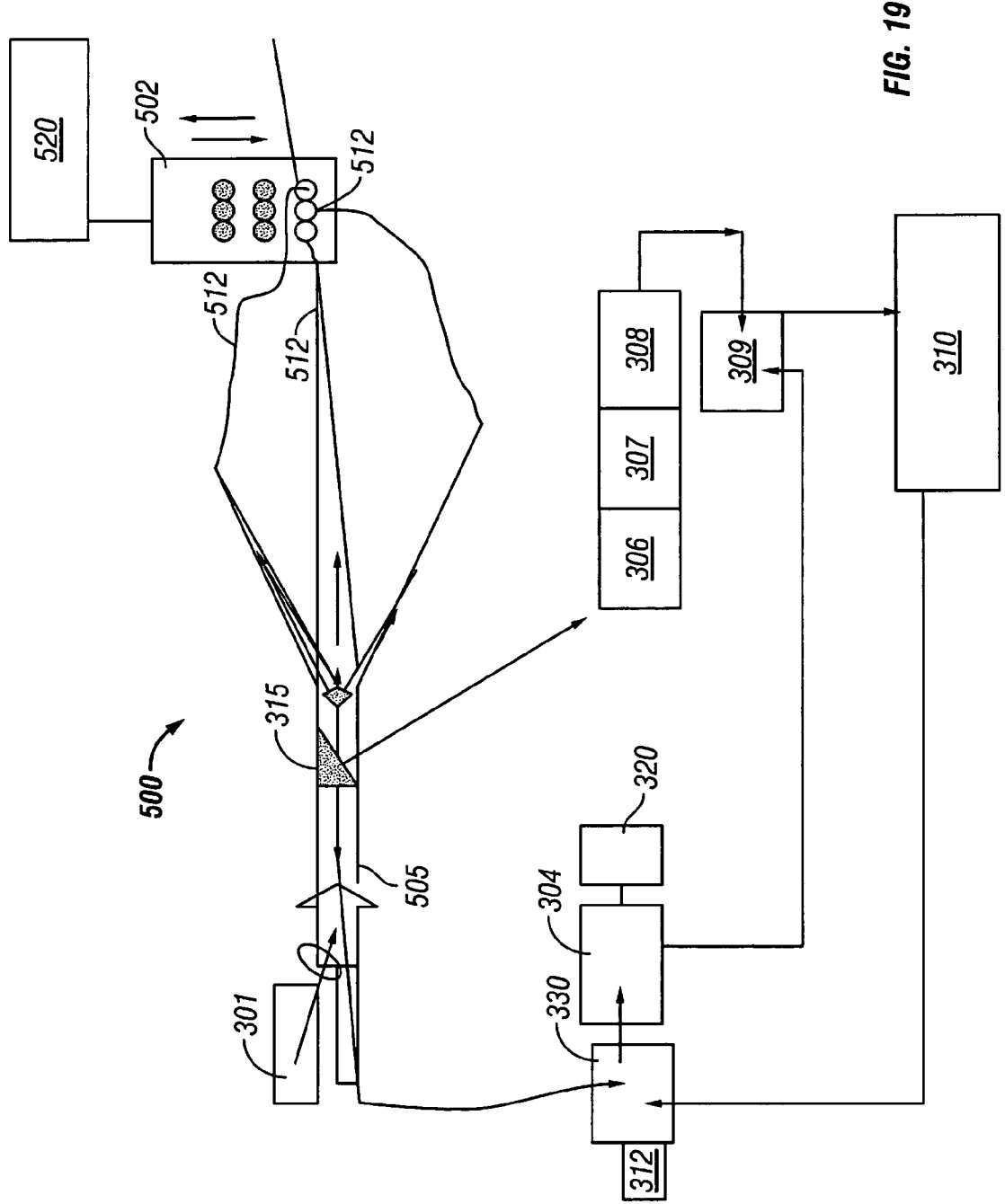
FIG. 19 is a schematic drawing of an instrument in a third embodiment.

To perform 2D- and 3D- measurements, the fiber 305 may include branches, each with one or more probes 317 of different lengths, e.g., bifurcations, trifurcations, or multifurcations, that transmit UV or VIS radiation may be used. The probes 317 and/or the fiber 305 may be coupled to be sample holder 330 at different points. In this case, measurements may be made by using different probe lengths and by changing the respective time delay lengths for each probe or branch. The space resolution of the Raman 2D-, 3D- mapping may depend on a diameter of the fiber and/or probe and the duration of the laser. FIG. 19 illustrates an instrument 500, that may be similar to instrument 300. However, the instrument 500 may also include a sample holder 502 and a stepping motor 520. The stepping motor 520 may be coupled to the sample holder 502 to move the sample holder 502. The instrument 500 may also include a fiber 505 similar to fiber 305. One or more probes 512 may also be coupled to the fiber 505. The sample holder 502 may hold any number of samples of different shapes and sizes depending on the application. In one embodiment, each sample may have a dedicated probe. In another embodiment, the number of probes may be less than the number of samples.

Figure 20:
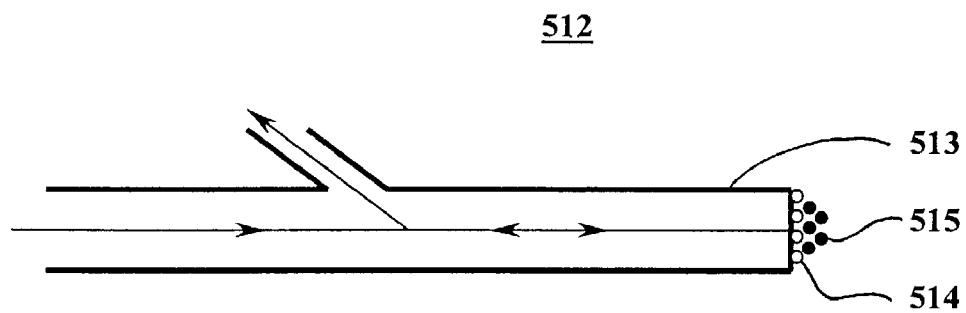
FIG. 20 illustrates a probe in an embodiment.

FIG. 20 illustrates an embodiment of a probe 512 for use with PLISERS applications. The probe 512 may be coupled to the laser source and may include a polished tip 513, which may be coated with one or more nobel metal islands (shown in white circles) 514. The black circles 515 represent molecules of a sample to be analyzed. The probe may be positioned proximate the sample, and surface enhanced Raman scattering may occur proximate to the nobel metal inclusions The emissions from the sample may be transported via the probe 512 to the fiber 505.

Figure 18:
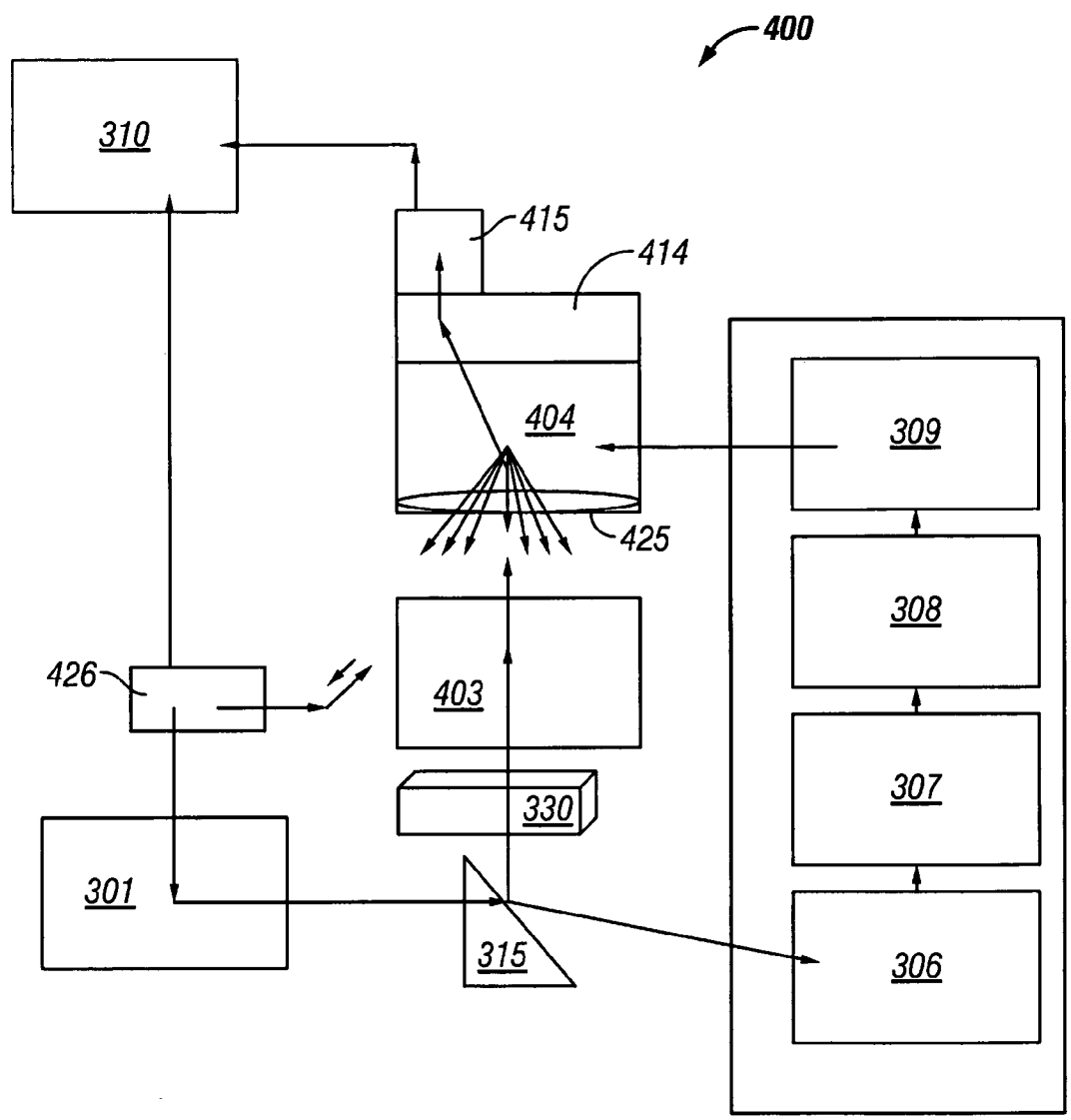
FIG. 18 illustrates a schematic drawing of an instrument in a second embodiment

FIG. 18 illustrates an instrument 400. The instrument 400 is similar to the instrument 300. However, the instrument may include a filter 403 such as a narrow band filter, angled away or toward the sample. Emissions passed through the filter are detected using an imaging device 404, such as a digital camera. In one embodiment, the device 404 may include a data transmission device 415, such as an IR transmitter. The device may also include a memory 414 to store spectral data. The device 404 may also include a telescopic lens 425, and may be positioned a distance away from the filter 403, for example, 1-3 meters. The instrument 400 may also include a controller 426, such as a stepping motor.

Organofluorine compounds may be analyzed using a characteristic Raman signature of a carbon halogen bond, such as a carbon-fluorine ("C—F") bond. One or more of the instrument 300, 400, or 500 may be used depending on the application (PLIR, PLIF, or PLISERS). In the case of solutions or mixtures, the intensity of the signature emission of the C—F bond may be directly proportional to the concentration of the organofluorine compound.Using the time-delay device and the time-gating device, impurities or additional molecules may be suppressed or differentiated from the characteristic signature of the C—F bond to analyze other components. The analysis may be performed by detecting the C—F bond through its Raman characteristic signal rather than detecting the presence of the entire organo fluorine compound or its fragments. In one embodiment, such an analysis may be used to determine the concentration of a compound or molecule by measuring an intensity of a marker band. In this case, the relative Raman intensity of the C—F bond may be directly proportional to the concentration of the compound.

Figure 21:
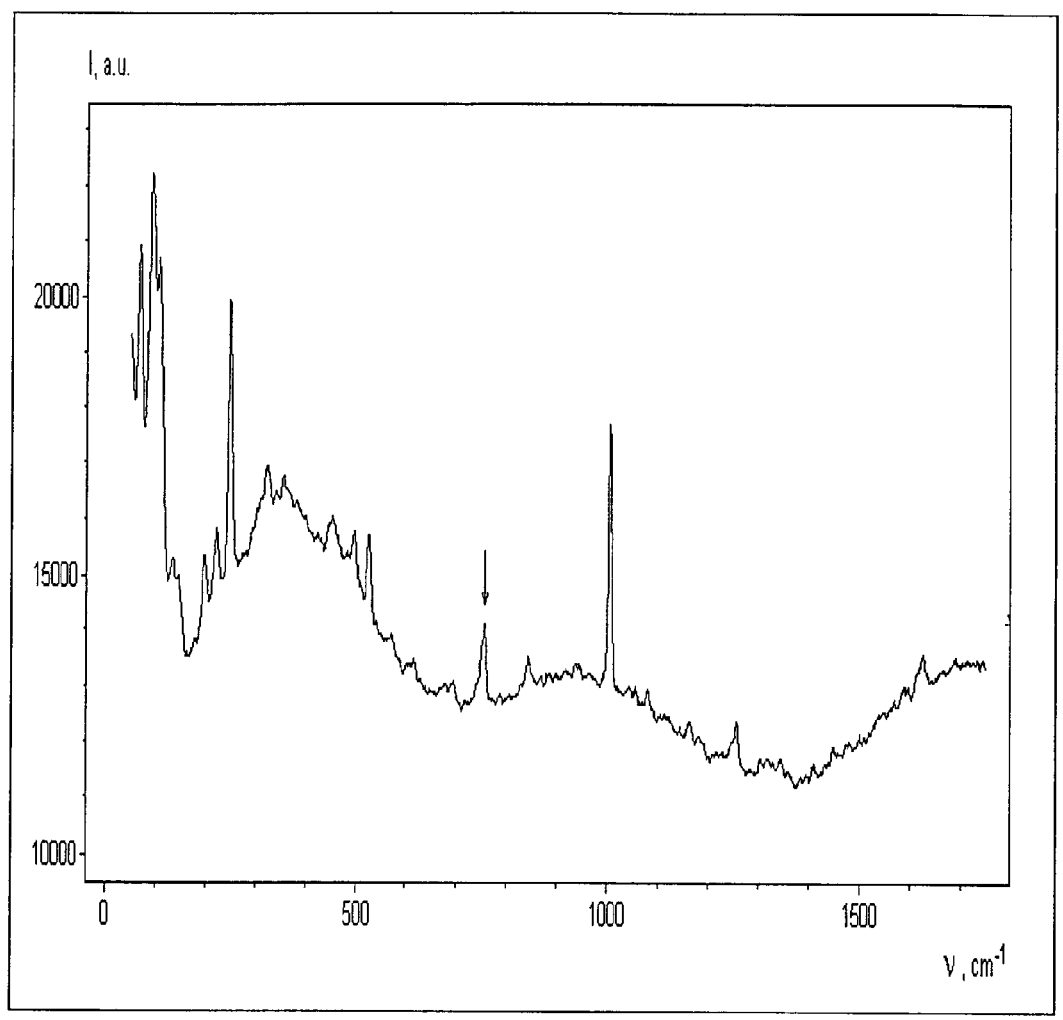
FIG. 21 illustrates a spectrum of m-Fluoro-DL-phenylalanine
Figure 22:
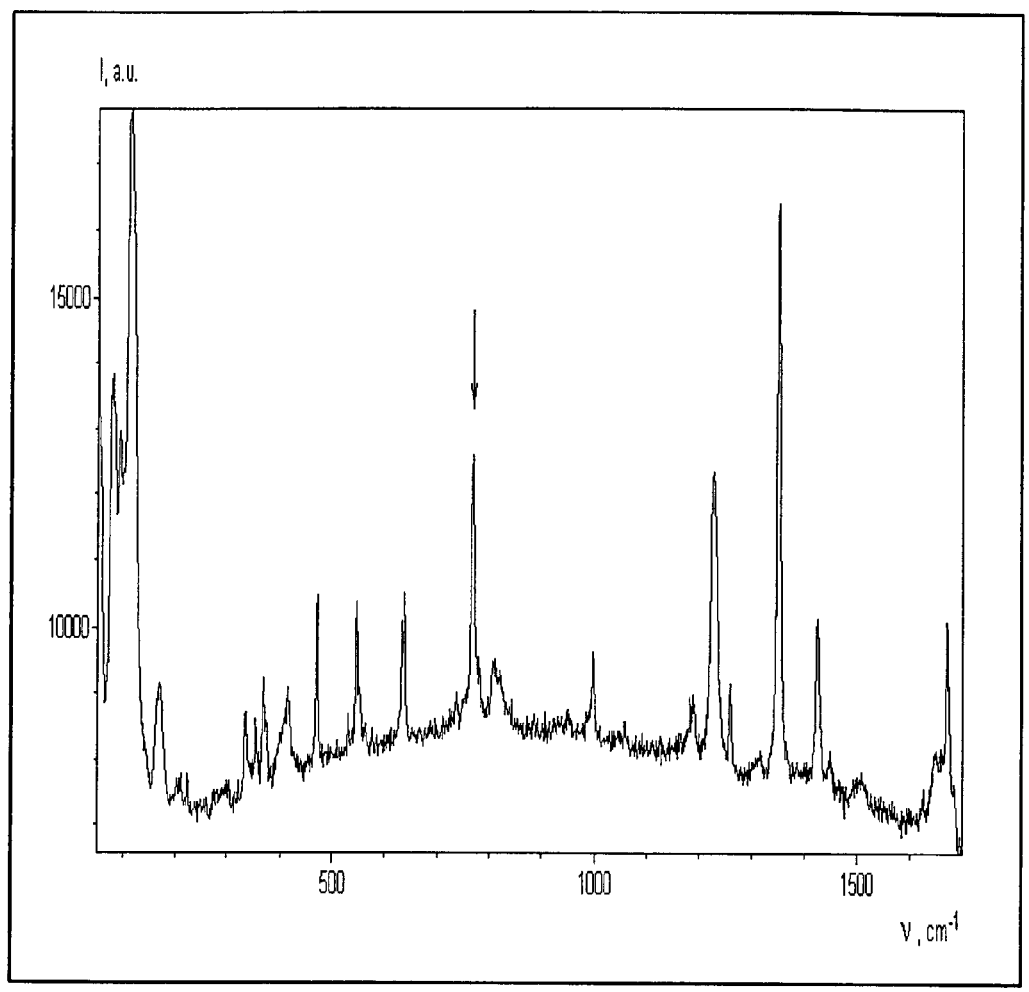
FIG. 22 illustrates a spectrum of 5-Fluoruracil.
Figure 23:
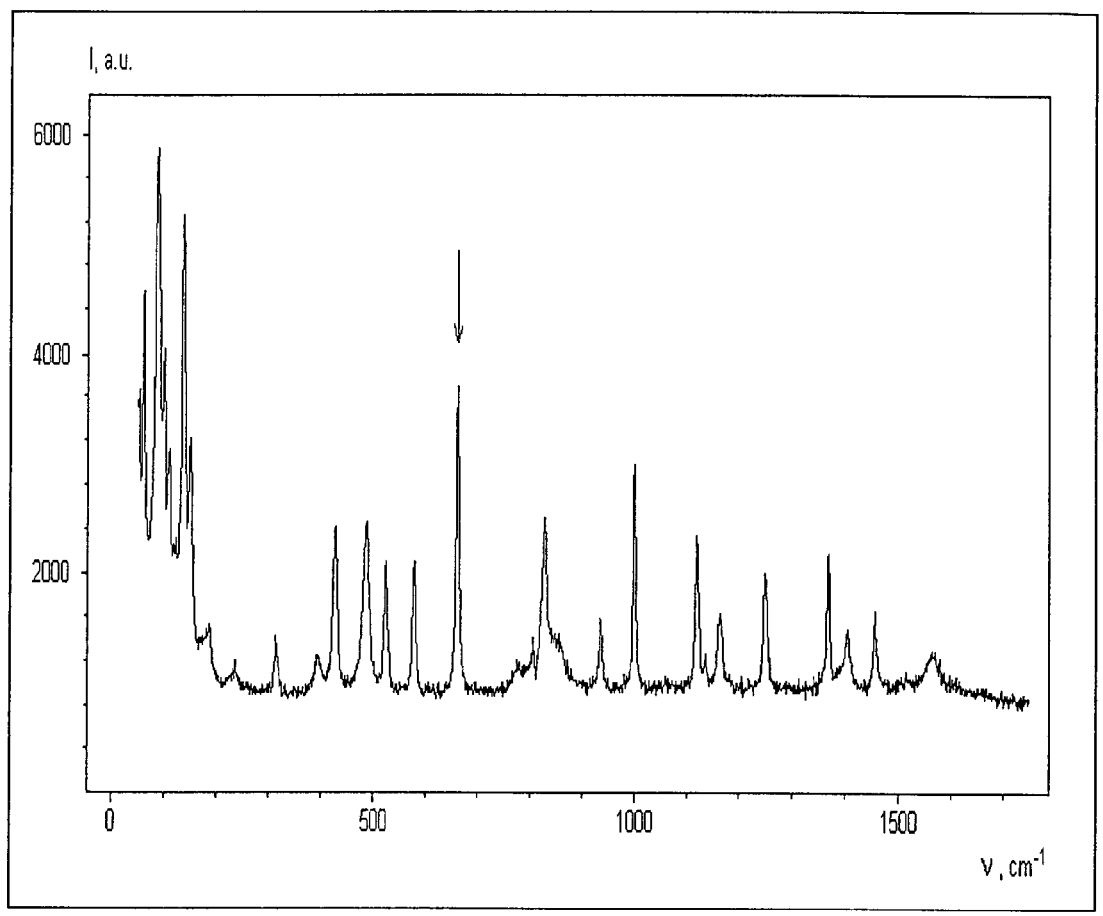
FIG. 23 illustrates a spectrum of B-Fluoropyruvic acid.
Figure 24:
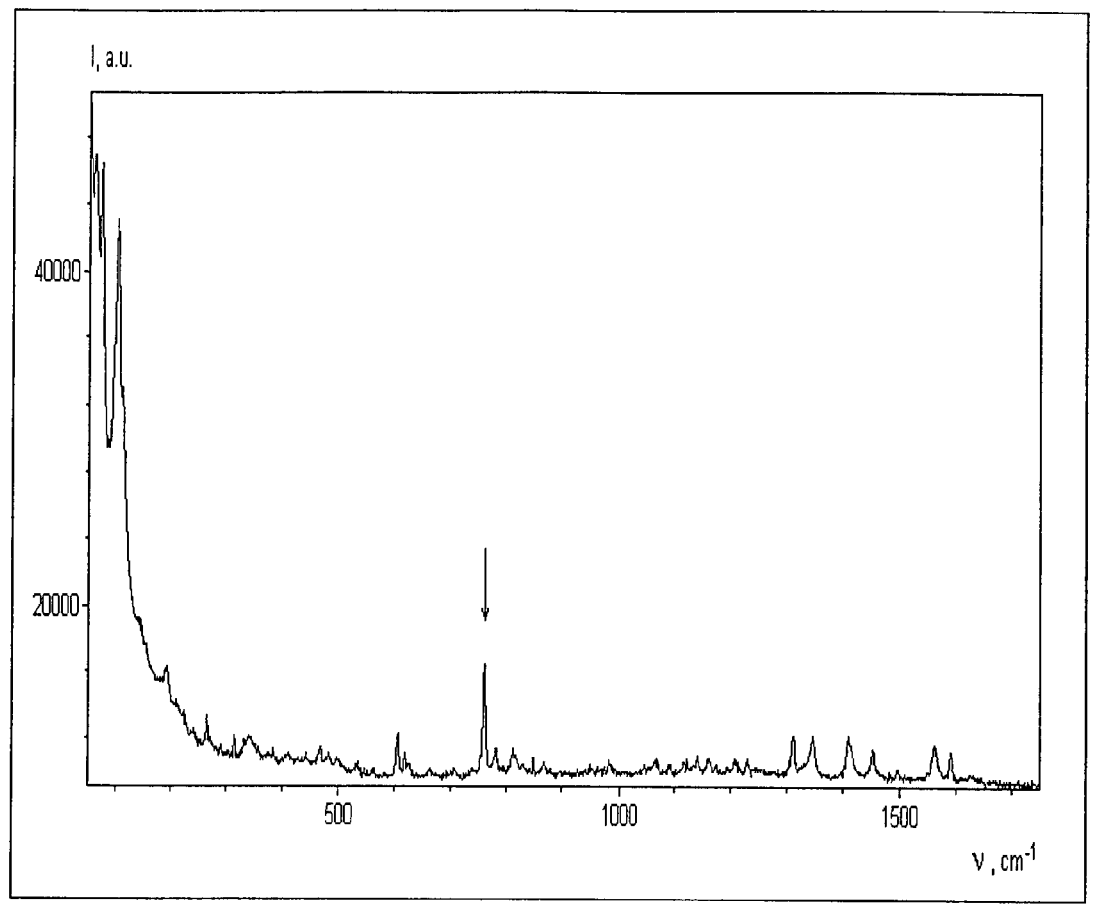
FIG. 24 illustrates a spectrum m-Fluoro-DL-Tryptophane.

The instrument 300, 400, 500 may be used to obtain PLIR spectra. For example, FIG. 21 and FIG. 24 show PLIR spectra for two solid fluoroamino acids, m-Fluoro-DL-phenylalanine and m-Fluoro-DL-Tryptophane. Such amino acids may also be detected when incorporated into peptides or proteins. Other examples include fluorinated compounds, such as 5-Fluorouracil (FIG. 22), 5-Fluoropyruvic acid (FIG. 23).

Figure 25:
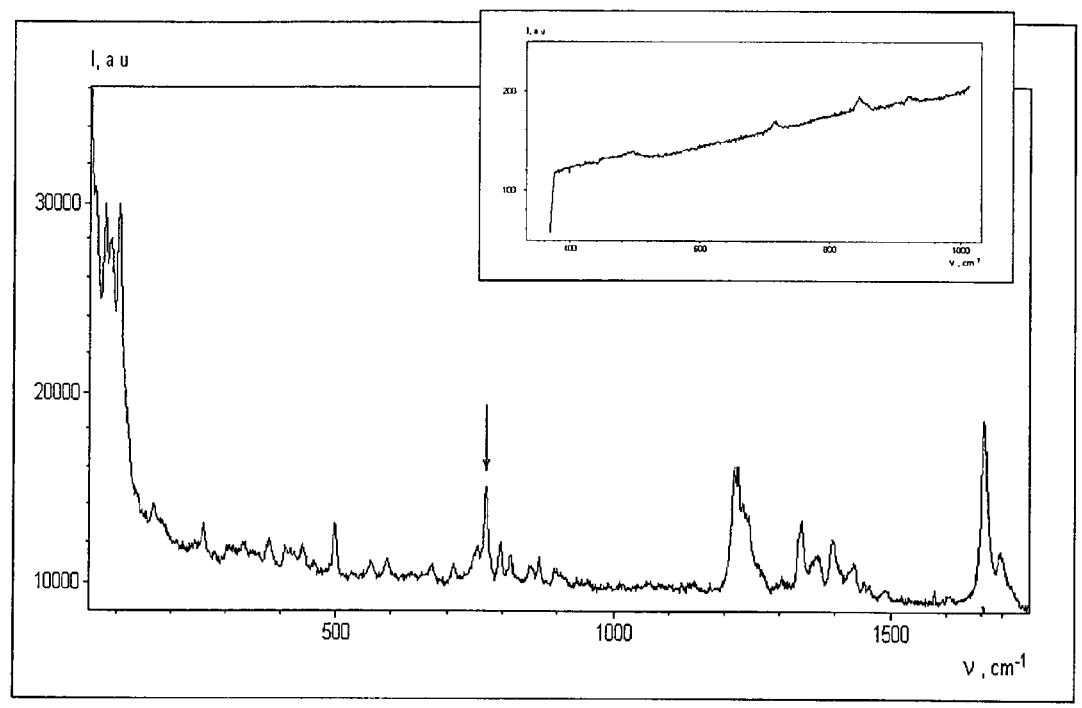
FIG. 25 illustrates a spectrum of 5-Fluorouridine.

FIG. 25 shows a PLIR spectra of 5-Fluorouridine, which may be recorded with the instrument 400 configured with a double monochromator, pulsed copper vapor laser with an excitation wavelength at 510.6 nm, and 100 mW of average power. The spectra reveals a characteristic signature of a C—F bond of about 700 $cm^{-1}$.

Figure 26:
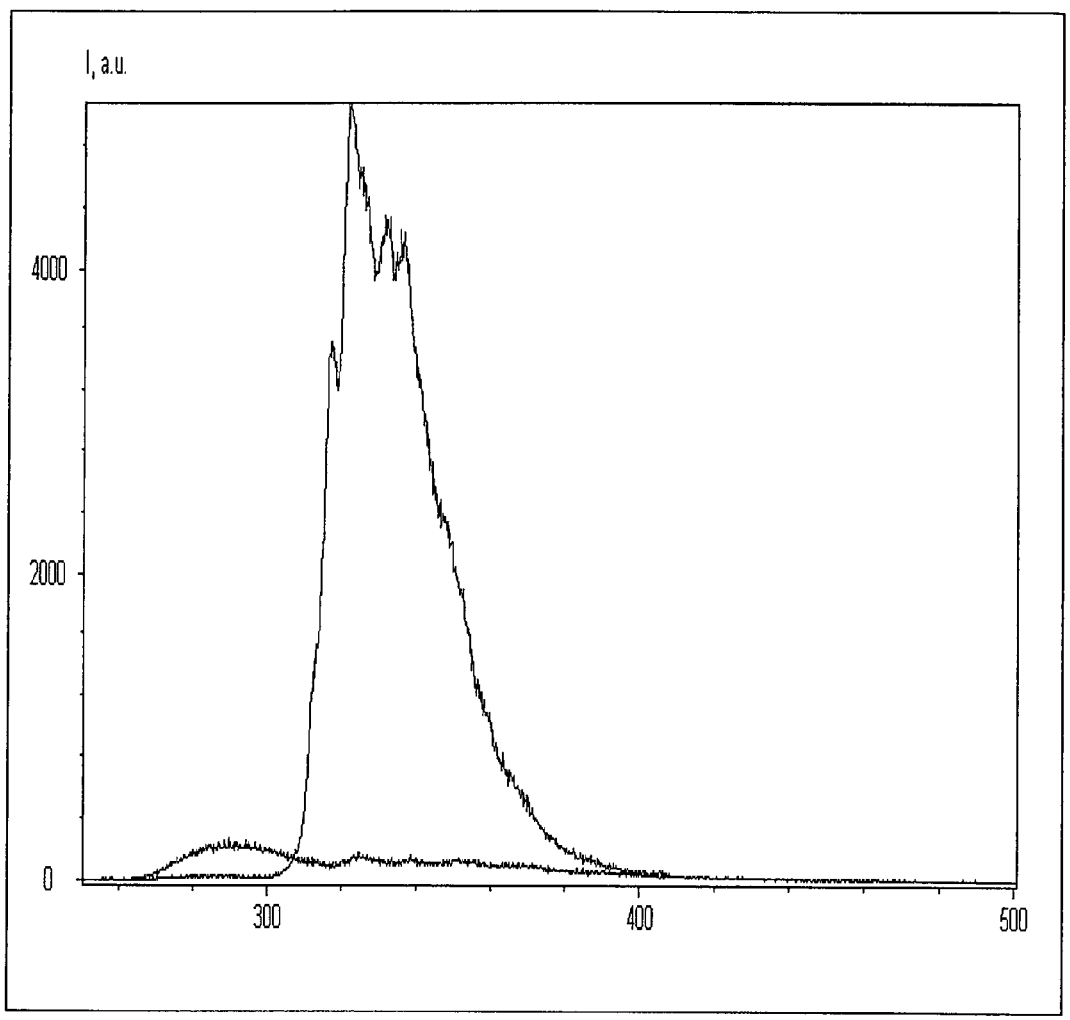
FIG. 26 illustrates spectra of naphthaline with zero delay and $C_9F_{21}N$ with a 50 ns delay.
Figure 27:
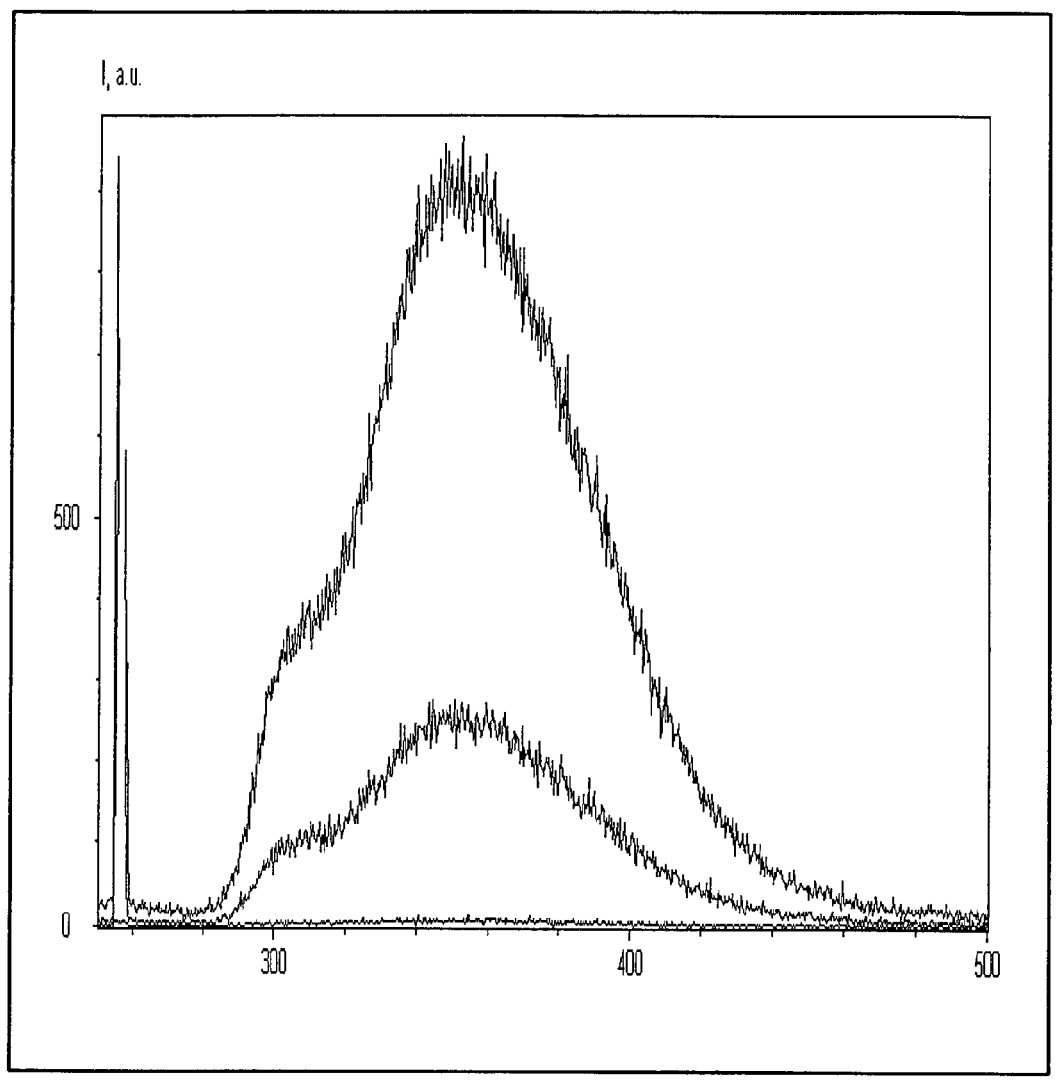
FIG. 27 illustrates spectra of D-Tyrosine at different time delays.
Figure 28:
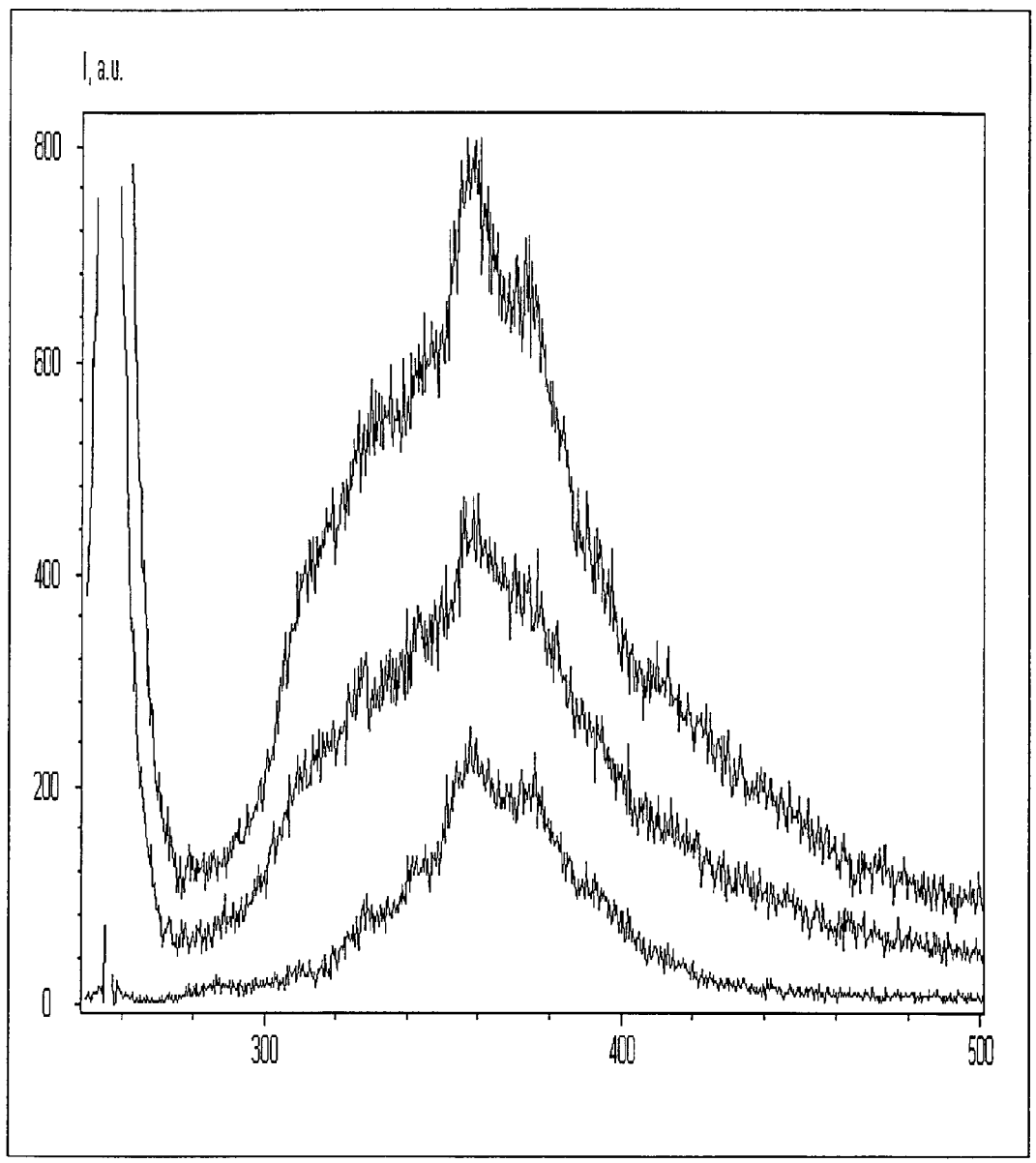
FIG. 28 illustrates spectra of m-Fluoro-D-Tyrosine at different time delays.
Figure 29:
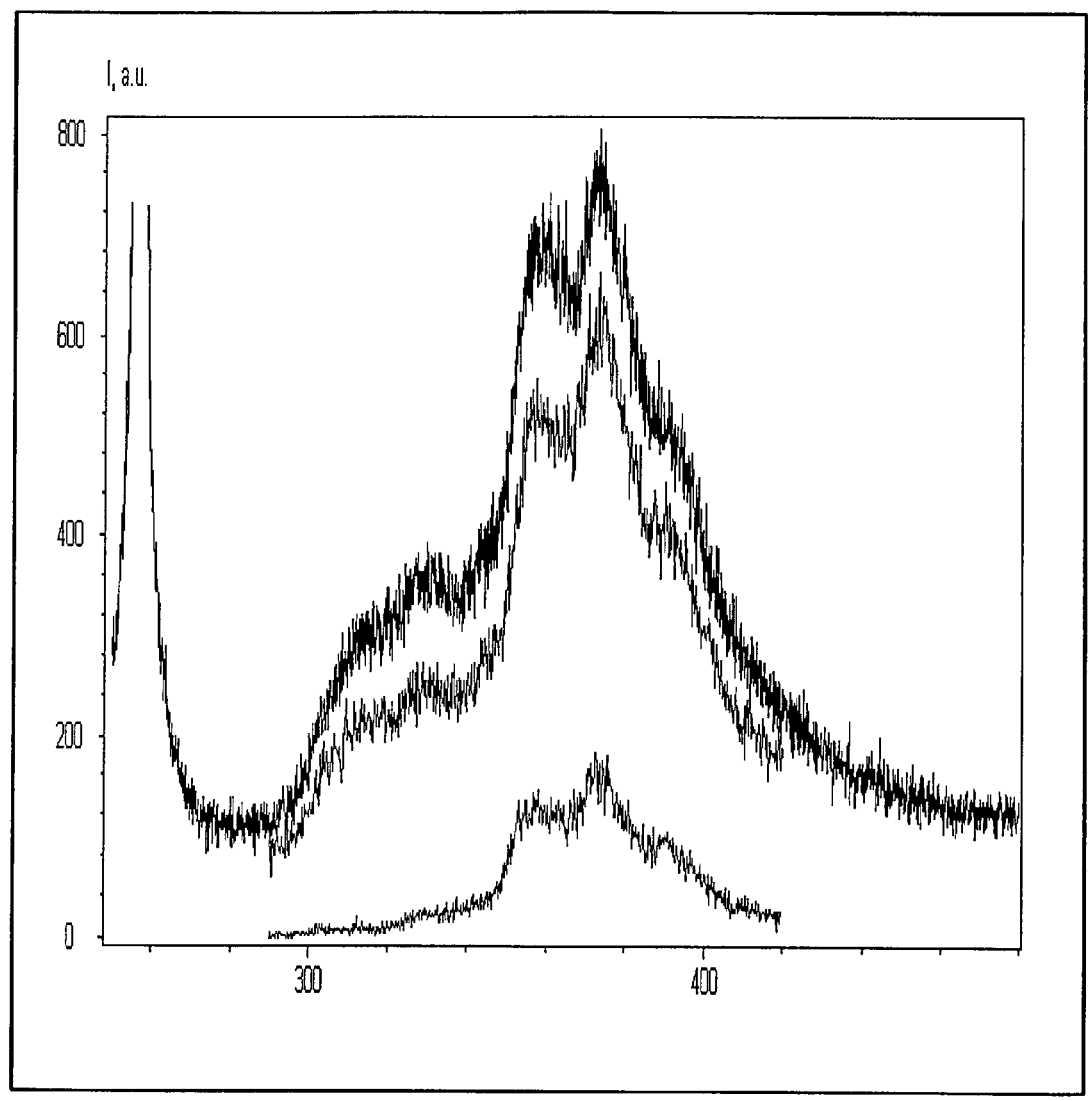
FIG. 29 illustrates spectra of Chicken DNA.
Figure 30:
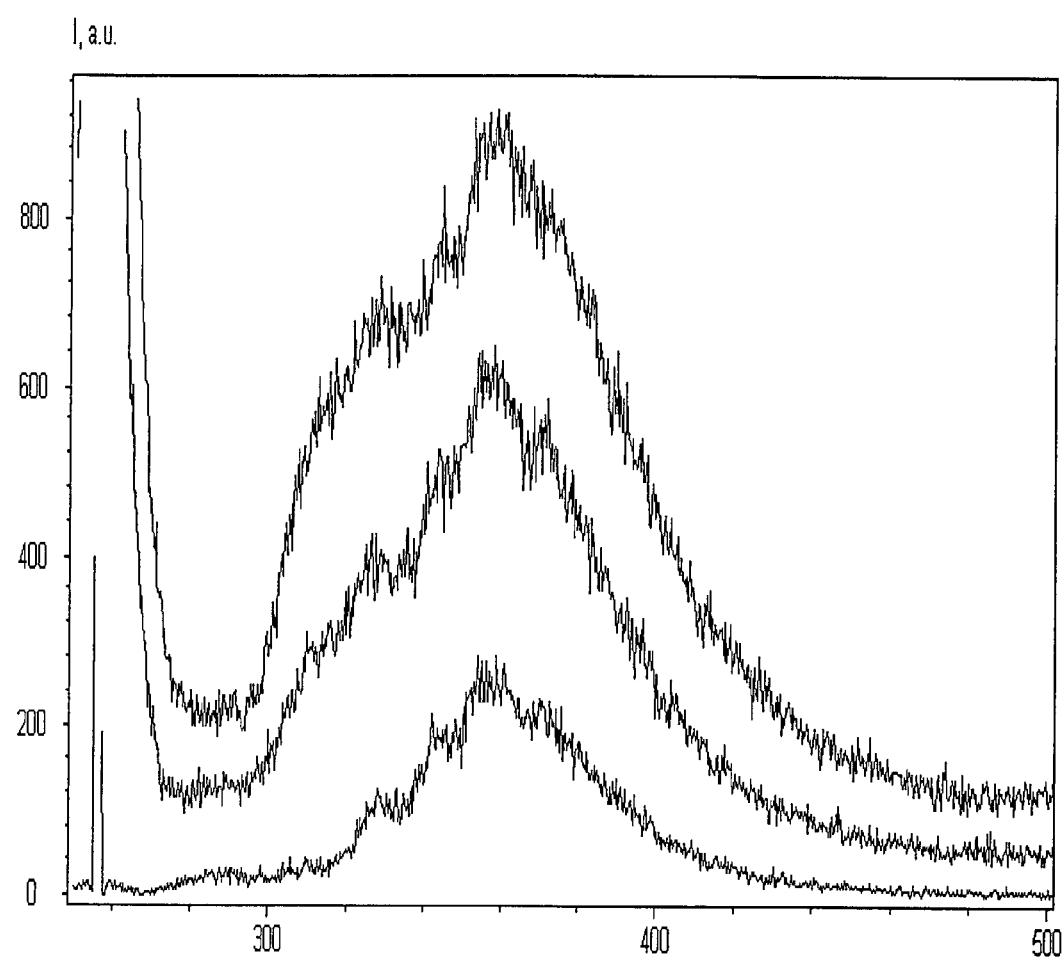
FIG. 30 illustrates spectra of 5-Fluoro-Uridine water solution.
Figure 31:
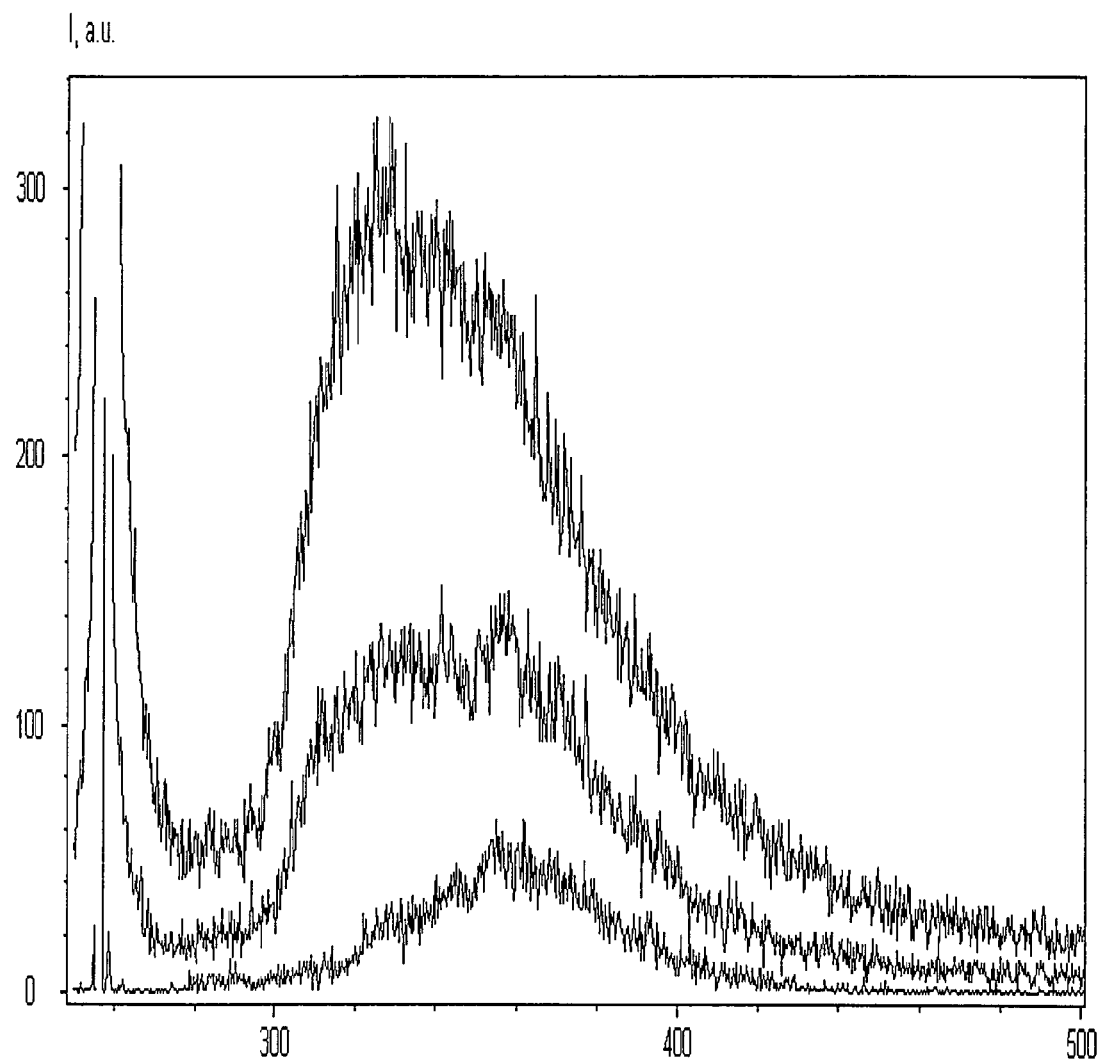
FIG. 31 illustrates spectra of 5-Fluoro-Uridine solid at different time delays.
Figure 32:
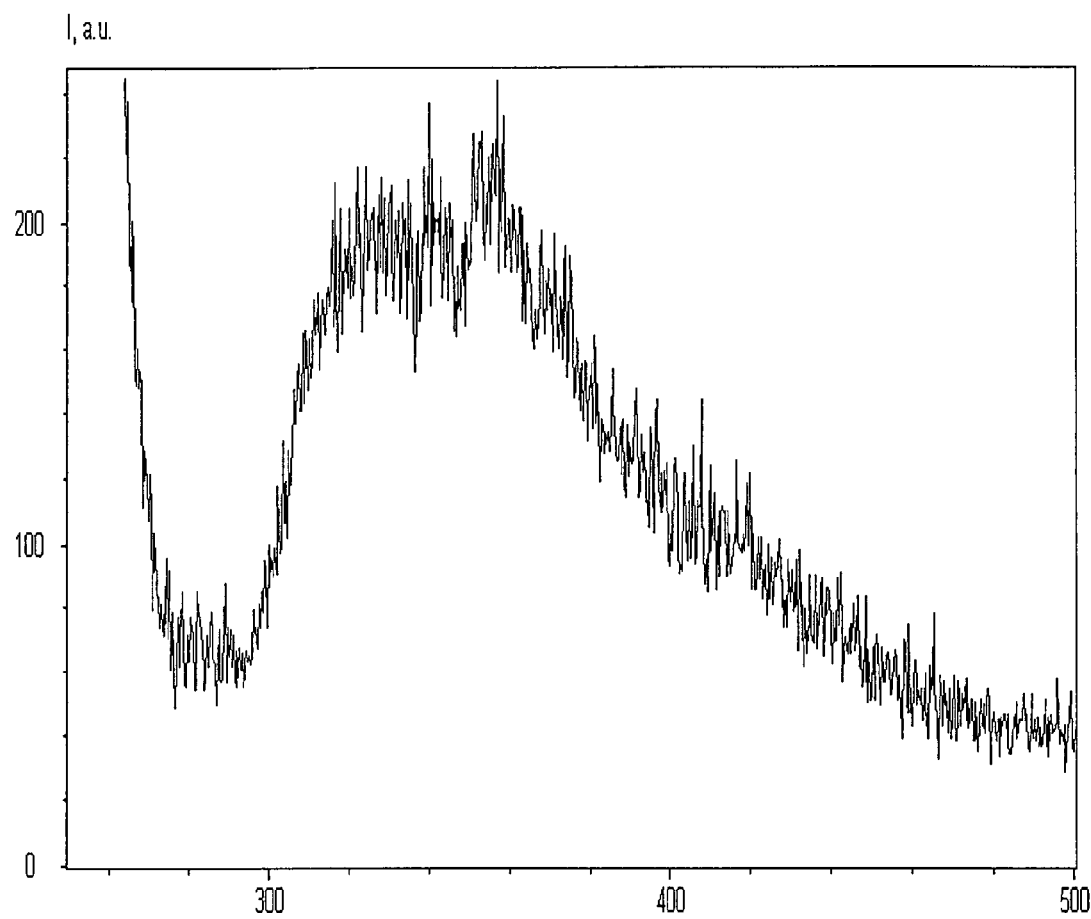
FIG. 32 illustrates a spectrum of 5-Fluoro-Uridine film after a water solution evaporation with a zero time delay.
Figure 33:
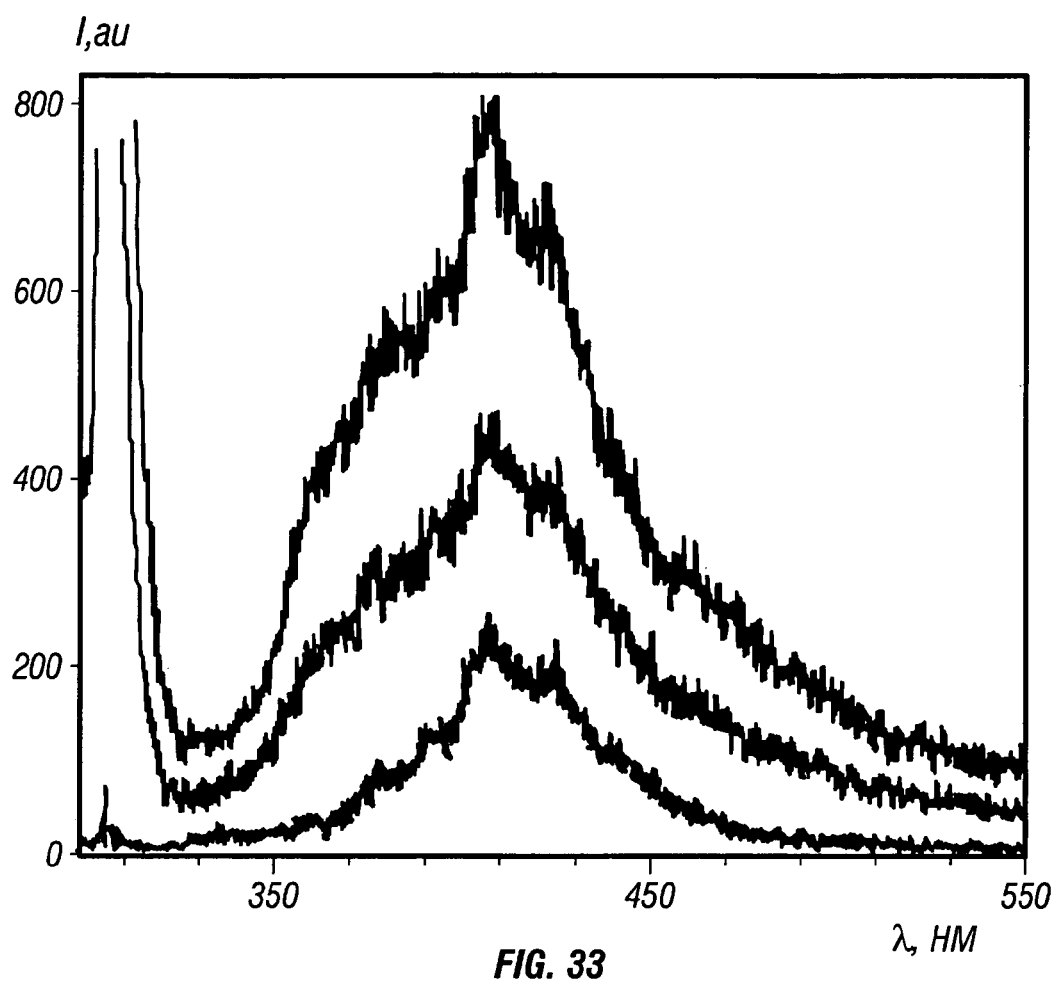
FIG. 33 illustrates spectra of D-Tyrosine at different time delays.
Figure 34:
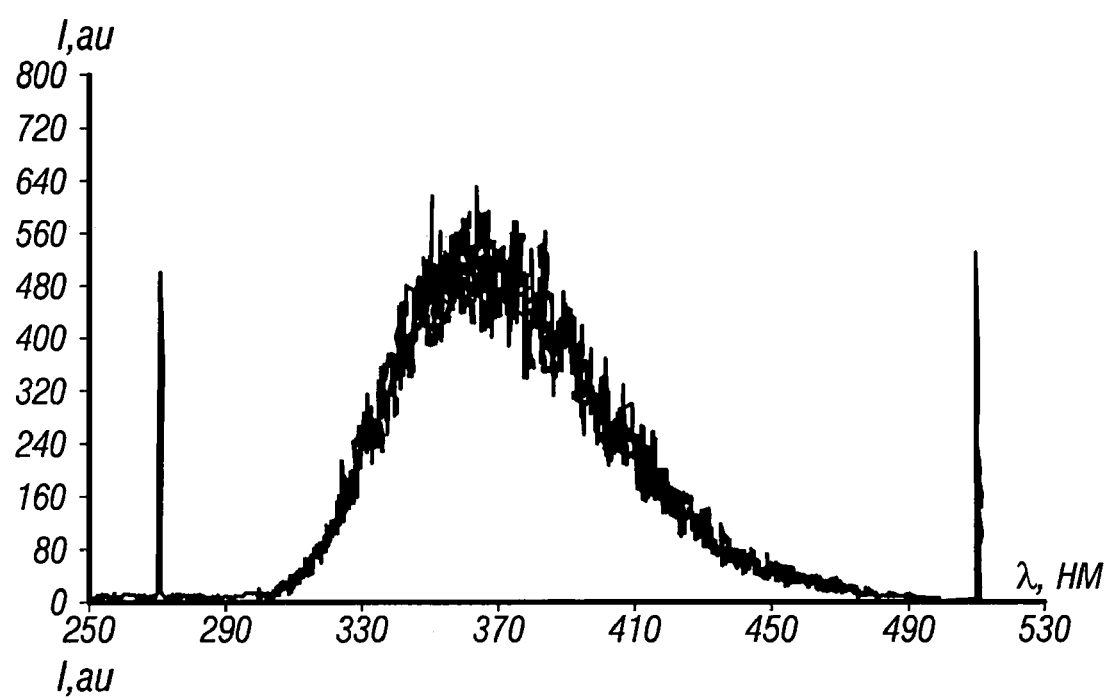
FIG. 34 illustrates a spectrum of F-modified Tryptophane with a zero time delay.

PLIF spectra of various fluorinated and non-fluorinated biological molecules and samples may also be obtained using one or more of the instrument 300, 400, 500. Examples include PLIF spectra of a water solution (1 mg/L) of m-Fluoro-D-Tyrosine (FIG. 28), which may be recorded at different time delays and its natural analog, D-Tyrosine (1 mg/L) water solution, which is also recorded at different time-delays (FIG. 27). Other examples include solid film on a glass surface (spot size 100 microns) of 60 fg of 5-Fluorouridine (FIG. 32); Naphthaline with zero delay and $C_9F_{21}N$ with a 50 ns delay; (FIG. 26); F-modified Tryptophane at zero time delay (FIG. 34); micron-size solid particles of 5-Fluorouridine (FIG. 31); 1 mg/L water solution of 5-Fluorouridine (FIG. 30); F-modified m-Fluoro-D-Tyrosine and regular D-Tyrosine at different concentrations and time-delays (FIGS. 28 and 33); and a $10^{-6}$ g/mL solution of Chicken DNA (FIG. 29) taken at different time-delays.

Figure 37:
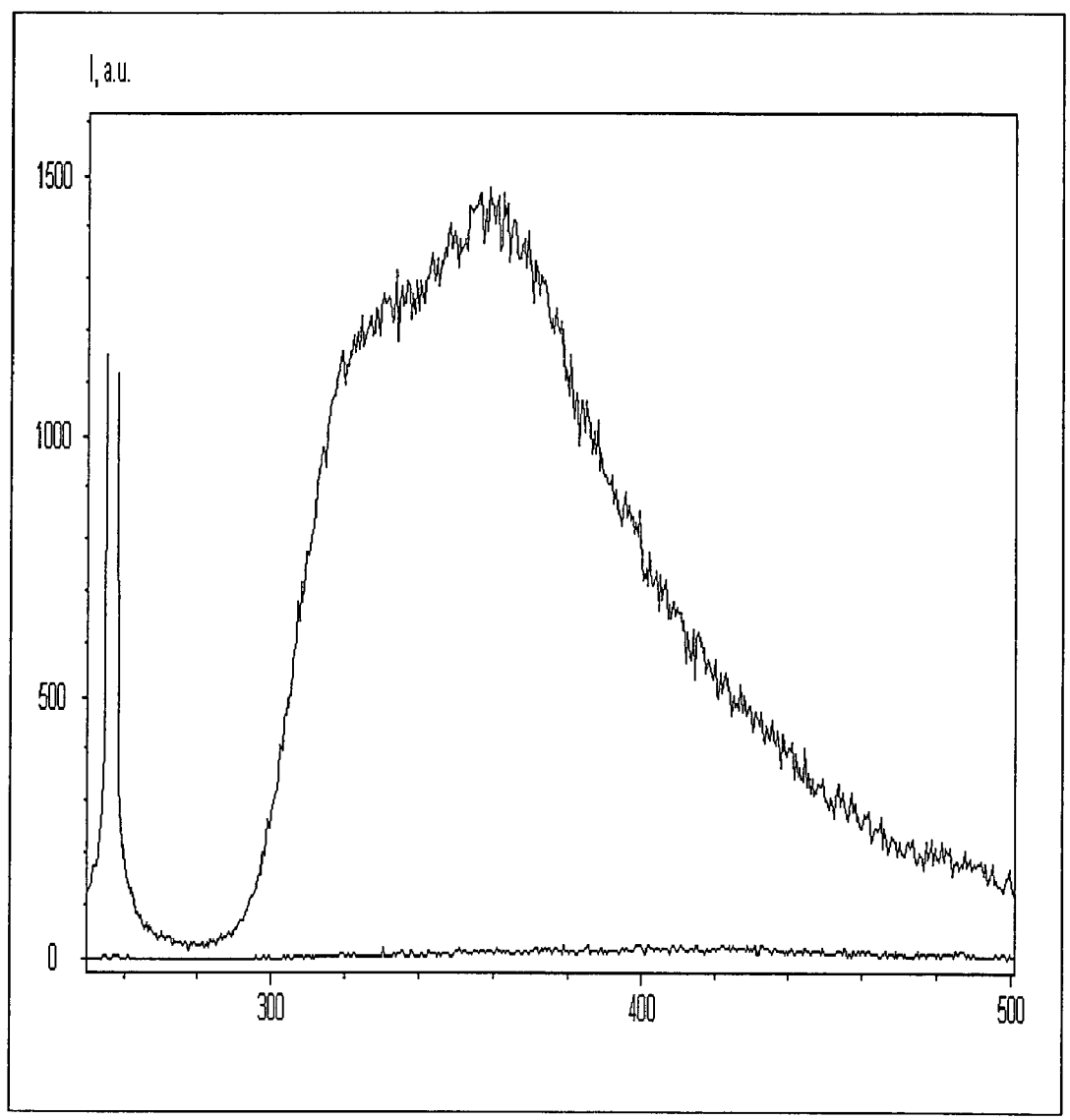
FIG. 37 illustrates spectra of modified Soy at different time delays.
Figure 38:
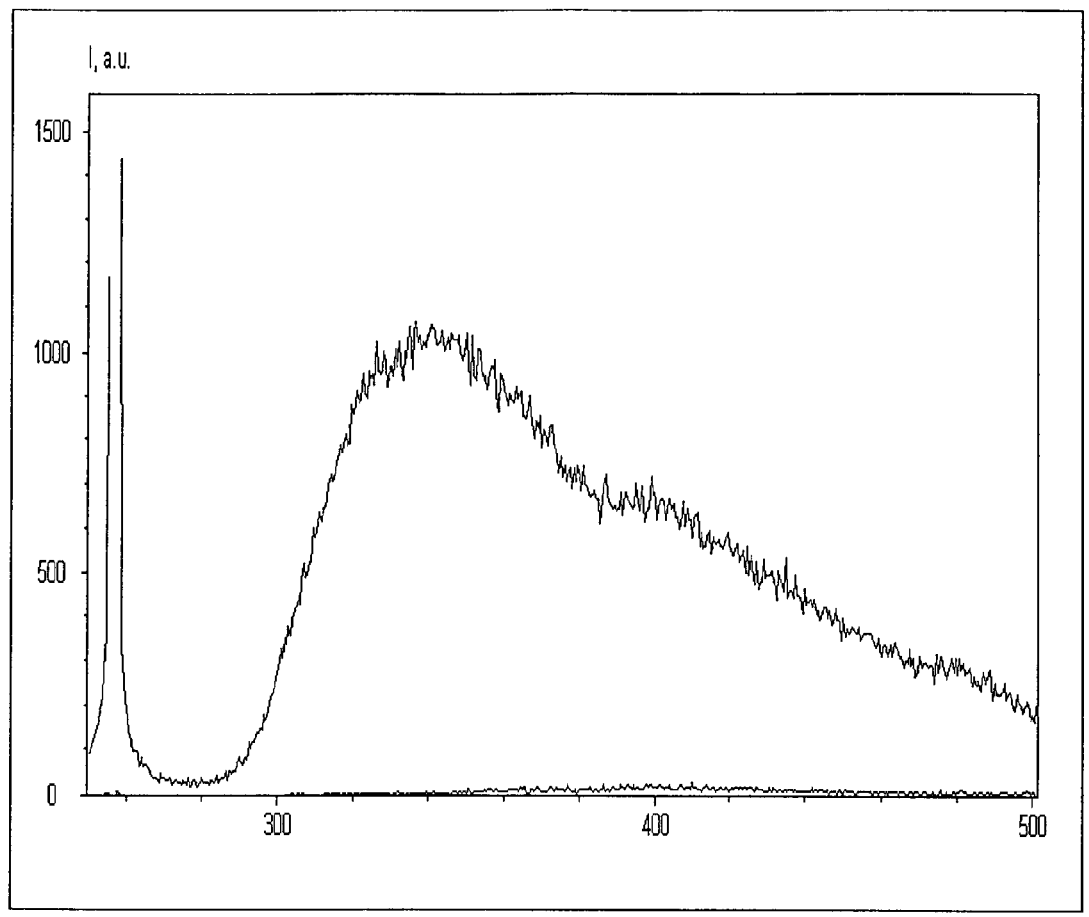
FIG. 38 illustrates spectra of unmodified Soy at different time delays.

In another example, natural and genetically modified PLIF spectra of Soy may be recorded for time delays of about 0-50 ns. (FIGS. 37 and 38). A difference in PLIF spectra between genetically and modified natural Soy may also be measured. In particular, the fluorescence intensity of genetically modified Soy may be higher than unmodified Soy, and the maximum fluorescence signal may be shifted along with the shape of the resulting curve. The Raman spectra also demonstrates the difference in the spectrum of modified and unmodified Soy.

Figure 35:
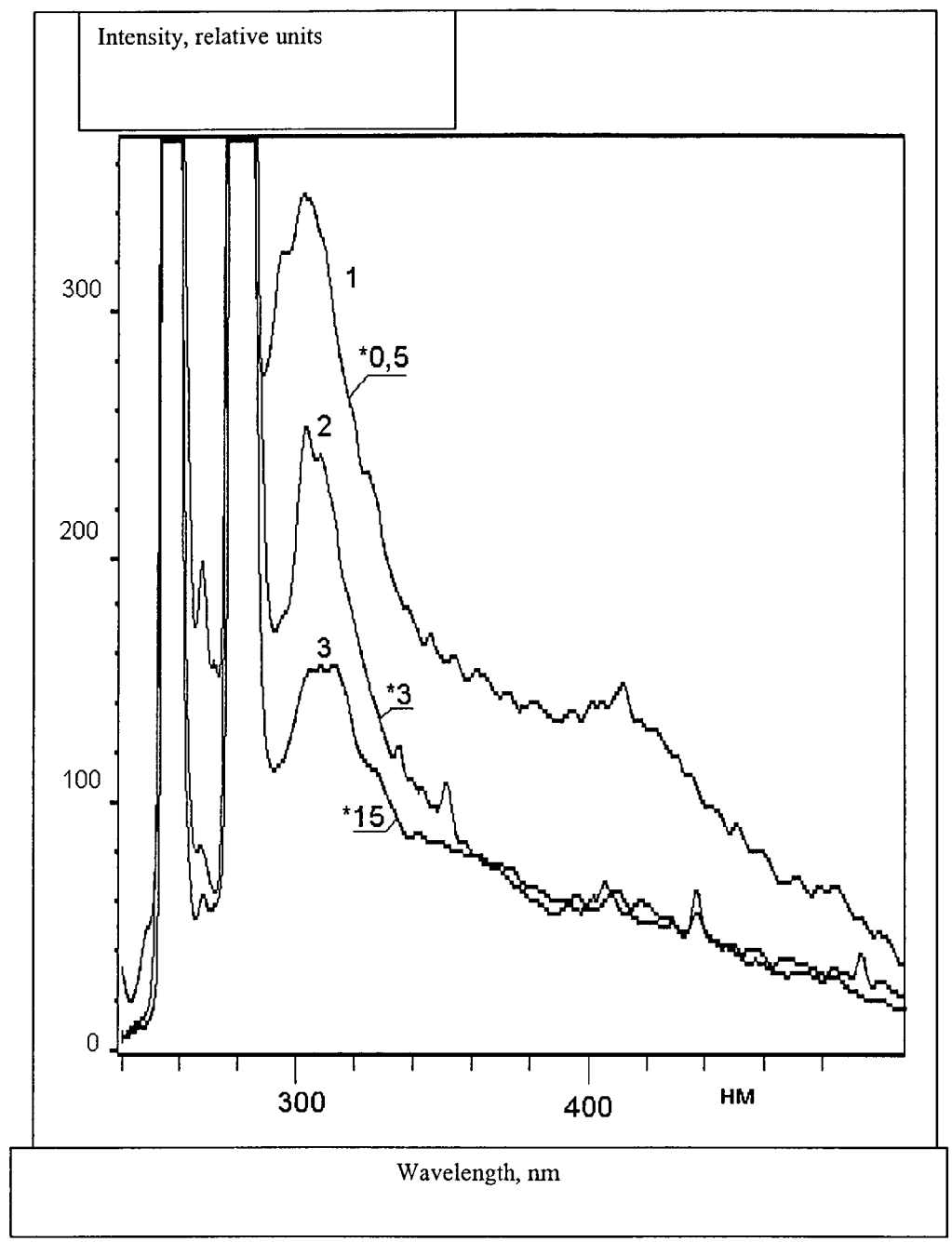
FIG. 35 illustrates spectra of *Bacillius Thuringiensus*.
Figure 36:
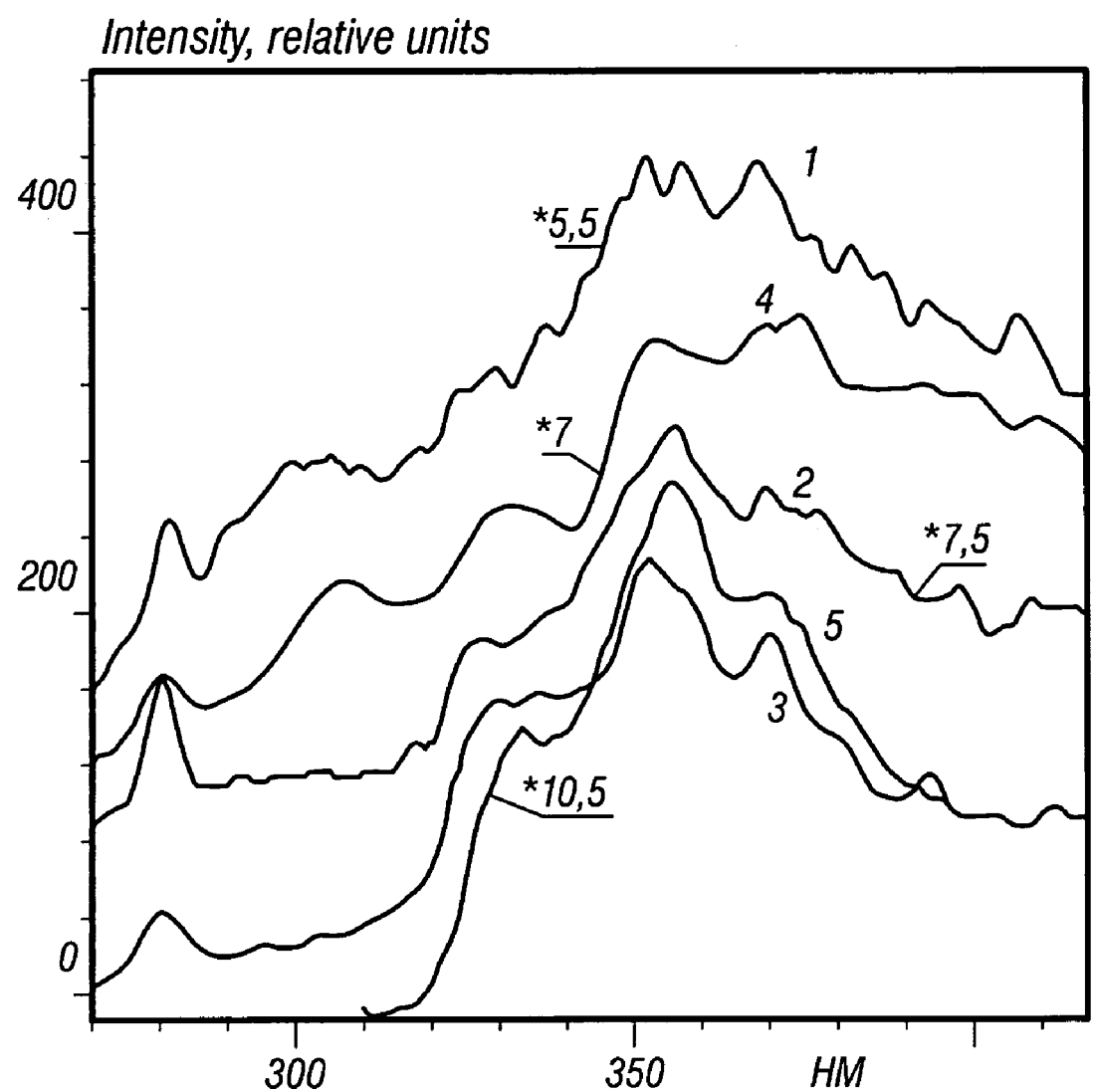
FIG. 36 illustrates spectra of *Bacterius Thuringiensus*.

Microorganisms may be directly detected in the field, soil, open or ambient air by using collected proceeds, e.g. filters, in water, foodstuffs, serum, biological fluids by recording PLIIR and PLIF spectral data. For example, FIGS. 35 and 36 show spectra for *Bacillius Thurigiensus* and *Bacterius Thuringeinsus*, respectively. This data may be compared with pre-recorded spectral libraries found in a data processing device, such as device 310. Time-gating device and time delay devices may be used to suppress background and fluorescence interference in a Raman mode. Fluorescent and resonance Raman spectra may be used to differentiate between microorganisms and their strains due to different patterns of decay in mixtures.

In one embodiment, detection of a carbon—halogen bond, such as a C—F bond, may be performed, when microorganisms and/or viruses are cultivated in or on growth-media, which contain different, small amounts of halogenated or fluorinated amino acids, nucleotides or fluorinated bases. During growth, C—F bonds may be incorporated as labels into the proteins and/or the nucleic acids of the microorganisms and viruses. This may result in different characteristic pulsed Raman and pulsed fluorescence spectra, which may be compared with the spectra of the unlabeled microorganisms and viruses. The changes of the C—F modified spectra in the pulsed Raman and the pulsed fluorescence mode may be used to differentiate strains of these microorganisms and viruses.

In another embodiment, a carbon—halogen labeled bioprobe, e.g., DNA/RNA-probes, peptides, proteins, monoclonal -, recombinant antibodies, aptamers, mirror-, photoaptamers (containing e.g. BrdU), ribozymes, and antisense-molecules, containing one or more carbon—halogen bonds, may be hybridized or bound to target-molecules in the cells, on the surface of these microorganisms/viruses, in their lysates, or by using specific nucleic acids and proteins that are characteristic of each virus or microorganism.

One or more carbon—halogen bonds, such as a C—F bond, may be attached to or incorporated into bioprobes. The bioprobes may be a nucleic acid or protein. The recorded spectra may be characteristic spectra of the C—F-modified bioprobe, which may be used in single samples or in a multiplex analysis. Spectra for the bound and unbound C—F modified bioprobes may be generated using an instrument, e.g., instrument 300, that indicate differences in Raman intensities and possible Raman shifts. The detection may be used for quantitative analysis. The characteristic signal of the C—F bond may be quantified because the relative intensity of an associated Raman C—F peak is directly proportional to the concentration of the analyte.

Figure 39:
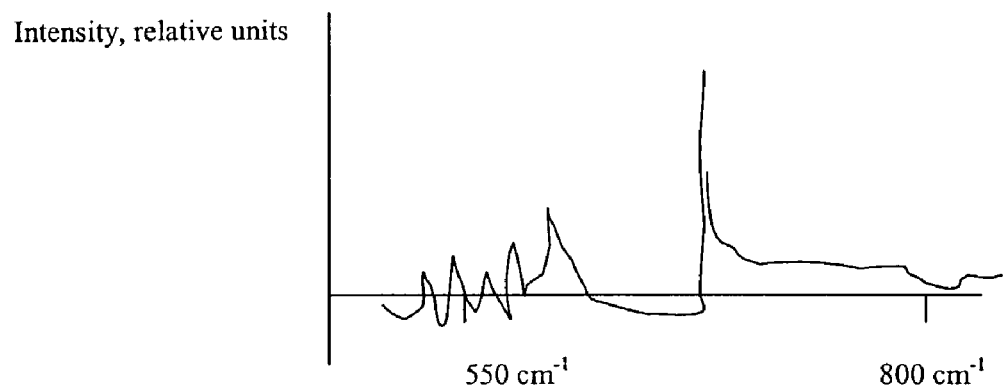
FIG. 39 illustrates a spectrum of a DNA (RNA) hybridization F-modified bioprobe.
Figure 40:
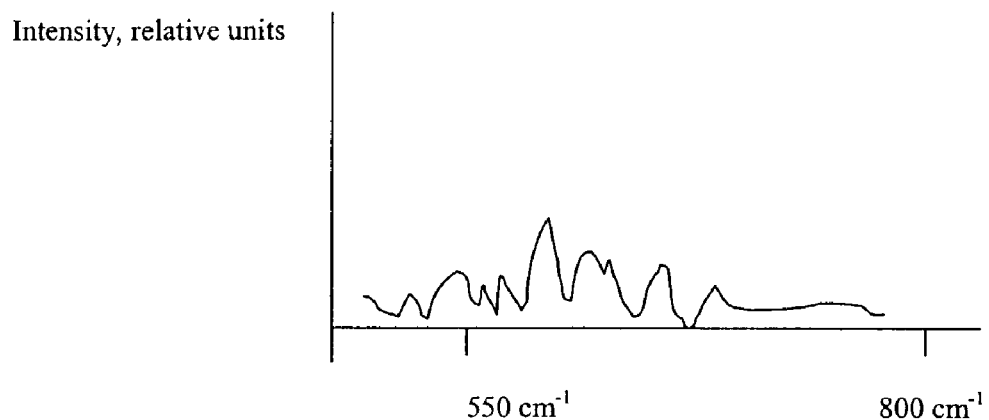
FIG. 40 illustrates a spectrum of an unlabelled DNA (RNA) sample.
Figure 41:
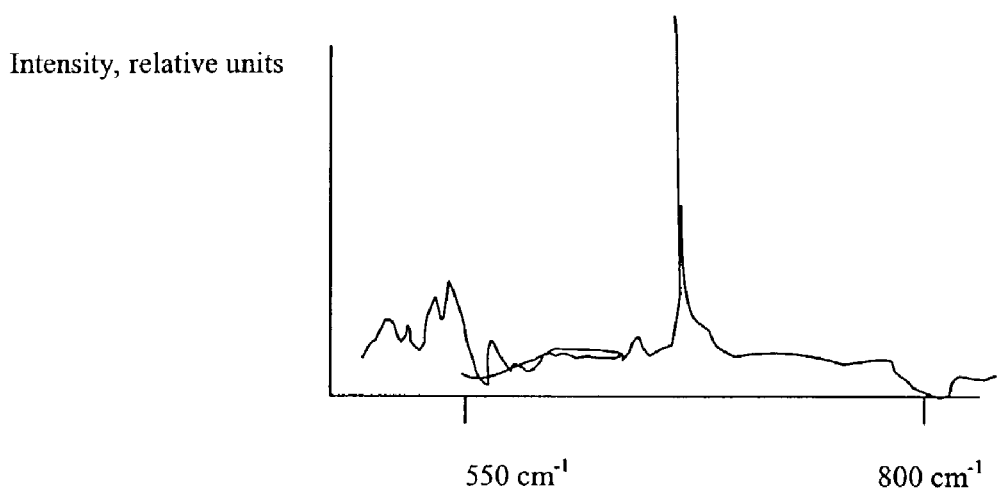
FIG. 41 illustrates a DNA (RNA) hybridized to a C—F labeled bioprobe.

FIG. 39 illustrates an example of a spectrum for a C—F-modified bioprobe. FIG. 40 illustrates a spectrum of an unmodified biologic. FIG. 41 illustrates an example of a spectrum for a hybridized or bound C—F bioprobe.

In an embodiment, the instrument 300, 400, 500 may be used in invasive and non-invasive applications to obtain Raman spectra to identify diseased or normal tissues, biopsies, or cells. The instrument may be used in combination or coupled to a surgical tool, such as a fiber optic probe; scalpel, catheter, or other similar device in order to record pulsed Raman and pulsed fluorescent spectra by rejecting strong background fluorescence. In another embodiment, carbon—halogen containing metabolic contrast media, e.g., Fluorinated Glucose, may be used to differentiate tissues with low fluorinated glucose turnover. Other carbon—halogen labeled chromophores, such as F-Tryptophan, F-Tyrosin, F-Uridin and Tifluoroleucine may be used to indicate a disease state when incorporated into nucleic acids or proteins. The generated spectra may be used to identify a malignancy. Alternatively, other C—F labeled biologics, drugs, or metabolites may be used for the identification of abnormal cells and tissues.

In another embodiment, genome and proteom data libraries may be used to identify specific gene sequences and/or proteins, which may be characteristic for the identification of disease!cancer cells or tissues under investigation with C—F labeled nucleic acid probes or C—F labeled immunologic markers. A selection against these targets may be made, and a synthesis of the carbon—halogen containing compound, drug, or biologic, which binds to specific known target molecules of the disease/malignant cells or tissues, may be chosen. Target gene sequences may be hybridized with their carbon—halogen modified DNA/RNA matching strands, peptides, nucleic acids, antisense molecules, and ribozymes. Target proteins may be bound to peptides, proteins, antibodies, or aptamers either in tissues, cells, or after their isolation in solution or on surfaces.

Raman spectra of unlabeled tissues, cells and of each of the matching carbon—halogen modified bioprobes, e.g., a C—F modified bioprobe, may have to be pre-recorded before reacting with each other. This may result in specific spectra of the unlabeled tissues or target molecules, and of each carbon halogen modified bioprobe. These modified bioprobes may also be quantifiable due to the direct dependency between the relative intensity of the C—F peak and the concentration of each bioprobe. After the reaction/hybridization takes place, the Raman spectra of the bound and unbound C—F labeled bioprobe may then be recorded. The Raman signal for the C—F bond may shift to a higher frequency, when the C—F modified bioprobe is bound.

In another embodiment, diseases may be diagnosed by using a laser source with a lasing media of a mixture of copper and gold metal vapor, a lead vapor laser, or a barium metal vapor. Such laser sources may produce wavelengths in the red, green, and yellow region. Such lasers may have a wavelength of about 500-800 nm. The instrument 300, 400, 500 may include a probe made from, for example, fiber optics to enable recording of a Raman signal using halogenated chromophores, which bind specifically to characteristic disease-proteins e.g. beta-amyloid for Alzheimer disease. The radiation may penatrate through the bone, and a Raman signal of a C—F bond of a contrast media, which is directly proportional to the concentration of the chromophore changes between diseased and normal cells, may be measured.

Multiplex analysis of genes may be performed to determine gene copy numbers and mRNA expression levels using multiple reporter dyes or single dyes. In gene quantification studies, the formation of a polymerase chain reaction (PCR) product is monitored continuously during amplification using fluorescent primers, fluorogenic probes, or fluorescent dyes that bind to double stranded DNA.

In one embodiment time-gated measurements may be used to distinguish between different C—F labels based on each labels' lifetime of emission in the fluorescence mode. A fixed set of excitation and emission filters may be used for measurements, and discrimination between labels may be achieved electronically.

The time based multiplex analysis of different C—F labels in the pulsed Raman mode of nucleic acids, proteins, or peptides is based on labeling with either C—F, $CF_2$, or $CF_3$, bonds. The bonds may be contained in aromatic or aliphatic, or N-containing compounds. Each of the C—F compounds and C—F molecules may have a characteristic Raman signature located in the area of 500 $cm^-$800 $cm^{-1}$, when excited by a pulsed laser source independent of the nature of the sample or media. The C—F compounds may also be differentiated from each other depending on the chemical structure of the compound. The C—F compounds that are aliphatic may be differentiated from each other based on the length of the molecule of each compound.

The instrument 300 400, 500 may be used in chromatography. For example, the instrument may be coupled to a chromatography instrument to detect a C—F bond in an eluent.

As discussed above, a carbon—halogen bond, such as a C—F bond, may be used as a label in PLIR, PLIF, and PLISERS applications because the bond exhibits a signal in a characteristic area, e.g., 500-900 $cm^{-1}$. The signal associated with the C—F bond may also be detected in a highly fluorescence surface, such as a nylon surface or biological matter by using time-gating and time-delay techniques. The C—F bond may retain its signal after being attached to biological molecules, such as Uridine (FIG. 25), Tryptophane (FIG. 24), Phenylalanine (FIG. 21) and Uracil (FIG. 22).

For PLIF applications, the C—F bond may produce a different spectrum from an unlabeled compound or biological molecule. (FIGS. 30 and 32). For PLIR and PLISERS applications, an unlabeled nucleic acid (DNA or RNA) fragment may not exhibit specific Raman signals. The incorporation of a C—F bond into such molecules may improve specificity of analysis. For PLISERS applications, bioprobes may be bound on a surface of a chip, bead, or nanoparticle. Such probes may be used for hybridization with C—F labeled probes. The signal of a C—F bond may be enhanced by a factor of about $10^6$ during a detection of the C—F label in colloidal solutions including gold or silver nanoparticles, or when detection is performed on surfaces, such as glass, chips, beads, or nanoparticles. A C—F bond or several C—F bonds may also exhibit a signal, when used with various platforms such as surfaces, gels or in solution. The C—F label may retain a characteristic signal after being attached to DNA-, RNA strands, peptide-nucleic acids or other biological probes, such as peptides, proteins, monoclonolal-, recombinant antibodies, antisense-molecules, ribozymes, aptamers, (oligo-) saccharides, or lipids. The C—F labeled probe may also be detected after hybridization or binding to a target molecule. The degree of hybridization/binding may be determined by measuring a change in the intensity of a C—F signal of the bound and unbound species, and a possible shift and the intensity of the C—F signal. Detection of fluorinated and non-fluorinated fluorescence dyes may also be performed in PLIF applications.

The analysis of fluoroorganic compounds where the compound is a drug, herbicide on vegetation, or pesticide on vegetation or animals may be performed. Fluorooorganic compounds used as drugs in animals to determine their presence and the presence of metabolites before excretion may be followed. Applications include pharmaceutical research and development, drug clinical trials, drug manufacturing, medical and biomedical applications. Also, organic fluorine compounds or derivatives which contaminate the environment can be detected at the nanogram level. Applications include environmental analysis of water, soil and air contaminated with fluorooorganic compounds, continuous monitoring of manufacturing fluorocarbon products and intermediates, and other similar applications. Dielectrics containing carbon-fluorine bonds are a further area of interest. The ultimate environmental fate of many fluorocarbon refrigerants is trifluoroacetic acid, which has been found in wetlands in environmental studies. Large numbers of soil samples for trifluoroacetic acid or for agriculture fluorinated pesticides may be analyzed. The research cost for developing new fluoroorganic pharmaceutical preparations, herbicides, and pesticides may be reduced.

Applications with respect to detecting other carbon—halogen bonds include carbon-chlorine, carbon-bromine, carbon-iodine, and carbon-astatine.

A number of embodiments of the present invention have been described. Nevertheless, it will be understood that various modifications may be made without departing from the spirit and scope of the invention. The copper-vapor laser-based Raman spectrograph described above may find broader applications. Accordingly, other embodiments are within the scope of the following claims.

We claim:

1. A method, comprising:
   providing a sample having a compound, biological molecule, bioprobe, material or product containing at least one carbon-halogen bond;
   applying a non-continuous light source to cause the sample to emit secondary emissions; and
   detecting at least one isochronic spectrum indicative of the at least one carbon halogen bond.

2. The method of claim 1, wherein the applying the non-continuous light source further comprises exposing the sample to a pulsed metal-vapor laser.

3. The method of claim 1, wherein the detecting at least one isochronic spectrum further comprises delaying the detection of secondary emissions of the at least one carbon halogen bond using a time delay device.

4. The method of claim 1, wherein the detecting at least one isochronic spectrum further comprises detecting the secondary emissions prior to fluorescence being emitted from the sample.

5. The method of claim 1, wherein the detecting at least one isochronic spectrum further comprises detecting the secondary emissions after detecting a Raman emission from the sample.

6. The method of claim 1, wherein the non-continuous light source comprises one of a gold-vapor laser, copper-vapor laser, solid-state laser, copper and gold vapor laser, a lead vapor laser, and a barium vapor laser.

7. The method of claim 1, wherein the at least one carbon-halogen bond comprises at least one carbon-fluorine bond and the applying the non-continuous light source comprises producing secondary emissions permitting detecting a fully symmetric vibrational normal mode of the at least one carbon-fluorine bond.

8. The method of claim 1, wherein the non-continuous light source further emits a wavelength that induces Raman scattered light emissions from the at least one carbon-halogen bond.

9. The method of claim 8, wherein three wavelengths inducing Raman scattered light emissions are approximately 510.6 nm, approximately 578.2 nm, and approximately 627.8 nm.

10. The method of claim 1, wherein the applying the non-continuous light source further comprises time-gating the non-continuous light source.

11. The method of claim 1, wherein the secondary emissions comprise Raman, resonance Raman, surface enhanced Raman and surface enhanced resonance Raman signatures.

* * * * *